US011124802B2

(12) United States Patent
Zou et al.

(10) Patent No.: US 11,124,802 B2
(45) Date of Patent: Sep. 21, 2021

(54) **MODULATING PLANT ABIOTIC STRESS RESPONSES USING THE *KANGHAN* GENE FAMILY**

(71) Applicant: NATIONAL RESEARCH COUNCIL OF CANADA, Ottawa (CA)

(72) Inventors: Jitao Zou, Saskatoon (CA); Wenyun Shen, Saskatoon (CA); Peng Gao, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 141 days.

(21) Appl. No.: 16/131,395

(22) Filed: Sep. 14, 2018

(65) Prior Publication Data

US 2019/0032074 A1 Jan. 31, 2019

Related U.S. Application Data

(63) Continuation-in-part of application No. PCT/IB2017/051474, filed on Mar. 14, 2017.

(60) Provisional application No. 62/308,580, filed on Mar. 15, 2016.

(51) Int. Cl.
*C12N 15/82* (2006.01)
*A01H 1/04* (2006.01)
*C07K 14/415* (2006.01)
*A01H 5/10* (2018.01)

(52) U.S. Cl.
CPC ........... *C12N 15/8273* (2013.01); *A01H 1/04* (2013.01); *A01H 5/10* (2013.01); *C07K 14/415* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,684,611 A | 8/1987 | Leiden et al. | |
| 4,743,548 A | 5/1988 | Crossway et al. | |
| 4,801,540 A | 1/1989 | Hiatt et al. | |
| 4,940,838 A | 7/1990 | Schilperoort et al. | |
| 4,943,674 A | 7/1990 | Houck et al. | |
| 4,945,050 A | 7/1990 | Sanford et al. | |
| 4,987,071 A | 1/1991 | Cech et al. | |
| 5,015,580 A | 5/1991 | Christou et al. | |
| 5,149,655 A | 9/1992 | McCabe et al. | |
| 5,175,095 A | 12/1992 | Martineau et al. | |
| 5,231,019 A | 7/1993 | Paszkowski et al. | |
| 5,283,184 A | 2/1994 | Jorgensen et al. | |
| 5,464,763 A | 11/1995 | Leiden et al. | |
| 5,466,587 A | 11/1995 | Fitzpatrick-McElligott et al. | |
| 5,591,610 A | 1/1997 | Cech et al. | |
| 5,723,765 A | 3/1998 | Oliver et al. | |
| 6,603,061 B1 | 8/2003 | Armstrong et al. | |
| 6,603,062 B1 | 8/2003 | Schmidt et al. | |
| 7,868,149 B2 | 1/2011 | Boukharov et al. | |
| 8,030,473 B2 | 10/2011 | Carrington et al. | |
| 8,476,422 B2 | 7/2013 | Carrington et al. | |
| 2009/0100536 A1 | 4/2009 | Adams et al. | |
| 2010/0192237 A1 | 7/2010 | Ren et al. | |
| 2012/0124693 A1 | 5/2012 | Guillen-Portal | |
| 2012/0198585 A1* | 8/2012 | Xiao | C12N 15/8273 800/279 |
| 2014/0223607 A1 | 8/2014 | Kuvshinov et al. | |

FOREIGN PATENT DOCUMENTS

| | | |
|---|---|---|
| CA | 2300692 A1 | 8/2000 |
| CN | 103172716 | 6/2013 |
| EP | 0255378 A2 | 2/1988 |
| EP | 0409625 A1 | 1/1991 |
| EP | 0409629 A1 | 1/1991 |
| KR | 20120119211 A | 10/2012 |
| WO | 8809334 A1 | 12/1988 |
| WO | 9113980 A1 | 7/1991 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Smith et al. (Nature Biotechnology, 15:1222-1223, 1997).*
Bork et al. (TIG, 12:425-427, 1996).*
Doerks et al., (TIG, 14:248-250, 1998).*
Nishimura et al. (Plant Cell Physiol., 41(5):583-590, 2000).*
Yang et al. (PNAS, 98:11438-11443, 2001).*
McConnell et al. (Nature, 411:709-713, 2001).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Joseph Ecker (Germplasm / Stock: SALK¬_008144.21.60.x submitted and available on public domain on Dec. 19, 2007).*
Alonso et al. (Science, 301:653-657, 2003).*
Zhou et al. (Plant Physiol., June 162(2):1030-1040; Published Jun. 2013; first published on line May 8, 2013).*
Nunes et al. (Planta 224:125-132; 2006).*

(Continued)

*Primary Examiner* — Vinod Kumar
(74) *Attorney, Agent, or Firm* — Jessica Smith

(57) ABSTRACT

Methods are provided for modulating an abiotic stress response to drought in a plant, for example by introducing a heritable change to the plant, which alters the expression in the plant of an endogenous or exogenous protein that is a member of a particular gene family, the Kanghan genes. Similarly, plants and plants cells having such heritable changes are provided.

14 Claims, 15 Drawing Sheets

Specification includes a Sequence Listing.

(56) References Cited

OTHER PUBLICATIONS

Schneider et al, Sequence logos: a new way to display consensus sequences, Nucleic Acids Research, 1990, 18(20): 6097-6100.

Yang et al, Narrowing down the targets: towards successful genetic engineering of drought-tolerant crops. Molecular Plant, 2010, 3(3): 469-490.

Allen et al. miRNAs in the biogenesis of trans-acting siRNAs in higher plants. Seminars in Cell & Developmental Biology. 2010; 21:798-804.

Byrt et al. Living with salinity. New Phytologist. 2008; 179:903-905.

Felippes et al. Triggering the formation of tasiRNAs in *Arabidopsis thaliana*: the role of microRNA miR173. EMBO Rep 2009; 10:264-270.

Khraiwesh et al. Role of miRNAs and siRNAs in biotic and abiotic stress responses of plants. Biochimica Et Biophysica Acta-Gene Regulatory Mechanisms 2012; 1819:137-148.

Kruszka et al. Role of microRNAs and other sRNAs of plants in their changing environments. Journal of Plant Physiology 2012; 169:1664-1672.

Kume et al. TAS1 trans-Acting siRNA Targets Are Differentially Regulated at Low Temperature, and TAS1 trans-Acting siRNA Mediates Temperature-Controlled At1g51670 Expression. Bioscience, Biotechnology and Biochemistry. 2010; 74(7):1435-1440.

Marin et al. miR390, *Arabidopsis* TAS3 tasiRNAs, and their Auxin Response Factor targets define an autoregulatory network quantitatively regulating lateral root growth. Plant Cell 2010; 22: 1104-1117.

Montgomery et al. AG01-miR173 complex initiates phased siRNA formation in plants. Proc Natl Acad Sci USA 2008; 105: 20055-20062.

Munns et al. Mechanisms of salinity tolerance. Annual Review of Plant Biology. 2008; 59:651-681.

Rajagopolan et al. A diverse and evolutionarily fluid set of microRNAs in *Arabidopsis thaliana*. Genes & Dev. 2006;20:3407-3425.

Sunkar et al. Novel and Stress-Regulated MicroRNAs and Other Small RNAs from *Arabidopsis*. The Plant Cell. (2004) vol. 16, 2001-2019.

Trindade et al. (2011) Facing the Environment: Small RNAs and the Regulation of Gene Expression Under Abiotic Stress in Plants. Chapter 5 in Abiotic Stress Response in Plants—Physiological, Biochemical and Genetic Perspectives. Shanker and Venkateswarlu eds. (InTech, Croatia, 2011).

Xin et al. Diverse set of microRNAs are responsive to powdery mildew infection and heat stress in wheat (*Triticum aestivum* L.). BMC Plant Biology. 2010; 10, 123 (11 pages).

Zhu. Salt and drought stress signal transduction in plants. Annual Review of Plant Biology. 2002; 53:247-273.

Altschul et al, Basic local alignment search tool, J. Mol. Biol., 1990, 215(3): 403-410.

Belhaj et al., Plant genome editing made easy: targeted mutagenesis in model and crop plants using the CRISPR/Cas system, Plant Methods, 2013, 9:39.

Brooks, Efficient Gene Editing in Tomato in the First Generation Using the Clustered Regularly Interspaced Short Palindromic Repeats/CRISPR-Associated9 System, Plant Physiology, Plant Physiology Nov. 2014, 166 (3) 1292-1297.

Caliando et al, Targeted DNA degradation using a CRISPR device stably carried in the host genome, Nature Communications, 2015, 6:6989.

Close et al, The effect of auxin-like plant growth regulators and osmotic regulation on induction of somatic embryogenesis from elite maize inbreds, Plant Science, 1987, 52(1-2):81-89.

Crooks et al., WebLogo: A Sequence Logo Generator, Genome Research, 2004, 14:1188-1190.

Duncan et al, The production of callus capable of plant regeneration from immature embryos of numerous *Zea mays* genotypes, Planta, 1985, 165:322-332.

Dunsmuir et al, A number of different nuclear genes for the small subunit of RuBPCase are transcribed in petunia, Nucleic Acids Res, 1983, 11(12):4177-4183.

Feng et al, Efficient genome editing in plants using a CRISPR/Cas system, Cell Research, 2013, 23:1229-1232.

Fraley et al, Expression of bacterial genes in plant cells, Proc. Nat'l Acad. Sci. USA, 1983, 80(15):4803-4806.

Fromm et al, Expression of genes transferred into monocot and dicot plant cells by electroporation, Proc. Natl. Acad. Sci. USA, 1985, 82:5824.

Gordon-Kamm et al., Transformation of Maize Cells and Regeneration of Fertile Transgenic Plants, The Plant Cell, 1990, 2(7):603-618.

Hatfield et al, Temperature extremes: effect on plant growth and development, Weather and Climate Extremes, 2015, 10 (Part A):4-10.

Henikoff et al, Amino acid substitution matrices from protein blocks, Proc. Natl. Acad. Sci. USA, 1992, 89(22): 10915-10919.

Horsch et al. Inheritance of Functional Foreign Genes in Plants, Science, 1984, 233(4635): 496-498.

Klee et al., Agrobacterium-mediated plant transformation and its further applications to plant biology, Ann. Rev. of Plant Phys., 1987, 38:467-486.

Klein et al., High-velocity microprojectiles for delivering nucleic acids into living cells, Nature, 1987, 327: 70-73.

Kumar et al, RuBisCo activase—a catalytic chaperone involved in modulating the RuBisCo activity and heat stress-tolerance in wheat, Journal of Plant Biochemistry and Biotechnology, Jul. 18, 2018, 28: 63-75.

Li et al, Targeted Plant Genome Editing via the CRISPR/Cas9 Technology, 2015, In: Alonso J., Stepanova A. (eds) Plant Functional Genomics. Methods in Molecular Biology, vol. 1284. Humana Press, New York, NY. https://doi.org/10.1007/978-1-4939-2444-8_12.

Mein et al., Evaluation of Single Nucleotide Polymorphism Typing with Invader on PCR Amplicons and Its Automation, Genome Research, 2000, 10: 330-343.

Morrell et al., Crop genomics: advances and applications, Nat Rev Genet., Dec. 29, 2011, 13(2):85-96.

Myakishev et al., High-Throughput SNP Genotyping by Allele-Specific PCR with Universal Energy-Transfer-Labeled Primers, Genome Research, 2001, 11: 163-169.

Napoli et al., Introduction of a Chimeric Chalcone Synthase Gene into Petunia Results in Reversible Co-Suppression of Homologous Genes in trans, Plant Cell, 1990, 2 (4): 279-289.

Needleman et al, A general method applicable to the search for similarities in the amino acid sequence of two proteins, J. Mol. Biol., 1970, 48(3):443-453.

Nilsson et al, Genetic ablation of flowers in transgenic *Arabidopsis*, The Plant Journal, 1998, 15(6): 799-804.

Orita et al., Detection of polymorphisms of human DNA by gel electrophoresis as single-strand conformation polymorphisms, Proc. Natl. Acad. Sci. U.S.A., 1989, 86(8): 2766-2770.

Paszkowski et al., Direct gene transfer to plants, EMBO J., 1984, 3:2717-2722.

Pearson et al, Improved tools for biological sequence comparison, Proc. Natl. Acad. Sci. USA, 1988, 85(8): 2444-2448.

Pear et al, Isolation and characterization of a fruit-specific cDNA and the corresponding genomic clone from tomato, Plant Mol. Biol, 1989, 13:639-651.

Pokalsky et al, Structure and expression of elongation factor 1α in tomato, Nucleic Acids Res, 1989, 17(12):4661-4673.

Rajeevkumar et al, Epigenetic silencing in transgenic plants, Front. Plant Sci., 2015, 6:693.

Rizhsky et al., When Defense Pathways Collide. The Response of *Arabidopsis* to a Combination of Drought and Heat Stress, Plant Physiology, Apr. 2004, vol. 134 (4): 1683-1696.

Rogers et al., Gene transfer in plants: Production of transformed plants using Ti plasmid vectors, Methods Enzymol., 1986, 118:627-640.

Schneider et al, Sequence logos: a new way to display consensus sequences, Nucleic Acids Res., 1990, 18(20):6097-6100.

(56) References Cited

OTHER PUBLICATIONS

Shan et al, Targeted genome modification of crop plants using a CRISPR-Cas system, Nature Biotechnology, 2013, 31, 686-688.
Smith et al, Comparison of biosequences, Adv. Appl. Math, 1981, 2(4): 482-489.
Tanhuanpää et al., Mapping and cloning of FAD2 gene to develop allele-specific PCR for oleic acid in spring turnip rape (*Brassica rapa* ssp. oleifera), Molecular Breeding, 1999, 4: 543-550.
Täpp et al., Homogeneous Scoring of Single-Nucleotide Polymorphisms: Comparison of the 5'-Nuclease TaqMan® Assay and Molecular Beacon Probes, BioTechniques 28(4): 732-738.
Taylor W. R., The classification of amino acid conservation, J. Theor. Biol., 1986, 119:205-218.
Thiagrarajah et al, A comparison of genetic segregation in traditional and microspore-derived populations of *Brassica juncea* in: L. Czern and Coss. Plant Breeding, 1993, 111:330-334.
Xie et al, RNA-Guided Genome Editing in Plants Using a CRISPR-Cas System, Mol Plant, 2013, 6(6):1975-1983.
Xu et al, Gene targeting using the Agrobacterium tumefaciens-mediated CRISPR-Cas system in rice, Rice, 2014, 7:5.
Yang et al., Narrowing Down the Targets: Towards Successful Genetic Engineering of Drought-Tolerant Crops, Molecular Plant, vol. 3, Issue 3, May 2010, pp. 469-490.

\* cited by examiner

FIG. 4

FIG. 9A
FIG. 9B
FIG. 9C
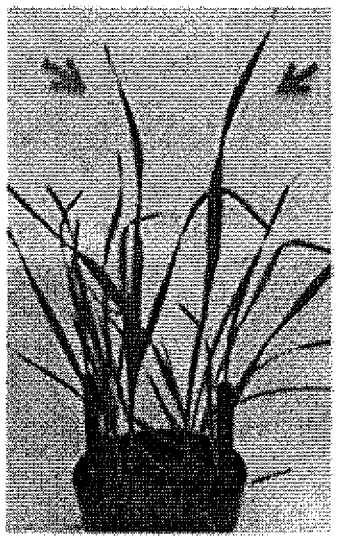
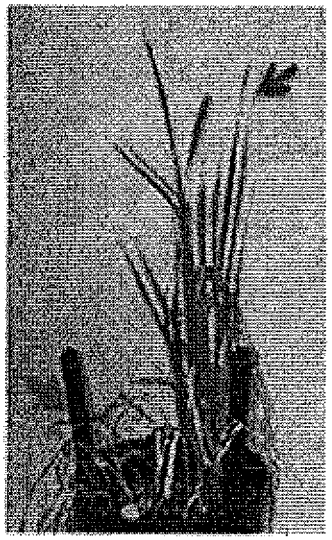
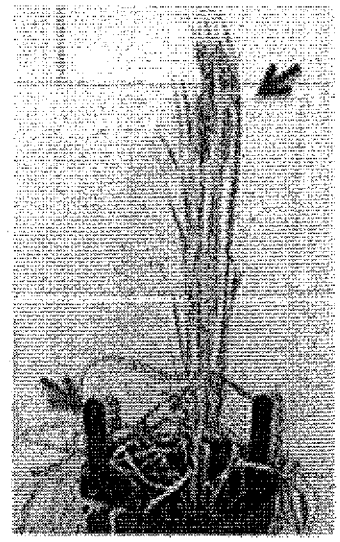
FIG. 10
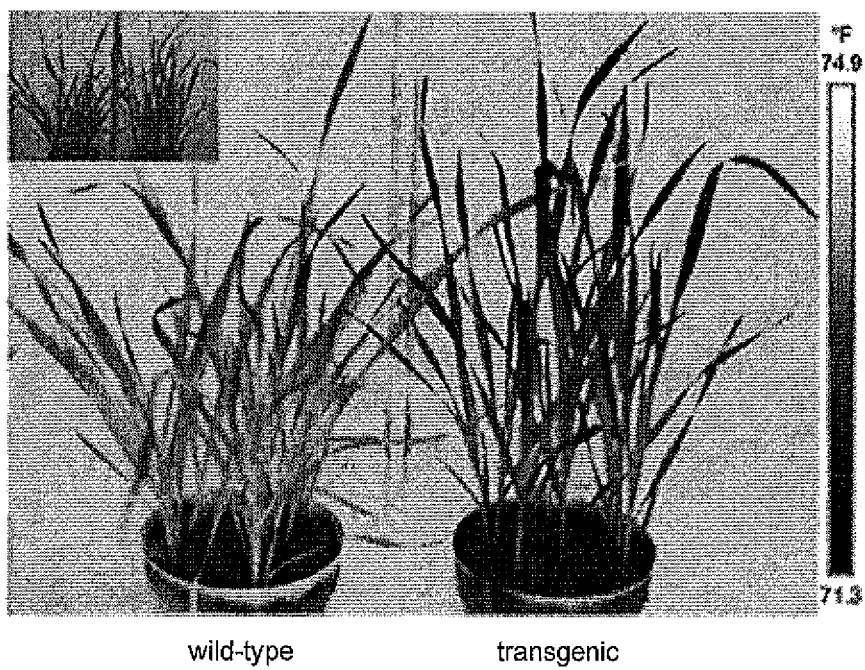
wild-type    transgenic

MODULATING PLANT ABIOTIC STRESS RESPONSES USING THE *KANGHAN* GENE FAMILY

CROSS-REFERENCE TO RELATED APPLICATIONS

This application is a continuation-in-part of International Application No. PCT/IB2017/051474, filed Mar. 14, 2017 and further claims the benefit of U.S. Provisional Application No. 62/308,580, filed Mar. 15, 2016.

FIELD OF THE INVENTION

The present invention relates to abiotic stress-resistant plants and processes for obtaining them, including flowering plants and seeds thereof.

BACKGROUND OF THE INVENTION

Abiotic stress is a major challenge facing the agricultural industry (see Yang et al., Molecular Plant, Volume 3, Issue 3, May 2010, Pages 469-490). Abiotic stresses such as drought and heat not only cause a reduction in crop yield, but also cause high variation in crop yield. Improving crop tolerance to abiotic stresses such as heat and drought is essential for maintaining a stable yield under the continued threat of climate change. It is also a key factor for sustaining and expanding arable land areas for crop production.

Plants have evolved various mechanisms to cope with abiotic stress at both the physiological and biochemical levels. Many stress-induced genes have been identified, including those encoding key enzymes for abscisic acid (ABA) biosynthesis and signaling transduction components such as protein kinases, protein phosphatases and transcription factors. In recent years, several stress-regulated miRNAs have also been identified in model plants under biotic and abiotic stress conditions. Plants respond differently to drought and heat stress (Rizhsky et al., Plant Physiology, April 2004, Vol. 134, pp. 1683-1696).

SUMMARY

Methods are provided for modulating an abiotic stress response to drought or heat in a plant, for example by introducing a heritable change to the plant, which alters the expression in the plant of an endogenous or exogenous Kanghan protein. Similarly, plants and plants cells having such heritable changes are provided.

Plants having enhanced drought tolerance are accordingly provided, for example by altering selected quantitative trait loci (QTL) associated with the family of Kanghan genes. Suppression of Kanghan genes, for example in null mutations, confers drought tolerance.

Methods are accordingly provided for modulating an abiotic stress response to drought in a plant, comprising introducing a heritable change to the plant which alters the expression in the plant of an endogenous or exogenous Kanghan protein. The Kanghan protein may for example be at least 35% identical to, or at least 49% positively aligned with, a protein encoded by the nucleotide sequence set forth in SEQ ID NO: 1, SEQ ID NO: 2, SEQ ID NO: 3, SEQ ID NO: 4, SEQ ID NO: 5, and/or SEQ ID NO: 13; and this alignment may for example be over an alignment length of at least 90 amino acids, with BLOSUM or PAM substitution matrix, with gaps permitted. Alternative degrees of sequence similarity are contemplated in alternative embodiments, for example 50%, 75%, 90% or 95% identical to, or at least 75%, 90% or 100% positively aligned with, the protein encoded by the nucleotide sequence set forth in SEQ ID NO: 1, SEQ ID NO: 2, SEQ ID NO: 3, SEQ ID NO: 4, SEQ ID NO: 5, or SEQ ID NO: 13; over an alignment length of at least 90, 100 or 110 amino acids, with BLOSUM or PAM substitution matrix, and with gaps permitted.

The Kanghan protein includes a variety conserved domains, such as domains: identical to hTVKDChphAhp (SEQ ID NO: 6); and/or, at least 80% identical to LTVKD-CLEhAhK-G (SEQ ID NO: 7); and/or, at least 70% identical to LTVKDCLEhAFKKG (SEQ ID NO: 8); and/or at least 80% identical to VshKGpVlEstshpEs.chhhpQs-huA+LHlFpPph (SEQ ID NO: 9); and/or, at least 70% identical to VsMKGEVIEspsh-EAhcLllcQP-lGA+LHlFoPcl (SEQ ID NO: 10); and/or, at least 80% identical to cppDYDtSt-pAAhVAlpLISSARlhLKlDuhhTEYSsQaLhDpsutpp (SEQ ID NO: 11); and/or, at least 70% identical to spphhpShup-scGhCHPDC-KAssEpEDYDASQpAAhVAVsLISSAR-lhLKLDusaTEYSAQYLVDNAGpccs (SEQ ID NO: 12).

In alternative embodiments, the plant may lack an endogenous Kanghan protein, such as a protein that has the sequence characteristics of Kanghan proteins described above, such as being at least 35% identical to, or at least 49% positively aligned with, a protein encoded by the nucleotide sequence set forth in SEQ ID NO: 1, SEQ ID NO: 2, SEQ ID NO: 3, SEQ ID NO: 4, SEQ ID NO: 5, or SEQ ID NO: 13; over an alignment length of at least 90 amino acids, with BLOSUM or PAM substitution matrix.

The plant may be an angiosperm, and may for example belong to the family of Brassicaceae, Fabaceae, Poaceae, or Asteraceae plants. The plant may for example be a *Caspsella rubella*, *Brassica rapa*, *Brassica napus*, *Brassica carinata*, *Eutrema salsugineum*, *Thellugiella parvula*, *Camelina sativa*, *Glycine max*, *Triticum*, *Zea* maize, *Oryza sativa* or *Helianthus annuus* plant.

The heritable change may be one that sufficiently decreases the expression of the Kanghan protein so as to enhance drought tolerance relative to an unmodified plant, for example improving drought tolerance by an objective measure by 10% to 100% or more.

The heritable change may for example involve expressing in the plant an inhibitory polynucleotide that down-regulates the expression of the Kanghan protein, such as an inhibitory RNA, for example an anti-sense oligonucleotide, an RNAi oligonucleotide, a microRNA, a small interfering RNA, or a CRISPR guide RNA. Alternatively, the heritable change may be an alteration of a Kanghan gene sequence encoding the Kanghan protein, for example by transformation with an exogenous Kanghan gene encoding the exogenous Kanghan protein, or by editing or mutation of an endogenous Kanghan gene encoding the endogenous Kanghan protein. The editing or mutation may for example introduce a change to a coding sequence of the Kanghan gene which changes the amino acid sequence of the Kanghan protein.

In accordance with the foregoing methods, there are also provided parental plants or plant cells that are produced by these processes. Similarly, plant lines, varieties or cultivars are provided that include the parental plant or plant cell, and the plant line, variety or cultivar may for example be characterized by an improved drought tolerance characteristic. Seeds and plant parts are provided, for example from foregoing plant lines, varieties or cultivars. Seeds in turn may be used to provide progeny plants, such as progeny plants that are genetically derived from the plant line, variety or cultivar so as to retain the improved drought tolerance characteristic.

Methods of marker assisted selection may for example be used to introduce the heritable change, with subsequent screening of the plant or plant cell or progeny for the desired modulation of the abiotic stress response to drought.

A further embodiment is a method for producing a plant having increased tolerance to heat stress, comprising introducing into a plant cell an expression construct comprising a nucleic acid molecule encoding a polypeptide with at least 80% identity to SEQ ID NO: 14, SEQ ID NO: 15, SEQ ID NO: 16, SEQ ID NO: 17, SEQ ID NO: 18, and/or SEQ ID NO: 19 over an alignment length of at least 90 amino acids, operatively linked to at least one regulatory element, said at least one regulatory element being effective to direct expression of said nucleic acid molecule in the plant; and growing the plant cell into the plant. In another embodiment, the nucleic acid molecule encodes a polypeptide with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to SEQ ID NO: 14, SEQ ID NO: 15, SEQ ID NO: 16, SEQ ID NO: 17, SEQ ID NO: 18, and/or SEQ ID NO: 19 over an alignment length of at least 90 amino acids, at least 100 amino acids, at least 110 amino acids, or over the full length of the amino acid sequence set forth in SEQ ID NO: 14, SEQ ID NO: 15, SEQ ID NO: 16, SEQ ID NO: 17, SEQ ID NO: 18, or SEQ ID NO: 19. The polypeptide encoded by the nucleic acid molecule will preferably have the same biological activity as the polypeptide set forth in SEQ ID NO: 14, SEQ ID NO: 15, SEQ ID NO: 16, SEQ ID NO: 17, SEQ ID NO: 18, or SEQ ID NO: 19. In an embodiment, at least one regulatory element comprises a promoter, for example a constitutive promoter. In a further embodiment, the regulatory element is a regulatory element that is not naturally in operative linkage with the nucleic acid molecule. For example, the regulatory element may be a synthetic regulatory element, a regulatory element derived from a different species than the nucleic acid molecule, or a regulatory element derived from a different gene within the same species as the nucleic acid molecule. In an embodiment, the nucleic acid molecule is derived from a different species than the plant cell into which the expression construct is introduced. In a further embodiment, the nucleic acid molecule is derived from *Arabidopsis* and the plant cell is a *Triticum* cell.

The method may further comprise a step of assessing the heat tolerance of the plant relative to a control plant of the same variety or genetic background that does not comprise the expression construct and identifying the plant as having increased tolerance to heat stress if it exhibits increased heat tolerance relative to the control plant. Tests for heat tolerance are known and will be understood by one skilled in the art (for example, see Kumar et al, Journal of Plant Biochemistry and Biotechnology, July 2013; Hatfield and Prueger (2015), Weather and Climate Extremes 10:4-10). In wheat, heat tolerance may be assessed by, for example, subjecting newly germinated seedlings, seedlings, or plants to heat stress at a temperature of about 27 or higher of about 30° C. or higher (e.g. conditions such as 36° C., 42/38° C. (day/night), or 40/38° C. (day/night)) for a period of time (typically days or weeks, for example two or three weeks) then allowing them to recover at a standard growth temperature between about 13-25° C. (e.g. growth conditions such as 25° C., 25/20° C. (day/night), 24/16° C. (day/night), or 18/13° C. (day/night)) for a period of time (e.g. 3-10 weeks) and then measuring viability or another indicator of heat stress, such as yield, biomass, or canopy temperature.

Further provided is a plant cell, plant, seed, or plant tissue comprising an expression construct as described above. In an embodiment, the plant cell, plant, seed, or plant tissue is a Poaceae cell, plant, seed, or tissue. In a further embodiment, the plant cell, plant, seed, or plant tissue is a cereal plant cell, plant, seed, or tissue. Cereal plants include commercially important grain crops such as rice (*Oryza sativa*), wheat/spelt (*Triticum*), corn/maize (*Zea mays*), barley (*Hordeum vulgare*), Sorghum, oat (*Avena sativa*), rye (*Secale cereale*), and Triticale. In a further embodiment, the plant cell, plant, seed, or plant tissue is *Triticum*.

In accordance with the foregoing methods, there are also provided parental plants or plant cells that are produced by these processes. Seeds in turn may be used to provide progeny plants, such as progeny plants that are genetically derived from the plant line, variety or cultivar so as to retain the improved drought tolerance characteristic. Seeds and plant parts that are derived from the foregoing plant lines may be characterized by improved drought tolerance characteristics, for example they may be subjected to RNAseq analyses to identify transcripts that exhibit contrasting differential expression patterns when compared with their respective wild type controls. The combinatory profile of these genes can be an evaluation benchmark for drought tolerance.

Methods of marker assisted selection may for example be used to introduce the heritable change, with subsequent screening of the plant or plant cell or progeny for the desired modulation of the abiotic stress response to drought.

BRIEF DESCRIPTION OF THE DRAWINGS AND LIST OF SEQUENCES

In order that the invention may be more clearly understood, embodiments thereof will now be described in detail by way of example, with reference to the accompanying drawings, in which.

Figure 3:
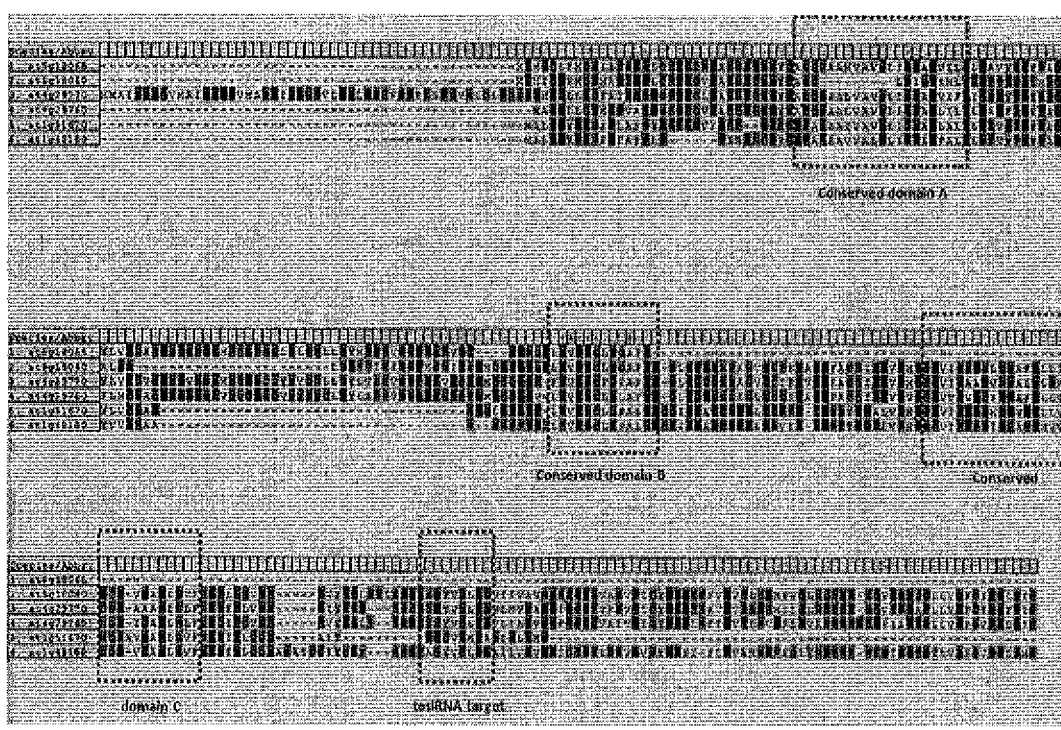

FIG. 3 roughly depicts the relative location of 4 conserved protein domains within six members of the *Arabidopsis* Kanghan gene family: at5g18065 (SEQ ID NO: 16), at5g18040 (SEQ ID NO: 17), at4g29770 (SEQ ID NO: 15), at4g29760 (SEQ ID NO: 14), at1g48180 (SEQ ID NO: 19), and at1 g51670 (SEQ ID NO: 18).

Figure 4:
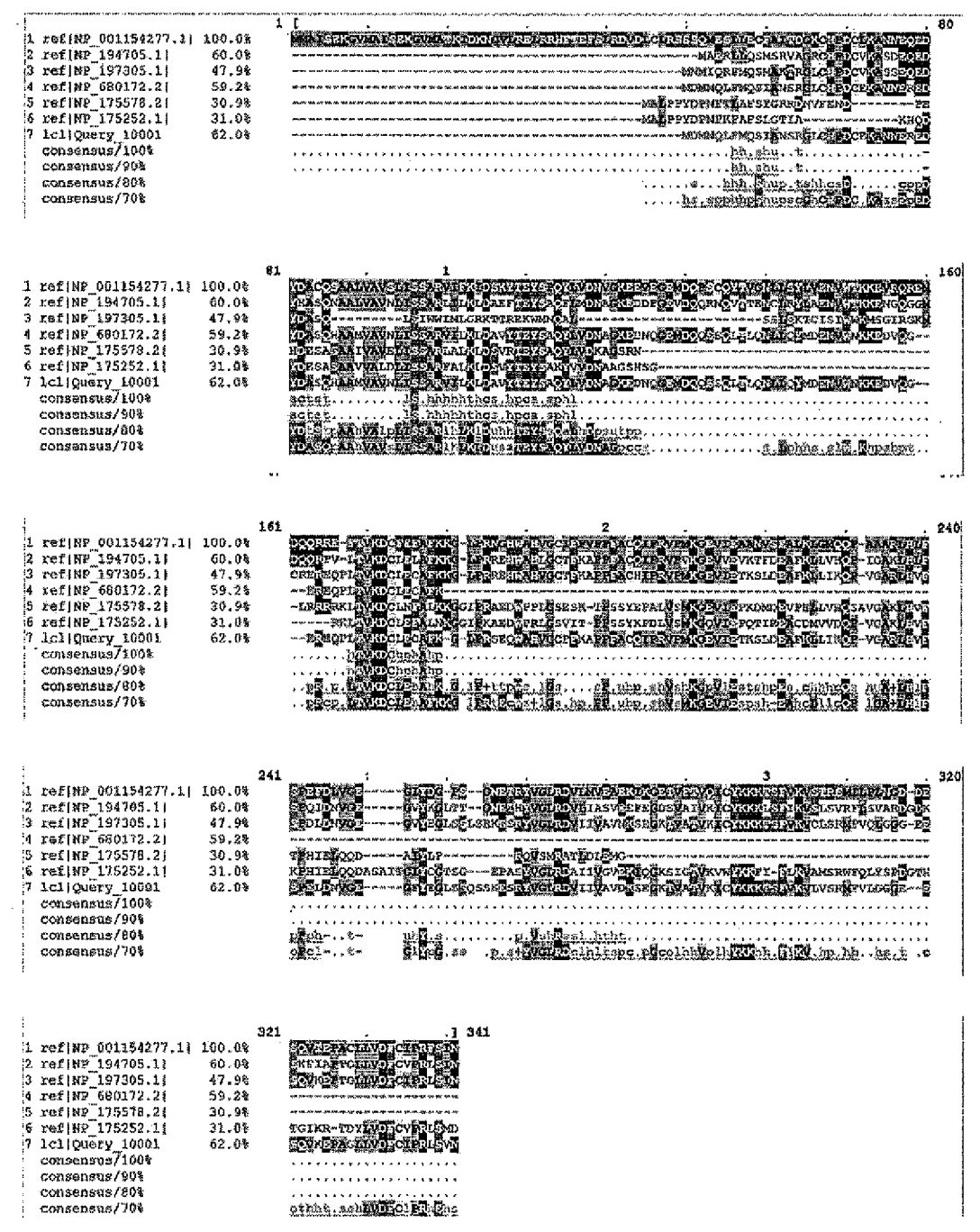

FIG. 4 is an alternative illustration of the conserved protein domains within the six members of the *Arabidopsis* Kanghan gene family, at5g18040 (SEQ ID NO: 17, identified as ref|NP_197305.1|), at4g29770 (SEQ ID NO: 15, identified as ref|NP_001154277.1|), at4g29760 (SEQ ID NO: 14, identified as ref|NP_194705.1|), at1g48180 (SEQ ID NO: 19, identified as ref|NP_175252.1|), at5g18065 (SEQ ID NO: 16, identified as ref|NP_680172.2|), and at1g51670 (SEQ ID NO: 18, identified as ref|NP_175578.2|), with an additional sequence identified as "lcl|Query_10001" (SEQ ID NO: 40) which is the sequence of at5g18065 plus the translation of the at5g18065 cDNA following what appears to be a premature stop codon in at5g18065 which truncates the protein. Alternative protein consensus sequences are also set out in FIG. 4, with varying degrees of sequence consensus as illustrated (with lower case descriptors for residues having conserved properties based on Taylor W. R. (1986) J. Theor. Biol. 119:205-218, as follows: alcohol=>o {S, T}, aliphatic=>1 {I, L, V}, aromatic=>a {F, H, W, Y}, charged=>c {D, E, H, K, R}, hydrophobic=>h {A, C, F, G, H, I, K, L, M, R, T, V, W, Y}, negative=>- {D, E}, polar=>p {C, D, E, H, K, N, Q, R, S, T}, positive=>+{H, K, R}, small=>s {A, C, D, G, N, P, S, T, V}, tiny=>u {A, G, S}, turnlike=>t {A, C, D, E, G, H, K, N, Q, R, S, T}. The 100% and 90% consensus sequences are identical and this sequence is set forth in SEQ ID NO: 41, the 80% consensus sequence is set forth in SEQ ID NO: 42, and the 70% consensus sequence is set forth in SEQ ID NO: 43.

Figure 5:

FIG. 5 depicts conserved domain A in Kanghan proteins using a sequence logo, using the sequence of the 5 Kanghan proteins identified by QTL analysis as having the greatest contribution to drought tolerance. Amino acid positions 51 to 128 in the consensus sequence depicted in FIG. 5 correspond to amino acid positions 7 to 84 of SEQ ID NO: 43.

Figure 6:
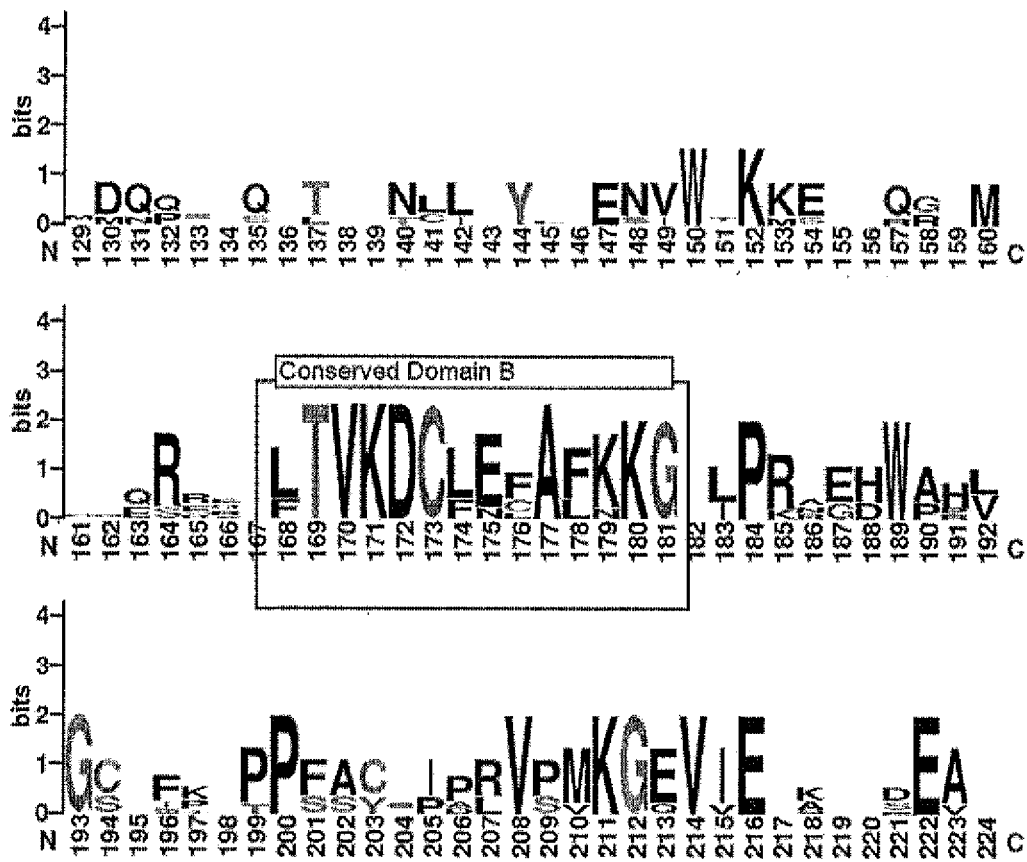

FIG. 6 is a continuation of FIG. 5, depicting conserved domain B in Kanghan proteins using a sequence logo, using the sequence of the 5 Kanghan proteins identified by QTL analysis as having the greatest contribution to drought tolerance. Amino acid positions 129 to 224 in the consensus sequence depicted in FIG. 6 correspond to amino acid positions 85 to 180 of SEQ ID NO: 43.

Figure 7:
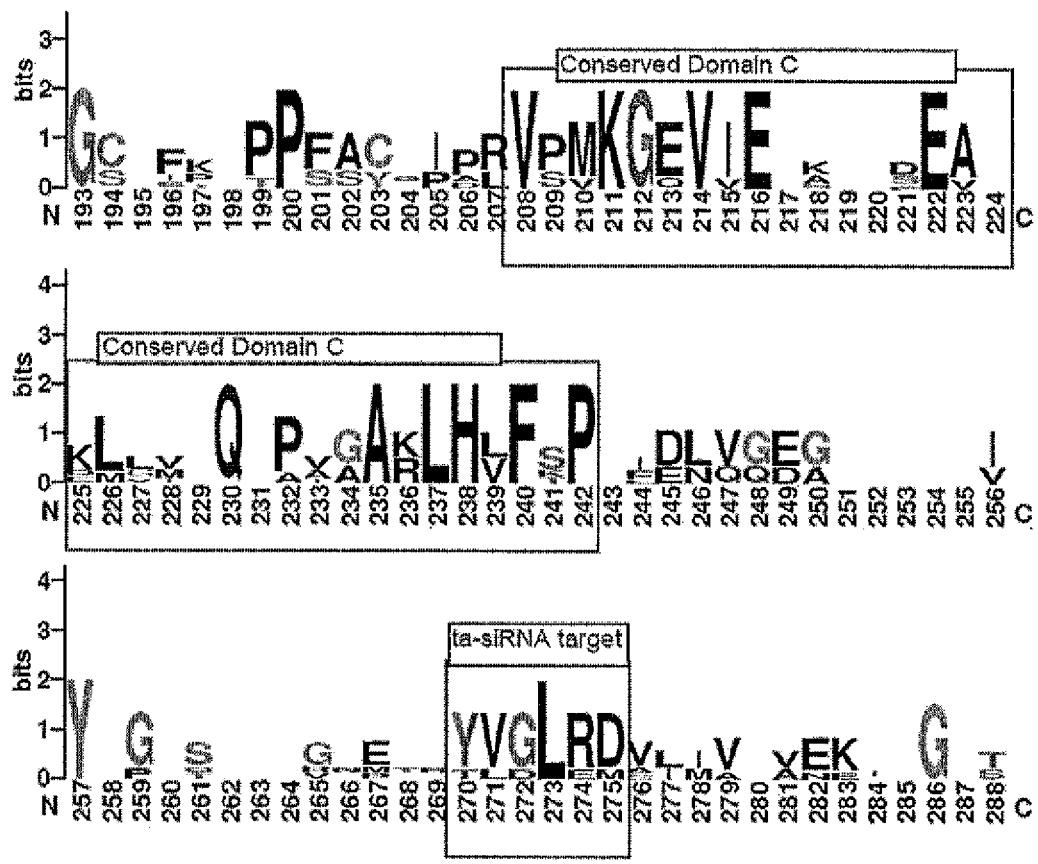

FIG. 7 is a continuation of FIG. 6, depicting conserved domain C in Kanghan proteins using a sequence logo, using the sequence of the 5 Kanghan proteins identified by QTL analysis as having the greatest contribution to drought tolerance. Amino acid positions 193 to 288 in the consensus sequence depicted in FIG. 6 correspond to amino acid positions 148 to 235 of SEQ ID NO: 43.

Figure 8:
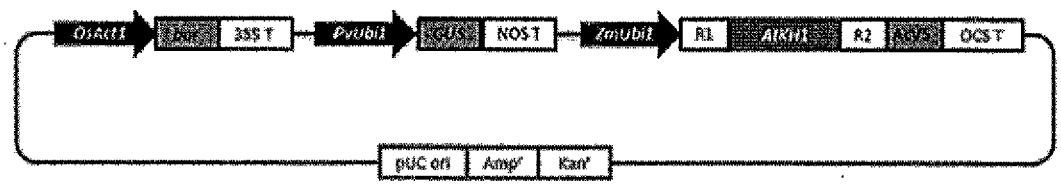

FIG. 8 is a diagram depicting the construct for overexpression of *Arabidopsis* Kanghan1 in wheat wild type (Fielder) based on the monocot special overexpression vector PANIC5E.

FIG. 9A is a photograph of 3 week old wild-type (left) and transgenic (right) wheat seedlings grown under standard conditions (25° C.). The transgenic wheat seedlings heterologously express At5g18040.

FIG. 9B is a photograph of the plants from FIG. 9A, after being incubated for three weeks at 40/38° C. (day/night), followed by three weeks at 25° C.

FIG. 9C is a photograph of the plants from FIG. 9B after being grown for an additional seven weeks at 25° C.

FIG. 10 is a near infrared leaf surface temperature image of wild-type (left) and transgenic (right) wheat plants grown under standard conditions. The transgenic wheat plant expresses At5g18040 from a heterologous At5g18040 expression construct.

Figure 11:
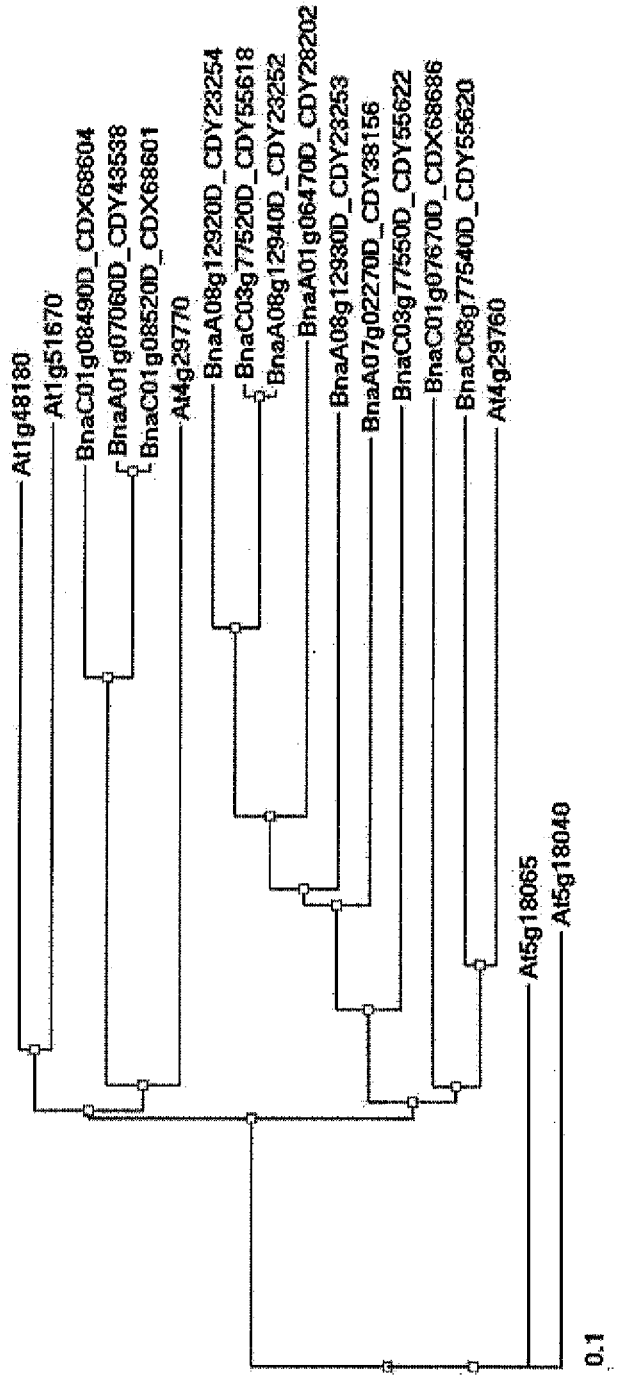

FIG. 11 shows a DNA neighbor phylogenetic tree of the *Brassica napus* Kanghan gene candidates and their *Arabidopsis thaliana* counterparts.

Figure 12:
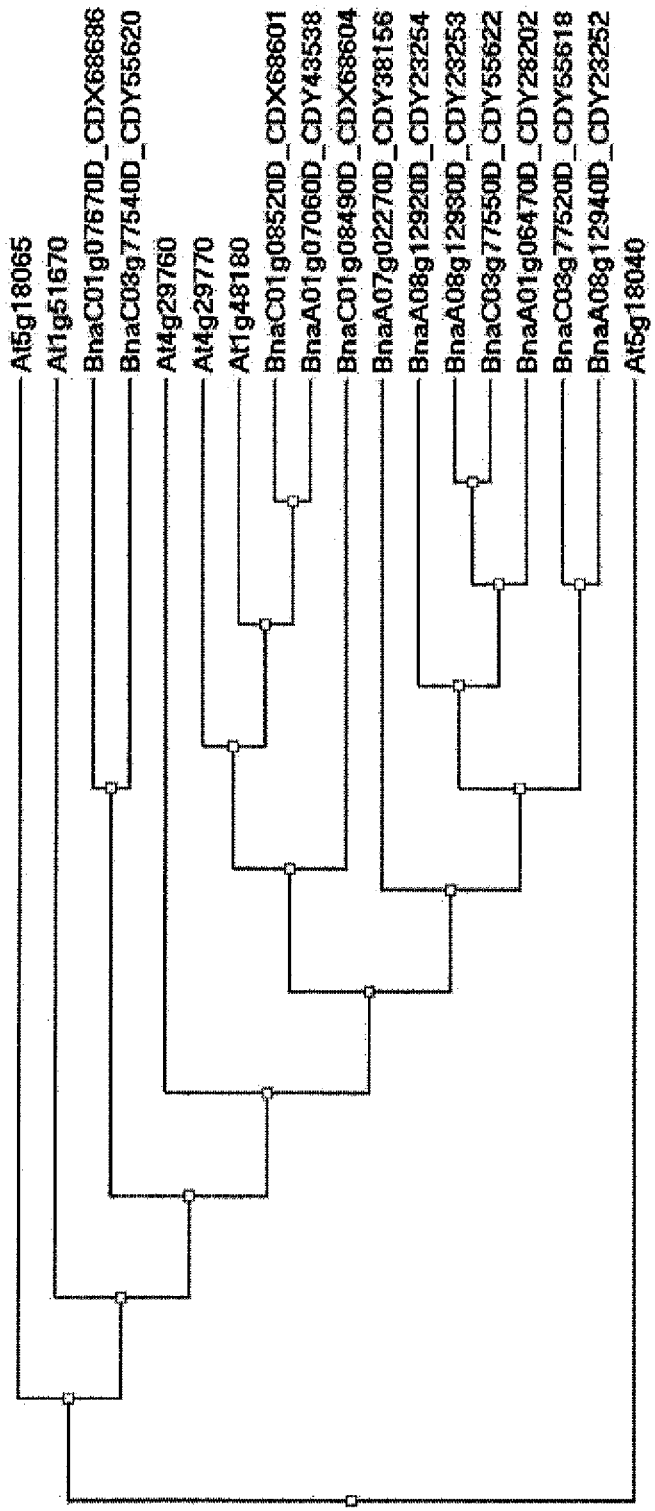

FIG. 12 shows a protein neighbor phylogenetic tree of the *Brassica napus* Kanghan gene candidates and their *Arabidopsis thaliana* counterparts.

Figure 13:
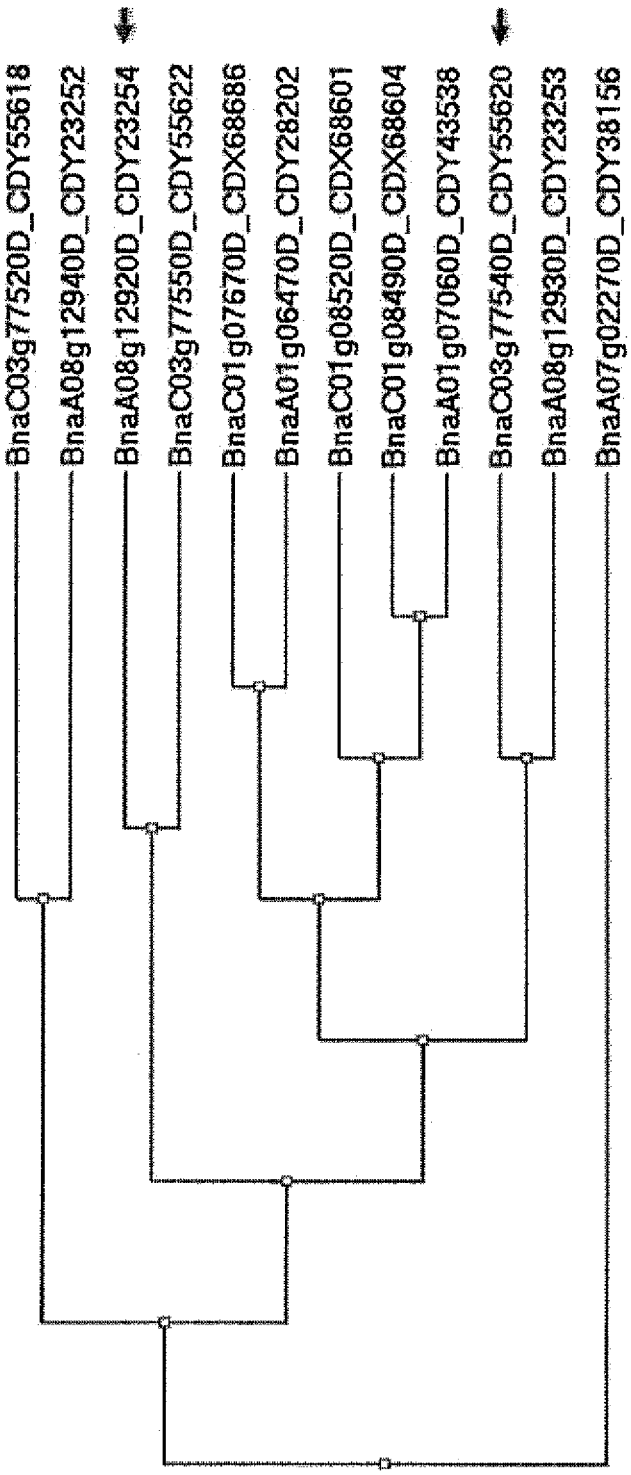

FIG. 13 shows a DNA neighbor phylogenetic tree of the *Brassica napus* Kanghan gene candidates.

Figure 14:
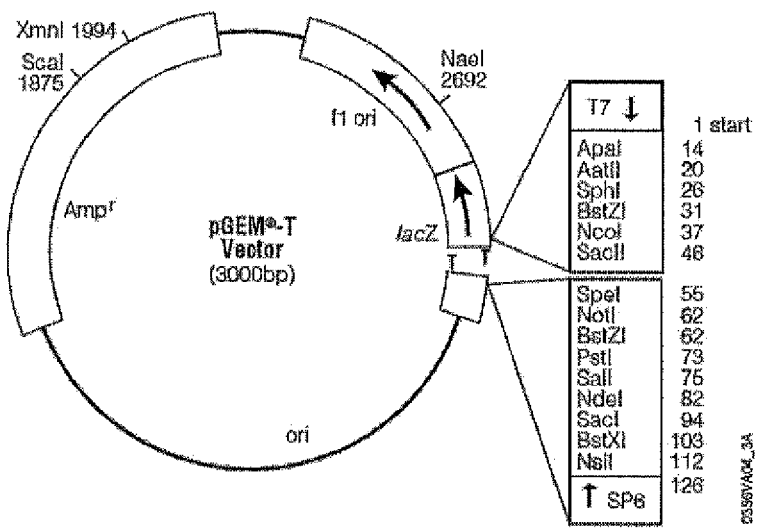

FIG. 14 shows a map of the pGEM®-T vector (Promega, USA).

Figure 15:
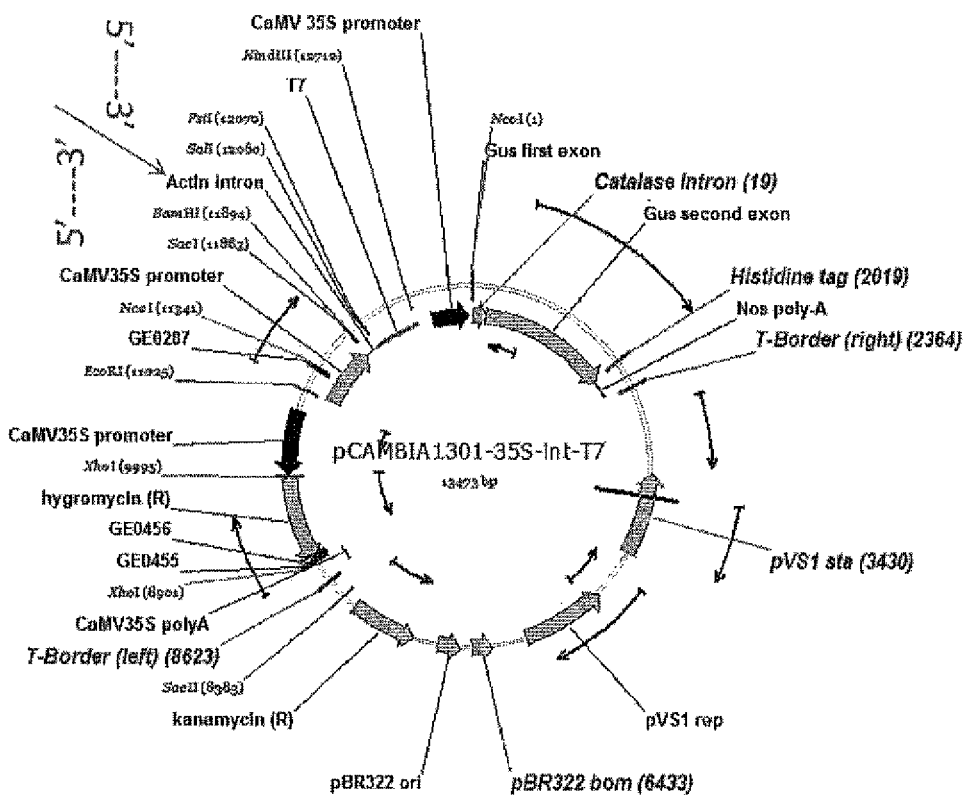

FIG. 15 shows a map of the pCAMBIA 1301-35S-Int-T7 vector.

Figure 16:
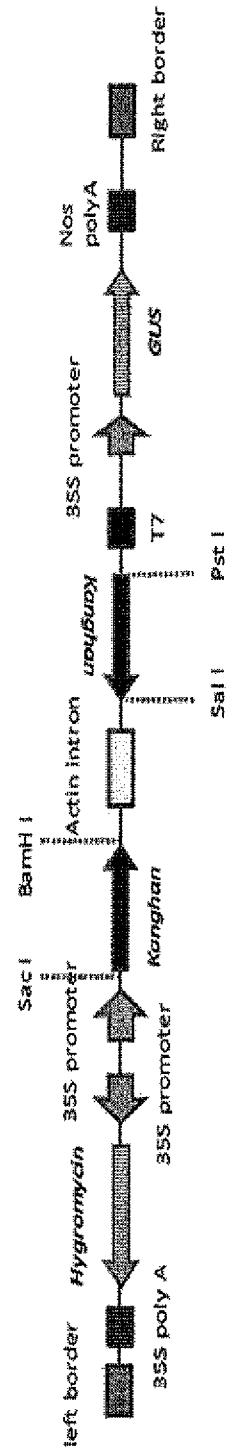

FIG. 16 shows a partial map of an RNAi construct designed to target *Brassica napus* Kanghan genes.

Figure 17:
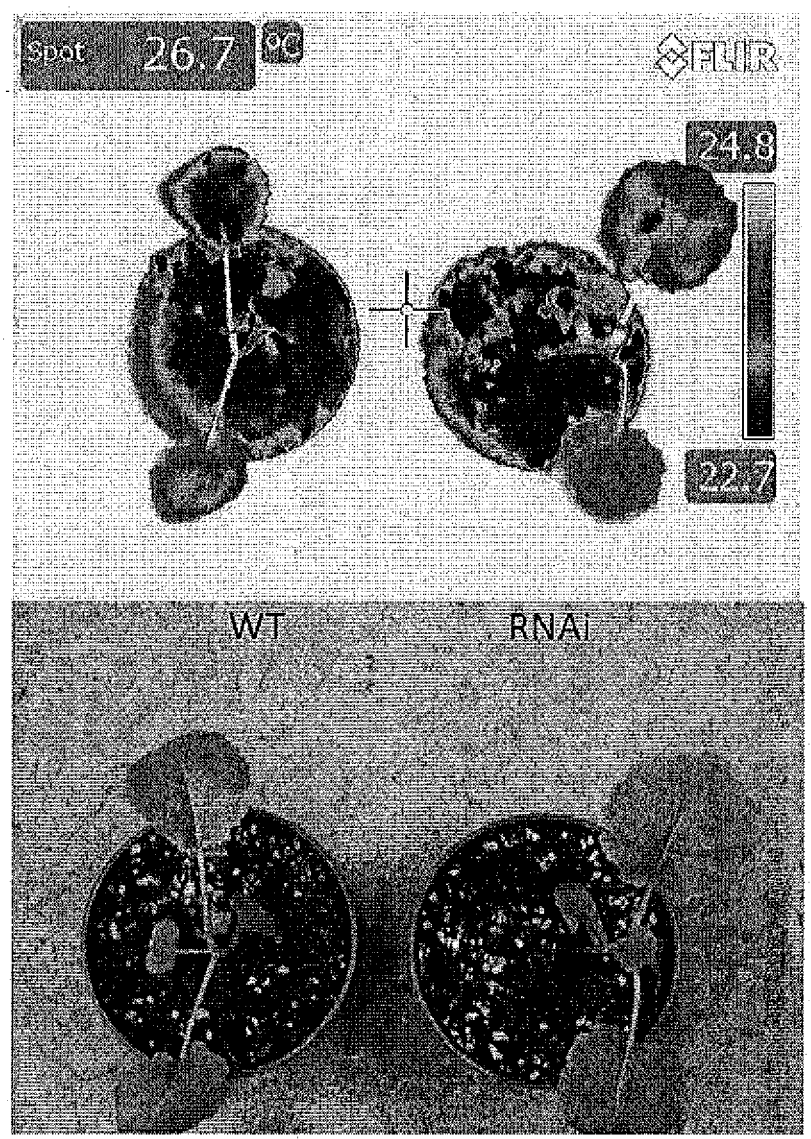

FIG. 17 shows infrared thermal images of a wild-type *Brassica napus* line and a Kanghan RNAi *Brassica napus* line.

Figure 18:
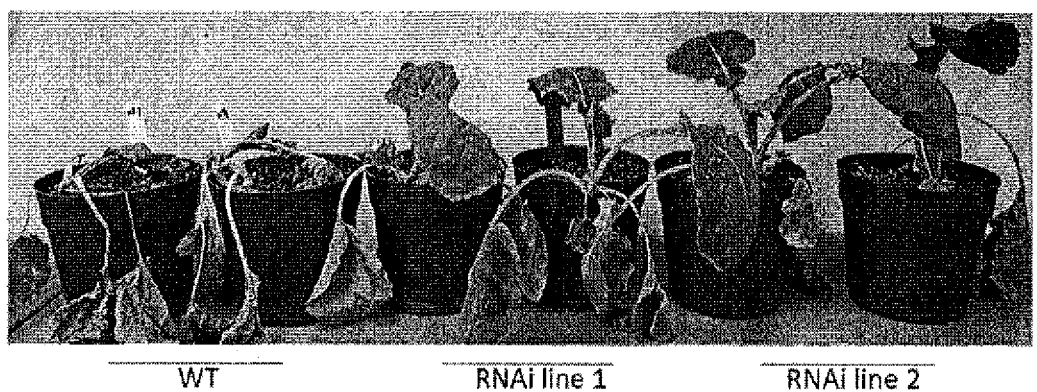

FIG. 18 shows wild-type *Brassica napus* plants and *Brassica napus* plants from two Kanghan RNAi lines that have been subjected to drought treatment.

Figure 19:
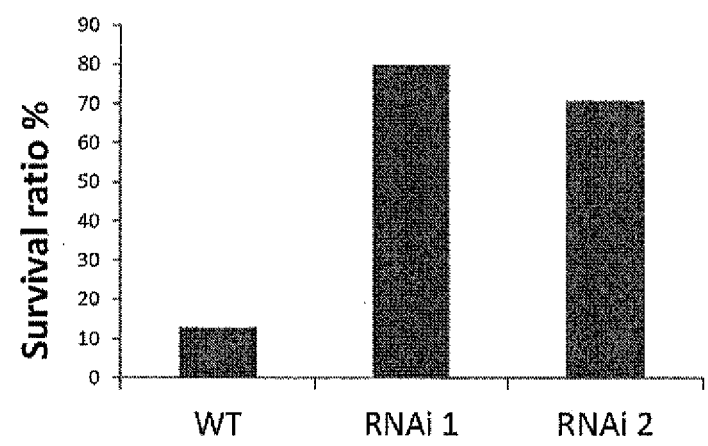

FIG. 19 shows the survival ratio, after 35 days recovery, of wild-type *Brassica napus* plants and *Brassica napus* plants from two RNAi lines that have been subjected to drought treatment.

The following is a list of sequences appearing in this document:

```
SEQ ID NO: 1 is a CDS of the At4g29760 gene
from Arabidopsis;
ATGGCTGAGCGATTATTACAATCTATGTCAAGGGTGGCTGGCCGATGTCA

TCCAGATTGCGTAAAAGCAAGTGATGAGCAAGAAGATTACCATGCATCTC

AAAATGCAGCTTTGGTAGCTGTGAATCTGATTAGCTCTGCAAGGTTAATA

CTGAAACTCGACGCTGAGTTTACTGAGTACTCAGCTCAGTTTTTGATGGA

CAATGCTGGAAAGGAAGACGACCCGGGAGAAGTGGATCAACAACGCAATC

AGGTCACGACCGAAAACTGCCTTCGCTACTTGGCCGAAAACGTTTGGACC

AAGAAGGAAAATGGGCAGGGAGGAATGGATCAACAACGCCCTGTGCTCAC

TGTCAAAGACTGCTTGGAACTTGCTTTTAAAAAAGGGCTGCCGAGAAGAG

AACACTGGGCACATTTGGGATGTACCTTCAAGGCTCCCCCATTTGCTTGT

CAGATACCTCGCGTTCCTGTGAAAGGAGAAGTGGTTGAGGTTAAGACTTT

TGATGAAGCATTCAAGCTGTTGGTGCATCAACCCATTGGAGCAAAACTGC

ATTTGTTCAGTCCGCAGATTGATAATGTTGGAGAGGGAGTTTACAAAGGC

CTCACGACAGGTAATGAAACACACTATGTTGGACTTAGAGATGTGCTAAT

AGCTTCAGTGGAGGAGTTCGAGGGAGATTCTGTTGCTATTGTGAAGATCT

GCTACAAGAAGAAGCTTTCATTTATCAAAGTGTCTTTGAGCGTTAGGTTT

CTCTCAGTAGCACATGATGGTGATAAGTCTAAGTTCATAGCGCCAACAGG

TCTGCTTGTTGACTTCTGTGTCCCGCGCTTATCTATCAACTAA

SEQ ID NO: 2 is a CDS of the At4g29770 gene
from Arabidopsis;
ATGATGGCAATCTCAGAAAAAGGAGTCATGGCAATCTCAGAAAAAGGAGT

CATGGCAACGAAAATTGACAAAAACGGCGTCCTTCGAGAGTTAAGGCGAC

ATTTCACTGAGTTTTCTCTACGCGACGTAGATCTGTGTCTCCGGAGTTCA

TCGCAGATGGAGTCATTGTTAGAATGTTTTGCAATCACGGATGGCAAATG

TCATCCCGATTGCTTAAAAGCAAACAATGAGCAAGAAGATTACGATGCAT

GTCAATCTGCAGCTTTGGTAGCTGTGAGTTTGATTAGCTCTGCACGTGTT

ATCTTCAAGATCGACTCTAAGTATACTGAGTACTCACCTCAGTATTTGGT

GGATAACGTTGGGAAGGAAGAAGTTGAGGGAGAAATGGATCAACCAAGCT

GTCAGTACACTGTCGGAAACCTCCTTAGTTACTTGGTGGAAAACGTTTGG

ACCAAGAAGGAAGTTAGGCAGAGAGAAATGGATCAACAACGCCGTGAGTT

CACTGTCAAAGACTGCTTTGAATTTGCTTTTAAAAAAGGGCTTCCAAGAA

ATGGACATTGGGCGCATGTGGGATGTATATTCCCGGTTCCTCCATTTGCT

TGTCAAATACCTCGCGTTCCCATGAAAGGAGAAGTGATTGAGGCTGCAAA

TGTGAGTGAAGCGTTGAAGCTGGGTATGCAACAACCAGCGGCAGCAAGGC
```

-continued

TGCATTTGTTCAGTCCAGAGTTTGATCTTGTTGGAGAGGGTATTTACGAT

GGCCCGTCAGGTAATGAAACACGATATGTTGGACTTAGAGATGTGCTCAT

GGTTGAGGCGGAGAAGATCAAGGGAGAAACTGTTTTTACTGTGCAGATAT

GCTACAAGAAGAAGACTTCATTTGTCAAAGTGTCTACGAGAAGTATGATT

CTCCCGCTTAATGGTGACGACGAGTCTCAGGTCACAGAGCCAGCATGTCT

ACTTGTTGACTTCTGTATCCCACGTTTTTCTATCAACTAA

SEQ ID NO: 3 is a CDS of the At5g18065 gene
from *Arabidopsis*;
ATGGATATGAATCAGCTATTCATGCAATCTATTGCAAACAGTCGTGGACT

CTGTCATCCAGATTGCGAAAAAGCAAATAATGAGCGTGAAGATTATGATG

CGTCTCAACATGCCGCTATGGTAGCGGTGAATCTGATTAGCTCTGCACGG

GTTATCCTCAAGCTTGATGCTGTGTATACTGAGTACTCAGCTCAGTATTT

GGTGGATAATGCTGGGAAGGAAGACAACCAGGGAGAAATGGATCAACAAA

GCTCTCAGCTCACTCTCCAAAACTTGCTTCAGTATATGGATGAAAATGTC

TGGAATAAGAAGGAAGATGTGCAGGGAGAAAGGGAGCAACCACTCACTGT

CAAAGACTGCCTTGAATGTGCTTTCAAGTAA

SEQ ID NO: 4 is a CDS of the At5g18040 gene
from *Arabidopsis*;
ATGAATATGATTCAGCGATTCATGCAATCTATGGCAAAGACGCGTGGCCT

CTGTCATCCAGATTGCGTAAAAGCAAGTAGTGAGCAAGAAGATTACGATG

CGTCTCAGCTCAGTATTTGGTGGATAATGCTGGGAAGGAAGACGACCAGG

GAGAAATGGATGAACCAAGCTCTCAGTTCACTATCGAAAACTTGCATCAG

TATATGGTGGAAAATGTCTGGAATAAGAGGTAAGATGTGCAGGGAGAGGG

AGCAACCACTCACTGTCAAAGACTGCCTTGAATGTGCTTTCAAGAAAGGG

CTACCGAGAAGAGAACATTGGGCACATGTGGGATGTACATTCAAGGCTCC

CCCATTTGCTTGTCACATACCCCGCGTGCCCATGAAAGGAGAAGTGATTG

AGACTAAGAGTTTGGATGAAGCGTTTAAGCTGTTGATTAAACAACCGGTG

GGTGCAAGACTCCATGTGTTCAGTCCAGACCTTGATAATGTTGGAGAGGG

AGTTTACGAGGGCCTGTCTAGCCTGTCTCGTAAGGAATCACGCTATGTTG

GACTTAGGGATGTCATCATAGTTGCAGTGAATAAGTCCGAGGGAAAAACT

GTTGCTACTGTGAAGATATGTTACAAGAAGAAGACTTCATTTGTCAAAGT

GTGTTTGAGCCGTATGTTTGTCCAGCTTGGTGGTGGCGAGGAGTCTCAGG

TGAAAGAGCCAACAGGTCTGCTTGTTGACTTCTGTATCCCACGCTTATCT

ATCAACTAA

SEQ ID NO: 5 is a CDS of the At1g51670 gene
from *Arabidopsis*;
ATGGCACTCCCTCCCTATGATCCGAATTTCACATTGGCTTTTTCATACGG

TAGACGCGATAATGTCTTTGAGAATGACCCAGAGCACGATGAATCTGCTT

CTGCTGCTATCGTAGCGGTTGAGCTGATAAGCTCTGCACGGCTTGCACTT

AAGCTGGATAGTGTCCGCACTGAGTACTCAGCTCAGTATTTGGTGGACAA

AGCTGGCTCACGCAACCTCAGGCGCAGGCGCAAGCTCACTGTCAAGGACT

GCCTTAACTTTGCGTTAAAGAAAGGCGGCATACCGAGAGCAGAAGATTGG

CCACCTTTGGGATCTGAGTCAAAGACCCCATCATCGTACGAACCTGCTCT

CGTTTCCATGAAAGGAGAAGTGATTGAGCCTAAGGATATGGACGAAGTAC

CTGAGTTGTTGGTGCATCAATCAGCCGTGGGAGCAAAACTGCATGTGTTC

ACTCCACACATTGAACTTCAACAAGACGCAATTTACTTGCCTCGTCAGGT

GAGTATGCGCGCTACGTTGGACTTAGAGATGGGATAG

SEQ ID NO: 6 is a consensus sequence of Kanghan
conserved domain B (100% consensus)
hTVKDChphAhp SEQ ID NO: 7 is a consensus sequence of Kanghan
conserved domain B (80% consensus)
LTVKDCLEhAhKXG (where X is Lys or absent)

SEQ ID NO: 8 is a consensus sequence of Kanghan
conserved domain B (70% consensus)
LTVKDCLEhAFKKG SEQ ID NO: 9 is a consensus sequence of Kanghan
conserved domain C (80% consensus)
VshKGpVlEstshpEsXchhhpQs-huA + LHlFpPph (where
X is any amino acid)

SEQ ID NO: 10 is a consensus sequence of Kanghan
conserved domain C (70% consensus)
VsMKGEVIEspsh-EAhcLllcQPlGA + LHlFoPcl SEQ ID NO: 11 is a consensus sequence of Kanghan
conserved domain A (80% consensus)
cppDYDtStpAAhVAlpLISSARlhLKlDuhhTEYSsQaLhDpsutpp SEQ ID NO: 12 is a consensus sequence of Kanghan
conserved domain A (70% consensus)
spphhpShupscGhCHPDCXKAssEpEDYDASQpAAhVAVsLISSARlhL KLDusaTEYSAQYLVDNAGpccs (where X is any amino
acid or absent)

SEQ ID NO: 13 is a CDS of the At1g48180 gene
from *Arabidopsis*:
ATGGCACTCCCACCCTATGATCCCAATTTCAAATTTGCATTCTCTCTTGG

CACGATTGCGAAACACCAAGATTACGATGAATCTGCTTCTGCTGCTGTTG

TAGCGCTTGATCTGATAAGCTCTGCACGGTTTGCACTTAAGCTGGATAGT

GTCTATACTGAGTACTCTGCTAAGTATGTGGTGGACAATGCTGCTGGCTC

ACACAGTGGGCGCAAGCTCACTGTCAAAGACTGTCTTGAGTTTGCCTTAA

ACAAAGGCGGCATACCGAAAGCAGAAGATTGGCCACGCTTGGGATCTGTG

ATAACGCCCCCATCATCGTATAAACCTGATCTCGTTTCGATGAAAGGACA

AGTGATTGAGCCTCAGACTATTGAGGAAGCATGTGACATGGTGGTGGATC

AACCAGTAGGAGCAAAATTGCATGTGTTCAAGCCACACATTGAACTTCAA

CAAGACGCAAGTGCTATAACTGGCATTTACTGTGGCACGTCAGGTGAGCC

AGCCAGCTATGTCGGACTTAGAGATGCCATCATCGTTGGAGTCGAGAAGA

TCCAAGGGAAGTCTATTGGAACTGTGAAGGTATGGTACAAGAAGTTCATA

TTTCTGAAAGTGGCTATGAGCAGGTGGTTTCAGTTATACTCTCCGGATGG

CACACACACGGGCATAAAGCGAACAGATTACCTTGTTGATTTTGTGTCC

CACGCCTATCCATGGATTAA

SEQ ID NO: 14 is the polypeptide encoded by
SEQ ID NO: 1
MAERLLQSMSRVAGRCHPDCVKASDEQEDYHASQNAALVAVNLISSARLI

LKLDAEFTEYSAQFLMDNAGKEDDPGEVDQQRNQVTTENCLRYLAENVWT

KKENGQGGMDQQRPVLTVKDCLELAFKKGLPRREHWAHLGCTFKAPPFAC

QIPRVPVKGEVVEVKTFDEAFKLLVHQPIGAKLHLFSPQIDNVGEGVYKG

-continued

LTTGNETHYVGLRDVLIASVEEFEGDSVAIVKICYKKKLSFIKVSLSVRF

LSVAHDGDKSKFIAPTGLLVDFCVPRLSIN

SEQ ID NO: 15 is the polypeptide encoded by
SEQ ID NO: 2
MMAISEKGVMAISEKGVMATKIDKNGVLRELRRHFTEFSLRDVDLCLRSS

SQMESLLECFAITDGKCHPDCLKANNEQEDYDACQSAALVAVSLISSARV

IFKIDSKYTEYSPQYLVDNVGKEEVEGEMDQPSCQYTVGNLLSYLVENVW

TKKEVRQREMDQQRREFTVKDCFEFAFKKGLPRNGHWAHVGCIFPVPPFA

CQIPRVPMKGEVIEAANVSEALKLGMQQPAAARLHLFSPEFDLVGEGIYD

GPSGNETRYVGLRDVLMVEAEKIKGETVFTVQICYKKKTSFVKVSTRSMI

LPLNGDDESQVTEPACLLVDFCIPRFSIN

SEQ ID NO: 16 is the polypeptide encoded by
SEQ ID NO: 3
MDMNQLFMQSIANSRGLCHPDCEKANNEREDYDASQHAAMVAVNLISSAR

VILKLDAVYTEYSAQYLVDNAGKEDNQGEMDQQSSQLTLQNLLQYMDENV

WNKKEDVQGEREQPLTVKDCLECAFK

SEQ ID NO: 17 is the polypeptide encoded by
SEQ ID NO: 4
MNMIQRFMQSMAKTRGLCHPDCVKASSEQEDYDASQLSIWWIMLGRKTTR

EKWMNQALSSLSKTCISIWWKMSGIRGKMCREREQPLTVKDCLECAFKKG

LPRREHWAHVGCTFKAPPFACHIPRVPMKGEVIETKSLDEAFKLLIKQPV

GARLHVFSPDLDNVGEGVYEGLSSLSRKESRYVGLRDVIIVAVNKSEGKT

VATVKICYKKKTSFVKVCLSRMFVQLGGGEESQVKEPTGLLVDFCIPRLS

IN

SEQ ID NO: 18 is the polypeptide encoded by
SEQ ID NO: 5
MALPPYDPNFTLAFSYGRRDNVFENDPEHDESASAAIVAVELISSARLAL

KLDSVRTEYSAQYLVDKAGSRNLRRRRKLTVKDCLNFALKKGGIPRAEDW

PPLGSESKTPSSYEPALVSMKGEVIEPKDMDEVPELLVHQSAVGAKLHVF

TPHIELQQDAIYLPRQVSMRATLDLEMG

SEQ ID NO: 19 is the polypeptide encoded by
SEQ ID NO: 13
MALPPYDPNFKFAFSLGTIAKHQDYDESASAAVVALDLISSARFALKLDS

VYTEYSAKYVVDNAAGSHSGRKLTVKDCLEFALNKGGIPKAEDWPRLGSV

ITPPSSYKPDLVSMKGQVIEPQTIEEACDMVVDQPVGAKLHVFKPHIELQ

QDASAITGIYCGTSGEPASYVGLRDAIIVGVEKIQGKSIGTVKVWYKKFI

FLKVAMSRWFQLYSPDGTHTGIKRTDYLVDFCVPRLSMD

SEQ ID NOs: 20 and 21 are a primer pair designed
to target BnaC03g77540D (LOC106364365)
(SEQ ID NO: 20)
TAGATTCTGCTGAGAGAGCCGCTAC (SEQ ID NO: 21)
GGATCCGTCGACGCACCTATGGGTCCATGCTTTAAC SEQ ID NOs: 22 and 23 are a primer pair designed
to target BnaA08g12920D (LOC106424160)
(SEQ ID NO: 22)
TCATCCAGATTGCCAACGAG (SEQ ID NO: 23)
GGATCCGTCGACACGCATCCTCCAGTGTCTTAG SEQ ID NOs: 24 and 25 are a primer pair designed
to target hygromycin
(SEQ ID NO: 24)
TACACAGCCATCGGTCCAGA (SEQ ID NO: 25)
GTAGGAGGGCGTGGATATGTC SEQ ID NOs: 26 and 27 are a primer pair designed
to target BnaA07g02270D
(SEQ ID NO: 26)
CGCTACGAGGCACGTACTCAAT (SEQ ID NO: 27)
CTCGGTCTTCCCCGGTTTC SEQ ID NOs: 28 and 29 are a primer pair designed
to target BnaA08g12920D
(SEQ ID NO: 28)
GCTTAGAGACGTGATCCTGGTAGC (SEQ ID NO: 29)
CCAGTGTGGTGAACATACGGC SEQ ID NOs: 30 and 31 are a primer pair designed
to target BnaC01g07670D
(SEQ ID NO: 30)
GTTTTGTTGGTCTCTTCTCTTTGC (SEQ ID NO: 31)
TTCTTAAGAGGCGTTTCAGATGG SEQ ID NOs: 32 and 33 are a primer pair designed
to target BnaC03g77540D
(SEQ ID NO: 32)
TGATTTGGGTTTTGCCTGATAC (SEQ ID NO: 33)
GAAACAAACCATAAATGAGTTGCC SEQ ID NOs: 34 and 35 are a primer pair designed
to target BnaC03g77550D
(SEQ ID NO: 34)
CATTTGGGATGTGTCGATTGAG (SEQ ID NO: 35)
CCCACGTAGCTTGTTCCGTT SEQ ID NOs: 36 and 37 are a primer pair designed
to target BnaA01g06470D
(SEQ ID NO: 36)
AACACTGTCACGCAGATTGCC (SEQ ID NO: 37)
CTGTCCAGGTTAGCTACCATACGA SEQ ID NOs: 38 and 39 are a primer pair designed
to target BnaC01g08490D
(SEQ ID NO: 38)
CGGTATCCAACTCATTCGAAGG (SEQ ID NO: 39)
TCAAGTATATACTGGGTTGGCTGC

DETAILED DESCRIPTION

In the following detailed description, various non-limiting examples are set out of particular embodiments, together with experimental procedures that may be used to implement a wide variety of modifications and variations in the practice of the present invention. For clarity, a variety of technical terms are used herein in accordance with what is understood to be the commonly understood meaning, as reflected in definitions set out below.

The term "line" refers to a group of plants that displays very little overall variation among individuals sharing that designation. A "line" generally refers to a group of plants that display little or no genetic variation between individuals for at least one trait. Plants within a group of plants that display little or no genetic variation between individuals may also be referred to as having the same genetic background.

A "variety" or "cultivar" includes a line that is used for commercial production. In some aspects, *Brassica* varieties may for example be derived from "doubled haploid" (DH) lines, which refers to a line created by the process of microspore embryogenesis, in which a plant is created from an individual microspore. By this process, lines are created that are homogeneous, i.e. all plants within the line have the same genetic makeup. The original DH plant is referred to as DH1, while subsequent generations are referred to as DH2, DH3 etc. Doubled haploid procedures are well known and have been established for several crops. A procedure for *B. juncea* has been described by Thiagrarajah and Stringham (1993) (A comparison of genetic segregation in traditional and microspore-derived populations of *Brassica juncea* in: L. Czem and Coss. Plant Breeding 111:330-334).

New lines, varieties or plants may be produced by introducing a heritable change in a parent plant. In this context, a "heritable change" is any molecular alteration, typically a genetic change, that is capable of being passed from one generation of plant to the next. This term is intended to include molecular alterations such as, but not limited to, insertions, deletions, point mutations, frame-shift mutations, inversions, rearrangements, and the introduction of transgenes. There is a wide variety of techniques available for introducing heritable changes to plants and plant cells.

Plant "mutagenesis" in the present context is a process in which an agent known to cause alterations in genetic material is applied to plant material, for example the mutagenic agent ethyl methylsulfonate (EMS). A range of molecular techniques such as recombination with foreign or heterologous nucleic acid fragments or gene editing may also be used for mutagenesis. All such methods of introducing nucleic acid sequence changes are included within the term "mutagenesis" as used herein.

Plant "regeneration" involves the selection of cells capable of regeneration (e.g. seeds, microspores, ovules, pollen, vegetative parts) from a selected plant or variety. These cells may optionally be subjected to mutagenesis, following which a plant is developed from the cells using regeneration, fertilization, and/or growing techniques based on the types of cells mutagenized. Applicable regeneration techniques are known to those skilled in the art; see, for example, Armstrong, C. L., and Green, C. E., Planta 165: 322-332 (1985); and Close, K. R., and Ludeman, L. A., Planta Science 52:81-89 (1987).

"Improved characteristics" of a plant means that the characteristics in question are altered in a way that is desirable or beneficial or both in comparison with a reference value or attribute, which in the absence of an express comparator relates to the equivalent characteristic of a wild type strain.

Plant "progeny" means the direct and indirect descendants, offspring and derivatives of a plant or plants and includes the first, second, third and subsequent generations and may be produced by self-crossing, crossing with plants with the same or different genotypes, and may be modified by range of suitable genetic engineering techniques.

Plant "breeding" includes all methods of developing or propagating plants and includes both intra and inter species and intra and inter line crosses as well as all suitable artificial breeding techniques. Desired traits may be transferred to other lines through conventional breeding methods and can also be transferred to other species through inter-specific crossing. Both conventional breeding methods and interspecific crossing methods as well as all other methods of transferring genetic material between plants are included within the concept of "breeding".

"Molecular biological techniques" means all forms of anthropomorphic manipulation of a biological molecules, such as nucleic acid sequences, for example to alter the sequence and expression thereof and includes the insertion, deletion, modification or editing of sequences or sequence fragments and the direct or indirect introduction of new sequences into the genome of an organism, for example by directed or random recombination using suitable vectors and/or techniques.

"Marker-assisted selection" (MAS) refers to the use of molecular markers to assist in phenotypic selection in the context of plant breeding. A wide variety of molecular markers, such as single nucleotide polymorphisms (SNPs), may for example be used in MAS plant breeding, including the application of next-generation sequencing (NGS) technologies.

The term "genetically derived" as used for example in the phrase "an improved characteristic genetically derived from the parent plant or cell" means that the characteristic in question is dictated wholly or in part by an aspect of the genetic makeup of the parent plant or cell, applying for example to progeny of the parent plant or cell that retain the improved characteristic of the parent plant or cell.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. Nucleic acid "constructs" are accordingly recombinant nucleic acids, which have been generally been made by aggregating interoperable component sequencers. The term "recombinant" when made in reference to a protein or a polypeptide refers to a protein or polypeptide molecule which is expressed using a recombinant nucleic acid construct created by means of molecular biological techniques. The term "recombinant" when made in reference to the genetic composition or an organism or cell refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

Recombinant constructs of the invention may include a variety of functional molecular or genomic components, as required for example to mediate gene expression or suppression in a transformed plant. In this context, "DNA regulatory sequences," "control elements," and "regulatory elements," refer to transcriptional and translational control sequences, such as promoters, enhancers, polyadenylation signals, terminators, and protein degradation signals that regulate gene expression. In the context of the present disclosure, "promoter" means a sequence sufficient to direct transcription of a gene when the promoter is operably linked to the gene. The promoter is accordingly the portion of a gene containing DNA sequences that provide for the binding of RNA polymerase and initiation of transcription. Promoter sequences are commonly, but not universally, located in the 5' non-coding regions of a gene. A promoter and a gene are "operably linked" when such sequences are functionally connected so as to permit gene expression mediated by the promoter. The term "operably linked" accordingly indicates that DNA segments are arranged so that they function in concert for their intended purposes, such as initiating transcription in the promoter to proceed through the coding segment of a gene to a terminator portion of the gene. Gene expression may occur in some instances when appropriate molecules (such as transcriptional activator proteins) are bound to the promoter. Expression is the process of conversion of the information of a coding sequence of a gene into mRNA by transcription and subsequently into polypeptide (protein) by translation, as a result of which the protein is said to be expressed. As the term is used herein, a gene or nucleic acid is "expressible" if it is capable of expression under appropriate conditions in a particular host cell.

Promoters may for example be used that provide for preferential gene expression within a specific organ or tissue, or during a specific period of development. For example, promoters may be used that are specific for leaf (Dunsmuir, et al *Nucleic Acids Res*, (1983) 11:4177-4183), root tips (Pokalsky, et al *Nucleic Acids Res*, (1989) 17:4661-4673), fruit (Peat, et al *Plant Mol. Biol*, (1989) 13:639-651; U.S. Pat. No. 4,943,674 issued 24 Jul. 1990; International Patent Publication WO-A 8 809 334; U.S. Pat. No. 5,175,095 issued 29 Dec. 1992; European Patent Application EP-A 0 409 629; and European Patent Application EP-A 0 409 625) embryogenesis (U.S. Pat. No. 5,723,765 issued 3 Mar. 1998 to Oliver et al.), or young flowers (Nilsson et al. 1998). Promoters demonstrating preferential transcriptional activity in plant tissues are, for example, described in European Patent Application EP-A 0 255 378 and International Patent Publication WO-A 9 113 980. Promoters may be identified from genes which have a differential pattern of expression in a specific tissue by screening a tissue of interest, for example, using methods described in U.S. Pat. No. 4,943,674 and European Patent Application EP-A 0255378. The disclosure herein includes examples of this embodiment, showing that plant tissues and organs can be modified by transgenic expression of a Kanghan gene.

An "isolated" nucleic acid or polynucleotide as used herein refers to a component that is removed from its original environment (for example, its natural environment if it is naturally occurring). An isolated nucleic acid or polypeptide may contain less than about 50%, less than about 75%, less than about 90%, less than about 99.9% or less than any integer value between 50 and 99.9% of the cellular or biological components with which it was originally associated. A polynucleotide amplified using PCR so that it is sufficiently distinguishable (on a gel for example) from the rest of the cellular components is, for example, thereby "isolated". The polynucleotides of the invention may be "substantially pure," i.e., having the high degree of isolation as achieved using a purification technique.

In the context of biological molecules "endogenous" refers to a molecule such as a nucleic acid that is naturally found in and/or produced by a given organism or cell. An "endogenous" molecule may also be referred to as a "native" molecule. Conversely, in the context of biological molecules "exogenous" refers to a molecule, such as a nucleic acid, that is not normally or naturally found in and/or produced by a given organism or cell in nature.

As used herein to describe nucleic acid or amino acid sequences the term "heterologous" refers to molecules or portions of molecules, such as DNA sequences, that are artificially introduced into a particular host cell, for example by transformation. Heterologous DNA sequences may for example be introduced into a host cell by transformation. Such heterologous molecules may include sequences derived from the host cell. Heterologous DNA sequences may become integrated into the host cell genome, either as a result of the original transformation of the host cells, or as the result of subsequent recombination events.

Transformation techniques that may be employed include plant cell membrane disruption by electroporation, microinjection and polyethylene glycol based transformation (such as are disclosed in Paszkowski et al. EMBO J. 3:2717 (1984); Fromm et al., Proc. Natl. Acad. Sci. USA 82:5824 (1985); Rogers et al., Methods Enzymol. 118:627 (1986); and in U.S. Pat. Nos. 4,684,611; 4,801,540; 4,743,548 and 5,231,019), biolistic transformation such as DNA particle bombardment (for example as disclosed in Klein, et al., Nature 327: 70 (1987); Gordon-Kamm, et al. "The Plant Cell" 2:603 (1990); and in U.S. Pat. Nos. 4,945,050; 5,015,580; 5,149,655 and 5,466,587); *Agrobacterium*-mediated transformation methods (such as those disclosed in Horsch et al. Science 233: 496 (1984); Fraley et al., Proc. Nat'l Acad. Sci. USA 80:4803 (1983); and U.S. Pat. Nos. 4,940,838 and 5,464,763). Transformation systems adapted for use in *Camelina sativa* are for example described in US Patent Publication 20140223607. Varieties of *Camelina sativa* are for example described in US Patent Publication 20120124693, and the subject of seed samples deposited under ATCC Accession No. PTA-11480. Aspects of the present invention involve altering known plant varieties, such as *Camelina sativa*, to alter endogenous Kanghan genes.

Transformed plant cells may be cultured to regenerate whole plants having the transformed genotype and displaying a desired phenotype, as for example modified by the expression of a heterologous Kanghan gene during growth or development. A variety of plant culture techniques may be used to regenerate whole plants, such as are described in Gamborg and Phillips, "Plant Cell, Tissue and Organ Culture, Fundamental Methods", Springer Berlin, 1995); Evans et al. "Protoplasts Isolation and Culture", Handbook of Plant Cell Culture, Macmillian Publishing Company, New York, 1983; or Binding, "Regeneration of Plants, Plant Protoplasts", CRC Press, Boca Raton, 1985; or in Klee et al., *Ann. Rev. of Plant Phys.* 38:467 (1987).

Various aspects of the present disclosure encompass nucleic acid or amino acid sequences that are homologous to other sequences. As the term is used herein, an amino acid or nucleic acid sequence is "homologous" to another sequence if the two sequences are substantially identical, as defined herein, and the functional activity of the sequences is conserved (as used herein, sequence conservation or identity does not infer evolutionary relatedness). Nucleic acid sequences may also be homologous if they encode substantially identical amino acid sequences, even if the nucleic acid sequences are not themselves substantially identical, for example as a result of the degeneracy of the genetic code.

With reference to biological sequences "substantial homology" or "substantial identity" is meant, in the alternative, a sequence identity of greater than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% up to 100% sequence identity. Homology may refer to nucleic acid or amino acid sequences as the context dictates. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman (1981) *Adv. Appl. Math* 2: 482, the homology alignment algorithm of Needleman and Wunsch (1970) *J Mol. Biol.* 48:443, the search for similarity method of Pearson and Lipman (1988) *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990), *J. Mol. Biol.* 215:403-10 (using the published default settings). Software for performing BLAST analysis may be available through the National Center for Biotechnology Information (NCBI) at their Internet site. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff (1992) *Proc. Natl. Acad. Sci. USA* 89: 10915-10919) alignments (B) of 50, expectation (E) of 10, M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments, nucleotide or amino acid sequences are considered substantially identical if the smallest sum probability in a comparison of the test sequences is less than about 1, less than about 0.1, less than about 0.01, or less than about 0.001.

An alternative indication that two amino acid sequences are substantially identical is that one peptide is specifically immunologically reactive with antibodies that are also specifically immunoreactive against the other peptide. Antibodies are specifically immunoreactive to a peptide if the antibodies bind preferentially to the peptide and do not bind in a significant amount to other proteins present in the sample, so that the preferential binding of the antibody to the peptide is detectable in an immunoassay and distinguishable from non-specific binding to other peptides. Specific immunoreactivity of antibodies to peptides may be assessed using a variety of immunoassay formats, such as solid-phase ELISA immunoassays for selecting monoclonal antibodies specifically immunoreactive with a protein (see Harlow and Lane (1988) *Antibodies, A Laboratory Manual*, Cold Spring Harbor Publications, New York).

An alternative indication that two nucleic acid sequences are substantially identical is that the two sequences hybridize to each other under moderately stringent, or stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

In alternative embodiments, the invention provides nucleic acids, such as isolated or recombinant nucleic acid molecules, comprising the sequence of a Kanghan allele of the invention. Isolated nucleic acids of the invention may include coding sequences of the invention recombined with other sequences, such as cloning vector sequences. Homology to sequences of the invention may be detectable by hybridization with appropriate nucleic acid probes, by PCR techniques with suitable primers or by other techniques. In particular embodiments there are provided nucleic acid probes which may comprise sequences homologous to portions of the alleles of the invention. Further embodiments may involve the use of suitable primer pairs to amplify or detect the presence of a sequence of the invention, for example a sequence that is associated with an abiotic stress response, such as drought or heat resistance.

In alternative embodiments, the invention provides methods for identifying plants, such as *Camelina*, *Brassica* or *Triticum* plants, with a desirable abiotic stress response, such as drought tolerance and/or heat resistance, or a desired genomic characteristic. Methods of the invention may for example involve determining the presence in a genome of particular Kanghan alleles. In particular embodiments the methods may comprise identifying the presence of: a nucleic acid polymorphism associated with one of the identified alleles; or an antigenic determinant associated with one of the alleles. Such a determination may for example be achieved with a range of techniques, such as PCR amplification of the relevant DNA fragment, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variants or wild type forms of that protein.

In selected embodiments, a specific base pair change in a Kanghan allele may for example be used to design protocols for MAS, such as the use of allele-specific probes, markers or PCR primers. For an exemplary summary of allele-specific PCR protocols, see Myakishev et al., 2001, Genome Research 11: 163-169, or Tanhuanpää et al., 1999, Molecular Breeding 4: 543-550. In alternative embodiments, for example, various methods for detecting single nucleotide polymorphisms (SNPs) may be used for identifying Kanghan alleles of the invention. Such methods may for example include TaqMan assays or Molecular Beacon assays (Täpp et al., BioTechniques 28: 732-738), Invader Assays (Mein et al., Genome Research 10: 330-343, 2000) or assays based on single strand conformational polymorphisms (SSCP) (Orita et al., Proc. Natl. Acad. Sci. U.S.A. 86: 2766-2770, 1989).

In alternative embodiments, the invention provides progeny of parent plant lines having altered endogenous or heterologous Kanghan genes, for example progeny of *Camelina sativa* parent line which is the subject of ATCC Accession number PTA-11480. Such progeny may for example be selected to have a desired alteration in an abiotic stress response compared to the parent strain, such as improved drought resistance or heat tolerance.

In alternative embodiments, a plant seed is provided, such as an *Arabidopsis, Camelina, Triticum* or *Brassica* seed. In alternative embodiments, genetically stable plants are provided, such as plants of the genus *Arabidopsis, Camelina, Triticum* or *Brassica*. In further alternative embodiments the invention provides processes of producing genetically stable plants, such as *Arabidopsis, Camelina, Triticum* or *Brassica* plants, for example plants having a desired alteration in an abiotic stress response compared to a reference strain that does not have a particular alteration in a Kanghan gene, such as improved drought resistance or heat tolerance.

In various aspects, the invention involves the modulation of the number of copies of an expressible Kanghan coding sequence in a plant genome. By "expressible" it is meant that the primary structure, i.e. sequence, of the coding sequence indicates that the sequence encodes an active protein. Expressible coding sequences may nevertheless not be expressed as an active protein in a particular cell, for example due to gene silencing. This 'gene silencing' may for example take place by various mechanisms of homologous transgene inactivation or epigenetic silencing in vivo. Homologous transgene inactivation and epigenetic silencing in transgenic plants has been described in plants where a transgene has been inserted in the sense orientation, with the result that both the gene and the transgene are down-regulated (Napoli et al., 1990 Plant Cell 2: 279-289; Rajeevkum et al., 2015 Front Plant Sci 6:693). In the present invention, the expressible coding sequences in a genome may accordingly not all be expressed in a particular cell, and may in some embodiments result in suppression of Kanghan gene expression.

In other aspects, reduction of Kanghan gene expression may include the reduction, including the suppression or elimination (aka knockout), of expression of a nucleic acid sequence that encodes a Kanghan protein, such as a nucleic acid sequence of the invention. By elimination of expression, it is meant herein that a functional amino acid sequence encoded by the nucleic acid sequence is not produced at a detectable level. By suppression of expression, it is meant herein that a functional polypeptide encoded by the nucleic acid sequence is produced at a reduced level relative to the wild type level of expression of the polypeptide. Reduction of Kanghan expression may include the elimination of transcription of a nucleic acid sequence that encodes a Kanghan protein, such as a sequence of the invention encoding a Kanghan protein. By elimination of transcription it is meant herein that the mRNA sequence encoded by the nucleic acid sequence is not transcribed at detectable levels. Reduction of Kanghan activity may also include the production of a truncated amino acid sequence from a nucleic acid sequence that encodes a Kanghan protein, meaning that the amino acid sequence encoded by the nucleic acid sequence is missing one or more amino acids of the functional amino acid sequence encoded by a wild type nucleic acid sequence. In addition, reduction of Kanghan activity may include the production of a variant Kanghan amino acid sequence, meaning that the amino acid sequence has one or more amino acids that are different from the amino acid sequence encoded by a wild type nucleic acid sequence. A variety of mutations may be introduced into a nucleic acid sequence for the purpose of reducing Kanghan activity, such as frame-shift mutations, introduction of premature stop codon(s), substitutions and deletions. For example, mutations in coding sequences may be made so as to introduce substitutions within functional motifs or conserved domains in a Kanghan protein, such as conserved Kanghan protein domains A, B or C.

In an alternative aspect, the down-regulation of Kanghan genes may be used to alter a plant response to abiotic stress, for example to enhance drought tolerance. Such down-regulation may be tissue-specific. For example, anti-sense oligonucleotides may be expressed to down-regulate expression of Kanghan genes. The expression of such anti-sense constructs may be made to be tissue-specific by operably linking anti-sense encoding sequences to tissue-specific promoters. Anti-sense oligonucleotides, including anti-sense RNA molecules and anti-sense DNA molecules, act to block the translation of mRNA by binding to targeted mRNA and inhibiting protein translation from the bound mRNA. For example, anti-sense oligonucleotides complementary to regions of a DNA sequence encoding a Kanghan protein may be expressed in transformed plant cells during development to down-regulate the expression of the Kanghan gene. Alternative methods of down-regulating Kanghan gene expression may include the use of ribozymes or other enzymatic RNA molecules (such as hammerhead RNA structures) that are capable of catalyzing the cleavage of RNA (as disclosed in U.S. Pat. Nos. 4,987,071 and 5,591,610).

Aspects of the invention involve the use of gene editing to alter Kanghan gene sequences. For example, CRISPR-Cas system(s) (e.g., single or multiplexed) can be used to perform plant gene or genome interrogation or editing or manipulation. Kanghan genes may for example be edited for functional investigation and/or selection and/or interrogation and/or comparison and/or manipulation and/or transformation of plant Kanghan genes. This editing may be carried out so as to create, identify, develop, optimize, or confer trait(s) or characteristic(s) to plant(s) or to transform a plant genome, for example to alter an abiotic stress response in a plant, such as a drought or heat tolerance. Gene editing can in this way be used to provide improved production of plants, new plants with new combinations of traits or characteristics or new plants with enhanced traits. Such CRISPR-Cas system(s) can for example be used in Site- Directed Integration (SDI) or Gene Editing (GE) or any Near Reverse Breeding (NRB) or Reverse Breeding (RB) techniques (see the University of Arizona website "CRISPR-PLANT" http://www.genome.arizona.edu/crispr/). Embodiments of the invention can be used in genome editing in plants alone or in combination with other molecular biological techniques, such as RNAi or similar genome editing techniques (see, e.g., Nekrasov, Plant Methods 2013, 9:39; Brooks, Plant Physiology September 2014 pp 114.247577; Shan, Nature Biotechnology 31, 686-688 (2013); Feng, Cell Research (2013) 23:1229-1232; Xie, Mol Plant. 2013 November; 6(6):1975-83; Xu, Rice 2014, 7:5 (2014); Caliando et al, Nature Communications 6:6989; U.S. Pat. Nos. 6,603,061; 7,868,149; US 2009/0100536; Morrell et al., Nat Rev Genet. 2011 Dec. 29; 13(2):85-96). Protocols for targeted plant genome editing via CRISPR/Cas9 are also available in volume 1284 of the series Methods in Molecular Biology pp 239-255 10 Feb. 2015.

In some embodiments, the invention provides new Kanghan polypeptide sequences, which may be produced from wild type Kanghan proteins by a variety of molecular biological techniques. It is well known in the art that some modifications and changes can be made in the structure of a polypeptide without substantially altering the biological function of that peptide, to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made were the hydrophilicity value of the residues is significantly different, e.g. differing by more than 2.0.

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made were the hydropathic index of the residues is significantly different, e.g. differing by more than 2.0.

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made were the residues do not fall into the same class, for example substitution of a basic amino acid for a neutral or non-polar amino acid.

Example 1: *Arabidopsis* Kanghan Genes

This Example illustrates that drought tolerance in *Arabidopsis* is conferred by novel QTLs located on three different chromosomes. These genes were identified in an extremely drought tolerant *Arabidopsis* ecotype, designated herein as #95. The #95 ecotype was isolated during a series of drought treatment experiments, and assessed as follows.

In one assay, 36 plants of ecotype Col and 36 plants of ecotype #95 were used for drought sensitivity testing. At the outset, soil for each pot was dried and weighed to ensure that each pot had the same amount of soil, after which water was added to maintain moisture. Seeds from Col and #95 were first germinated, then sown one seedling per pot separately. The plants were grown in a controlled environment under long-day conditions (16-h-light/8-h-dark cycle) at 23° C., light intensity of 50 µmol m$^{-2}$ s$^{-1}$ and 70% relative humidity (rH). Watering was stopped for both Col and #95 plants three weeks after germination, and all pots were then weighed again, and additional water was supplied to keep every pot at the same weight. Thereafter, drought treatment was initiated and survival days were recorded for both ecotypes. After a period of 15 days without watering, all 36 plants of ecotype Col had died. In contrast, the plants of ecotype #95 retained considerable vigor, and fully recovered to maturity when water supply was resumed.

Figure 1:
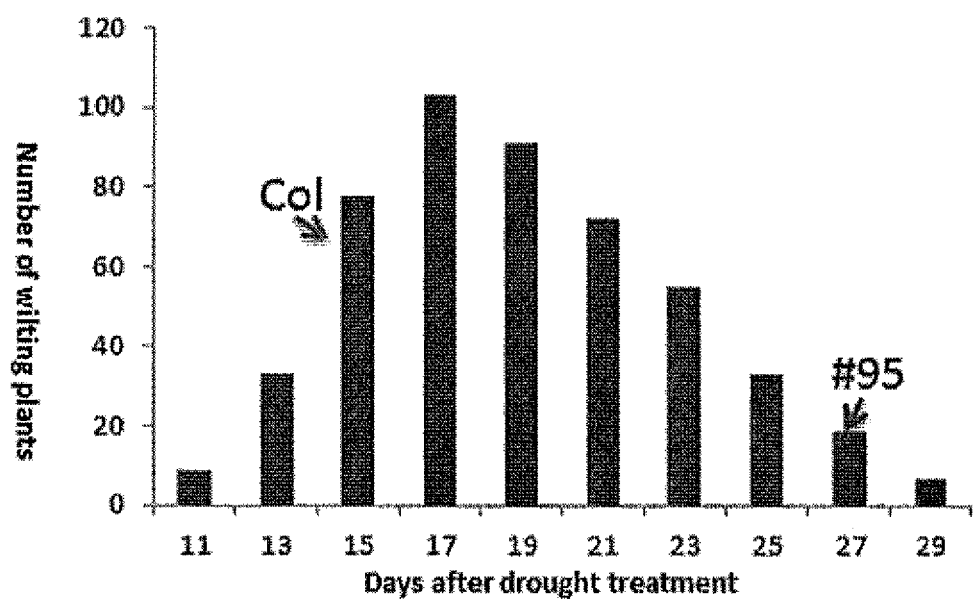
FIG. 1 is a graph showing segregation of a drought tolerance trait from 500 F2 individual lines, calculated by the survival days after drought treatment (cessation of watering). The survival in days of Col and #95 plants are marked by arrows and legends.

The extreme drought tolerance *Arabidopsis* ecotype #95 was particularly evident after withdrawing water for 38 days. Plants of the ecotype Col were all severely wilted due to drought. Ecotype #95, in contrast, still exhibited clear vigor. The F1 progeny between Col and #95 were also sensitive to drought, indicating the recessive nature of the #95 drought resistant trait. In one assay, 27 days after water was withdrawn, the plants were segregated into two groups, those that had died, and those that maintained vigor and were recoverable to full maturity when watering was resumed. In alternative drought tolerance tests of F2 progeny derived from a cross between Col and #95, segregation of F2 population plants after drought treatment (50 days after water withdrawal) was much lower than 3:1. This segregation is consistent with the involvement of major QTL in controlling the drought tolerance trait. FIG. 1 is graph illustrating the drought tolerance diversity of the F2 generation of these *Arabidopsis* plants (col×#95). Segregation of the drought tolerance trait from 500 F2 individual lines was calculated by the survival days after drought treatment (cessation of watering). In FIG. 1, the survival in days of Col and #95 plants are marked by arrows with legends. The normal distribution for the phenotype of F2 drought tolerance indicates that several QTLs govern the drought tolerance trait.

Map based cloning through crossing with ecotype Col, revealed that the drought-related trait was governed by three major QTLs distributed on three different chromosomes. To delineate the underlying genetic components, an F1 generation was developed from the seeds of a cross between Col and #95. The F1 seeds were then used to develop a large F2 population of 5000 lines. The F2 populations showed significant segregation of the drought tolerance trait, with some plants showing significant drought tolerance, and others showing no drought tolerance, which indicated that the drought tolerance trait of #95 was controlled by several QTLs.

A fine mapping of the genes was further pursued using 500 lines of this population from which 20 extremely drought tolerant individuals and 20 extremely drought sensitive individuals were selected to conduct a Bulk Segregate Analysis (BSA) with 106 molecular markers which cover all 5 chromosomes of *Arabidopsis*. Based on this analysis, three major QTLs distributed on three different chromosomes were identified. Specifically, QTL's were identified on chromosomes 1, 4 and 5 of the *Arabidopsis* genome. The contribution rates of these 3 loci to the observed drought tolerance trait were 13.8%, 29.3%, 37.7%, respectively, explaining in the aggregate more than 80% of the drought tolerance variation between ecotype #95 and Col.

Fine mapping was first focused on loci on Chr.4 and Chr.5, which was carried out using 700 extremely drought tolerant individuals from a total of 5000 F2 plants. The candidate genes were narrowed down to two regions of 540 kb on Chr.4 and 189 kb on Chr.5. Single nucleotide polymorphism (SNP) and insertion/deletion (In/del) analysis, as well as expression level analysis based on the TAIR database, was carried out for all of the genes identified in these two regions on Chr.4 and 5.

The full genome sequence of ecotype #95 was compared with the full genome sequence of *Arabidopsis* ecotype Columbia (ecotype Col). The three major QTL's associated with drought tolerance on Chr. 1, Chr. 4 and Chr. 5 of ecotype #95 were revealed to harbor members of a protein coding gene family: At1g51670, At4g29760, At4g29770, At5g18065 and At5g18040. An additional member of the gene family was recognized by sequence similarity: At1g48180. This gene family is designated herein as the Kanghan gene family, the first 5 of which have very strong roles in drought tolerance (a GenBank database accession number for a protein encoded by each of the native *Arabidopsis* genes is given after the gene name in brackets): Kanghan1 (At5g18040; NP_197305.1), Kanghan2 (At4g29770; NP_001154277.1), Kanghan3 (At1g51670; NP_175578.2), Kanghan4 (At4g29760; NP_194705.1), Kanghan5 (At5g18065; NP_680172.2), Kanghan6 (At1g48180; NP_175252.1).

Analysis of the genomic sequence of Ecotype #95 reveals that mutations within Kanghan family genes are associated with drought tolerance. Specifically, in ecotype #95, all 5 members of the Kanghan family strongly associated with drought tolerance have dramatic mutations. Specifically, four members of the Kanghan gene family (At4g29770, At5g18065, At5g18040 and At1g51670) contain a premature stop codon (see FIG. 2), which is indicative of loss-of-function mutations (null) in ecotype #95 compared to the Col variety. A fifth member of the Kanghan gene family, At4g29760, does not contain a premature stop codon, but 5 amino acid substitutions occur in the coding region of this gene. Among the five Kanghan genes strongly associated with drought tolerance, At5g18040, At4g29770 and At1g51670 are much more highly expressed (over 10 times) in both Col and #95 compared to At5g18065 and At4g29760, suggesting that At5g18040, At4g29770 and At1g51670 may in some circumstances contribute more than the other two genes to drought tolerance trait.

Example 2: Reversing Drought Resistance

To further illustrate the role of the Kanghan genes in drought tolerance, two full length Kanghan genes (AT5g18040 and At4g29770) from *Arabidopsis* ecotype Col were used to transform *Arabidopsis* ecotype #95, including at least 2 kb 5'UTR, 1 kb 3'UTR and CDS. The transformants lost their drought resistance, confirming that the modulation of Kanghan gene expression plays a dramatic role in drought resistance.

A further illustration of the dramatic effect of Kanghan genes on drought tolerance was provided by introducing five Kanghan gene alleles from ecotype #95 into ecotype Columbia (Col) by crossing and molecular marker based selection, generation by generation. The $7^{th}$ generation of backcrossed lines was used for self-crossing to provide homozygous plants which contained the five Kanghan gene alleles from #95 strongly associated with drought tolerance. These homozygous plants were subjected to drought treatment. The result was that introduction of the #95 Kanghan gene alleles rendered ecotype Columbia drastically enhanced in its drought tolerance traits.

A further illustration of the effect of Kanghan genes on abiotic stress response was provided by measuring the canopy temperatures of Col, #95 and the backcrossed lines bearing the Kanghan alleles. Increased canopy temperature was clearly evident in #95 plants and backcrossed lines, when compared with Col ecotype plants. Further, subjecting seedlings of #95 and Col to heat treatment at 45° C. confirmed heat sensitivity in ecotype #95.

As this Example illustrates, functional expression of Kanghan gene family proteins plays a positive role in heat tolerance, and a negative role in drought tolerance. The invention accordingly provides a variety of avenues for modulating abiotic stress response in plants.

In some embodiments, this involves balancing Kanghan gene expression to achieve a desired phenotype of abiotic stress response, for example balancing drought and heat tolerance.

The negative role of the Kanghan family of genes in drought tolerance serves as a basis for improving plant drought tolerance by down-regulating or silencing members of the Kanghan gene family. This may for example be achieved through a wide variety of techniques, including mutagenesis (TILLing) or targeted gene editing, as discussed above.

Example 3: Kanghan Sequence Similarity and Protein Domains

TABLE 1

BLAST alignments of Kanghan proteins, with AT4G29770 as reference sequence.

| Sequence Accession | Gene | Percent Identities | Percent Positives | Length of Alignment | Mismatches | Gaps |
| --- | --- | --- | --- | --- | --- | --- |
| NP_001154277.1 | AT4G29770 | 100 | 100 | 329 | 0 | 0 |
| NP_194705.1 | AT4G29760 | 60.432 | 73.38 | 278 | 108 | 2 |
| NP_197305.1 | AT5G18040 | 48.227 | 60.99 | 282 | 112 | 4 |

TABLE 1-continued

BLAST alignments of Kanghan proteins, with AT4G29770 as reference sequence.

| Sequence Accession | Gene | Percent Identities | Percent Positives | Length of Alignment | Mismatches | Gaps |
|---|---|---|---|---|---|---|
| NP_680172.2 | AT5G18065 | 63.415 | 73.98 | 123 | 42 | 1 |
| NP_175252.1 | AT1G48180 | 35.907 | 50.19 | 259 | 120 | 5 |
| NP_175578.2 | AT1G51670 | 36.628 | 49.42 | 172 | 70 | 4 |

TABLE 2

Continuation of BLAST alignments of Kanghan proteins, with AT4G29770 as reference sequence.

| Sequence Accession | Query Start | Query End | Subject Start | Subject End | E Value | Max Score |
|---|---|---|---|---|---|---|
| NP_001154277.1 | 1 | 329 | 1 | 329 | 0 | 685 |
| NP_194705.1 | 54 | 329 | 3 | 280 | 2.53E−115 | 347 |
| NP_197305.1 | 51 | 329 | 2 | 252 | 1.06E−80 | 258 |
| NP_680172.2 | 56 | 178 | 7 | 126 | 1.16E−42 | 155 |
| NP_175252.1 | 77 | 329 | 21 | 239 | 1.45E−39 | 150 |
| NP_175578.2 | 80 | 249 | 28 | 162 | 8.24E−20 | 95.1 |

TABLE 3

BLAST alignments of Kanghan proteins, with AT1G51670 as reference sequence.

| Sequence Accession | Gene | Percent Identities | Percent Positives | Length of Alignment | Mismatches | Gaps |
|---|---|---|---|---|---|---|
| NP_175578.2 | AT1G51670 | 100 | 100 | 178 | 0 | 0 |
| NP_175252.1 | AT1G48180 | 65.625 | 76.25 | 160 | 48 | 3 |
| NP_194705.1 | AT4G29760 | 43.407 | 53.85 | 182 | 62 | 7 |
| NP_001154277.1 | AT4G29770 | 36.628 | 49.42 | 172 | 70 | 4 |
| NP_197305.1 | AT5G18040 | 45.833 | 60.42 | 96 | 47 | 4 |
| NP_680172.2 | AT5G18065 | 43.75 | 51.04 | 96 | 21 | 2 |

TABLE 4

Continuation of BLAST alignments of Kanghan proteins, with AT1G51670 as reference sequence.

| Sequence Accession | Query Start | Query End | Subject Start | Subject End | E Value | Max Score |
|---|---|---|---|---|---|---|
| NP_175578.2 | 1 | 178 | 1 | 178 | 6.95E−127 | 366 |
| NP_175252.1 | 1 | 160 | 1 | 153 | 5.32E−61 | 201 |
| NP_194705.1 | 20 | 162 | 19 | 198 | 6.40E−25 | 108 |
| NP_001154277.1 | 28 | 162 | 80 | 249 | 4.46E−20 | 95.1 |
| NP_197305.1 | 69 | 162 | 77 | 169 | 9.09E−13 | 73.6 |
| NP_680172.2 | 28 | 90 | 31 | 126 | 1.36E−09 | 63.2 |

As set out in the tables above, which alternatively set out BLAST alignments with reference sequences that are the most divergent of the Kanghan genes (AT4G29770 and AT1G51670) the Kanghan gene family may be defined as including genes that encode proteins, that when optimally aligned, have at least 35% identity and/or at least 49% positive alignments, over a length of at least 90 amino acids, with BLOSUM or PAM substitution matrix, with gaps permitted.

This Example further illustrates the existence of conserved protein domains encoded by Kanghan family genes, as depicted in FIGS. 3 through 7.

Conserved domain A is close to the amino end of the proteins, and as shown in FIGS. 4 and 5, comprises a region that may be defined as having a reasonably high degree of consensus (80%) to the following sequence: cppDYDtStpAAhVAlpLISSAR1hLK1DuhhTEYSsQaLh-Dpsutpp (SEQ ID NO: 11). Alternatively, at a slightly reduced level of consensus, conserved domain A may be defined as comprising a region that is defined as having a reasonably high degree of consensus (70%) to the following sequence: spphhp ShupscGhCHPDC-KAssEpEDYDAS-QpAAhVAVsLISSAR1hLKLDusaTEYSAQYLVDNAGp-ccs (SEQ ID NO: 12).

Conserved domain B, as shown in FIGS. 4 and 6, comprises a region that may be defined as having a high degree of consensus (100%) to the following sequence: hTVKD-ChphAhp (SEQ ID NO: 6). Alternatively, at a reduced level of consensus, conserved domain B may be defined as comprising a region that is defined as having at least 80% identity to the following sequence: LTVKDCLEhAhK-G (SEQ ID NO: 7). Alternatively, at a further reduced level of consensus, conserved domain B may be defined as comprising a region that is defined as having at least 70% identity to the following sequence: LTVKDCLEhAFKKG (SEQ ID NO: 8).

Conserved domain C, as shown in FIGS. 4 and 7, comprises a region that may be defined as having at least 80% identity to the following sequence: VshKGpVlEstshpEs.chhhpQs-huA+LH1FpPph (SEQ ID NO: 9). Alternatively, at a reduced level of consensus, conserved domain C may be defined as comprising a region that is defined as having at least 70% identity to the following sequence: VsMKGEV-IEspsh-EAhcL11cQP-lGA+LH1FoPc1 (SEQ ID NO: 10). FIGS. 5, 6 and 7 illustrate consensus sequences using a sequence logo, which is a graphical representation of an amino acid or nucleic acid multiple sequence alignment (CLUSTL W). Each logo consists of stacks of symbols, one stack for each position in the sequence. The overall height of the stack indicates the sequence conservation at that position, while the height of symbols within the stack indicates the relative frequency of each amino or nucleic acid at that position. The width of the stack is proportional to the fraction of valid symbols in that position—positions with many gaps have thin stacks (Crooks et al., Genome Research, 14:1188-1190, (2004); Schneider and Stephens, 1990, Nucleic Acids Res. 18:6097-6100). Shading of the weblogo images reflects amino acid chemistry (AA).

Figure 2:
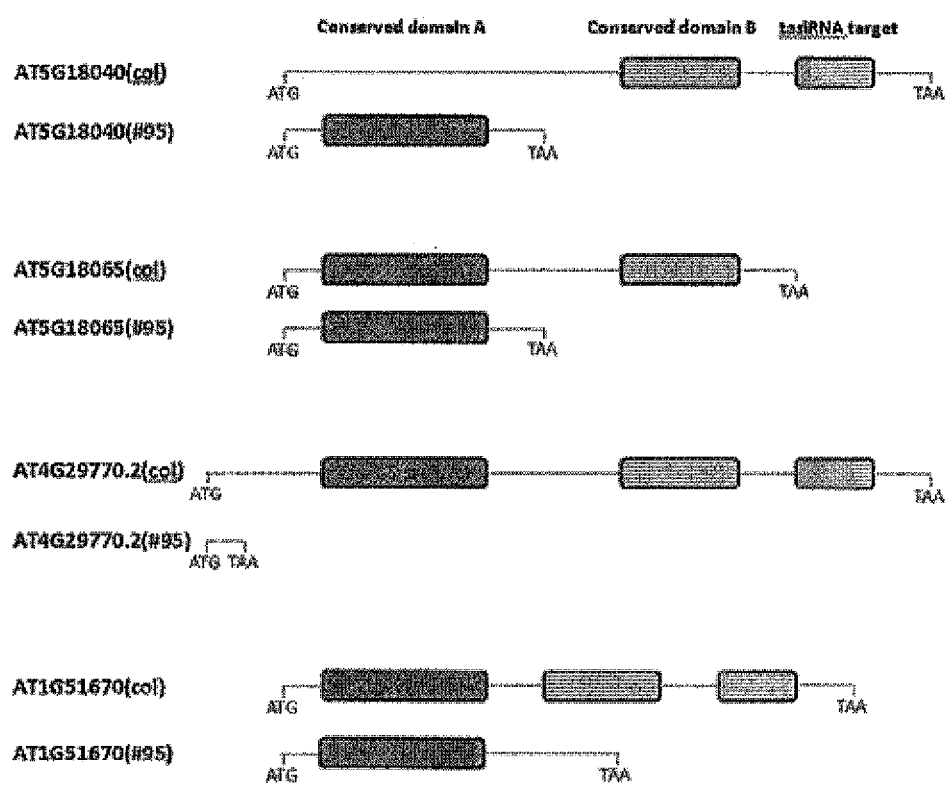
FIG. 2 is a diagram depicting the gene structure of four members of the Kanghan gene family in *Arabidopsis* ecotype Col and #95. The locations of premature stop codons are indicated as TAA.

Conserved domain A is absent in Kanghan1 (At5g18040) in Columbia (Col) due to an 82 bp deletion compared to the orthologous gene in other species of *Arabidopsis*. As shown in FIG. 2, the At5g18040 gene in Ecotype #95 contains conserved domain A, before the premature stop codon, so that the existence of this domain on its own does not appear to confer drought tolerance.

Conserved domain B is relatively highly conserved in all members of Kanghan gene family in Columbia. In contrast, the premature stop codons of Kanghan1, Kanghan2, Kanghan3, and Kanghan5 cause the loss of conserved domain B in #95. Accordingly, this absence of this domain is closely associated with the drought tolerance trait.

Conserved domain C and the tasi-RNA target site are not present in Kanghan5 (At5g18065) in both Columbia and #95.

BLAST searching reveals that Kanghan family genes are widely distributed in Brassicaceae, in addition to the six Kanghan genes in *Arabidopsis thaliana*, there are also 5 members in *Arabidopsis lyrata*, 6 members in *Caspsella rubella*, 5 members in *Brassica rapa*, 11 members in *Brassica napus*, 3 members in *Eutrema salsugineum*, 1 member in Thellugiella *parvula*, and at least 24 members in *Camelina sativa*. Most of these Kanghan genes include all three conserved domains, and all of them contain conserved domain B.

TABLE 5

BLASTP search results identifying plant Kanghan proteins based on sequence similarity to the protein encoded by AT4G29770.

| Seq | Gene | Identities | Positives | Length of Alignment |
|---|---|---|---|---|
| NP_001154277.1 | AT4G29770 | 100 | 100 | 329 |
| CAB43652.1 | hypothetical protein [*Arabidopsis thaliana*] | 100 | 100 | 282 |
| NP_567833.1 | target of trans acting-siR480/255 [*Arabidopsis thaliana*] | 100 | 100 | 277 |
| XP_002869410.1 | hypothetical protein ARALYDRAFT_491783 [*Arabidopsis lyrata* subsp. *lyrata*] | 85.56 | 89.89 | 277 |
| XP_006293511.1 | hypothetical protein CARUB_v10023817mg [*Capsella rubella*] | 73.188 | 83.33 | 276 |
| XP_010447809.1 | PREDICTED: uncharacterized protein LOC104730345 [*Camelina sativa*] | 71.326 | 82.8 | 279 |
| XP_010438266.1 | PREDICTED: uncharacterized protein LOC104721886 [*Camelina sativa*] | 70.504 | 82.37 | 278 |
| XP_010433066.1 | PREDICTED: uncharacterized protein LOC104717221 [*Camelina sativa*] | 70.922 | 81.56 | 282 |
| XP_010447810.1 | PREDICTED: uncharacterized protein LOC104730347 [*Camelina sativa*] | 68.1 | 79.57 | 279 |
| XP_010436343.1 | PREDICTED: uncharacterized protein LOC104720070 [*Camelina sativa*] | 74.194 | 82.66 | 248 |
| XP_002869411.1 | predicted protein [*Arabidopsis lyrata* subsp. *lyrata*] | 65.233 | 76.34 | 279 |
| XP_010441644.1 | PREDICTED: uncharacterized protein LOC104724792 [*Camelina sativa*] | 66.791 | 78.36 | 268 |
| XP_010494756.1 | PREDICTED: uncharacterized protein LOC104771851 [*Camelina sativa*] | 66.045 | 77.99 | 268 |

TABLE 5-continued

BLASTP search results identifying plant Kanghan proteins based on sequence similarity to the protein encoded by AT4G29770.

| Seq | Gene | Identities | Positives | Length of Alignment |
|---|---|---|---|---|
| XP_010451117.1 | PREDICTED: uncharacterized protein LOC104733215 [*Camelina sativa*] | 65.108 | 76.26 | 278 |
| XP_010441643.1 | PREDICTED: uncharacterized protein LOC104724791 [*Camelina sativa*] | 62.816 | 76.9 | 277 |
| XP_002871796.1 | predicted protein [*Arabidopsis lyrata* subsp. *lyrata*] | 64.234 | 74.09 | 274 |
| XP_006280936.1 | hypothetical protein CARUB_v10026934mg [*Capsella rubella*] | 66.415 | 77.36 | 265 |
| XP_010438262.1 | PREDICTED: uncharacterized protein LOC104721884 [*Camelina sativa*] | 65.556 | 74.81 | 270 |
| XP_002871797.1 | predicted protein [*Arabidopsis lyrata* subsp. *lyrata*] | 63.296 | 72.28 | 267 |
| NP_194705.1 | AT4G29760 | 60.432 | 73.38 | 278 |
| XP_006413298.1 | hypothetical protein EUTSA_v10026005mg [*Eutrema salsugineum*] | 54.373 | 70.72 | 263 |
| XP_013601305.1 | PREDICTED: uncharacterized protein LOC106308720 [*Brassica oleracea* var. *oleracea*] | 53.409 | 70.45 | 264 |
| XP_013720359.1 | PREDICTED: uncharacterized protein LOC106424160 [*Brassica napus*] | 54.444 | 67.78 | 270 |
| XP_006412791.1 | hypothetical protein EUTSA_v10027444mg [*Eutrema salsugineum*] | 54.412 | 68.75 | 272 |
| XP_013628081.1 | PREDICTED: uncharacterized protein LOC106334325 [*Brassica oleracea* var. *oleracea*] | 54.851 | 68.28 | 268 |
| XP_010436344.1 | PREDICTED: uncharacterized protein LOC104720071 [*Camelina sativa*] | 62.673 | 70.05 | 217 |
| XP_009108974.1 | PREDICTED: uncharacterized protein LOC103834660 isoform X2 [*Brassica rapa*] | 53.333 | 66.67 | 270 |
| XP_010438269.1 | PREDICTED: uncharacterized protein LOC104721889 [*Camelina sativa*] | 50.158 | 57.41 | 317 |
| CDY23253.1 | BnaA08g12930D [*Brassica napus*] | 52.239 | 68.28 | 268 |
| XP_006294905.1 | hypothetical protein CARUB_v10023956mg [*Capsella rubella*] | 49.811 | 63.77 | 265 |
| XP_009108973.1 | PREDICTED: uncharacterized protein LOC103834660 isoform X1 [*Brassica rapa*] | 51.493 | 67.16 | 268 |
| XP_009127652.1 | PREDICTED: uncharacterized protein LOC103852500 [*Brassica rapa*] | 51.515 | 68.56 | 264 |
| XP_013659423.1 | PREDICTED: uncharacterized protein LOC106364376 [*Brassica napus*] | 52.453 | 65.28 | 265 |
| NP_197305.1 | AT5G189040 | 48.227 | 60.99 | 282 |
| CDX68686.1 | BnaC01g07670D [*Brassica napus*] | 53.815 | 70.28 | 249 |
| XP_013668007.1 | PREDICTED: uncharacterized protein LOC106372351 [*Brassica napus*] | 50 | 67.42 | 264 |
| XP_013720313.1 | PREDICTED: uncharacterized protein LOC106424116 isoform X2 [*Brassica napus*] | 50.562 | 66.29 | 267 |
| AAM64385.1 | unknown [*Arabidopsis thaliana*] | 49.451 | 60.81 | 273 |
| XP_013720312.1 | PREDICTED: uncharacterized protein LOC106424116 isoform X1 [*Brassica napus*] | 50.562 | 66.29 | 267 |
| XP_013659411.1 | PREDICTED: uncharacterized protein LOC106364365 [*Brassica napus*] | 52 | 69.6 | 250 |
| CDY23252.1 | BnaA08g12940D [*Brassica napus*] | 49.064 | 65.17 | 267 |
| CDY55618.1 | BnaC03g77520D [*Brassica napus*] | 47.94 | 65.17 | 267 |
| XP_009102300.1 | PREDICTED: uncharacterized protein LOC103828450 [*Brassica rapa*] | 46.792 | 63.77 | 265 |

TABLE 5-continued

BLASTP search results identifying plant Kanghan proteins based on sequence similarity to the protein encoded by AT4G29770.

| Seq | Gene | Identities | Positives | Length of Alignment |
|---|---|---|---|---|
| XP_009108975.1 | PREDICTED: uncharacterized protein LOC103834660 isoform X3 [*Brassica rapa*] | 47.94 | 62.55 | 267 |
| CDY55620.1 | BnaC03g77540D [*Brassica napus*] | 48.387 | 63.71 | 248 |
| XP_010495074.1 | PREDICTED: uncharacterized protein LOC104772124 [*Camelina sativa*] | 49.434 | 58.11 | 265 |
| XP_013674022.1 | PREDICTED: uncharacterized protein LOC106378439 [*Brassica napus*] | 47.059 | 65.16 | 221 |
| XP_010433021.1 | PREDICTED: uncharacterized protein LOC104717183 [*Camelina sativa*] | 40.892 | 55.76 | 269 |
| XP_010438210.1 | PREDICTED: uncharacterized protein LOC104721842 [*Camelina sativa*] | 42.804 | 54.98 | 271 |
| XP_010447759.1 | PREDICTED: uncharacterized protein LOC104730304 [*Camelina sativa*] | 42.857 | 55.64 | 266 |
| XP_006393225.1 | hypothetical protein EUTSA_v10011766mg [*Eutrema salsugineum*] | 42.912 | 52.87 | 261 |
| CDY55622.1 | BnaC03g77550D [*Brassica napus*] | 43.939 | 56.82 | 264 |
| KFK22930.1 | hypothetical protein AALP_AAs51418U000100 [*Arabis alpina*] | 42.339 | 55.24 | 248 |
| XP_010447760.1 | PREDICTED: uncharacterized protein LOC104730305 [*Camelina sativa*] | 42.578 | 55.08 | 256 |
| XP_002894098.1 | F21D18.8 [*Arabidopsis lyrata* subsp. *lyrata*] | 39.147 | 52.33 | 258 |
| XP_009108976.1 | PREDICTED: uncharacterized protein LOC103834661 [*Brassica rapa*] | 47.541 | 64.48 | 183 |
| XP_010479661.1 | PREDICTED: uncharacterized protein LOC104758482 [*Camelina sativa*] | 39.683 | 53.97 | 252 |
| XP_010462001.1 | PREDICTED: uncharacterized protein LOC104742681 [*Camelina sativa*] | 39.044 | 53.39 | 251 |
| KFK30349.1 | hypothetical protein AALP_AA7G249900 [*Arabis alpina*] | 42.387 | 54.73 | 243 |
| XP_006304151.1 | hypothetical protein CARUB_v10010162mg [*Capsella rubella*] | 39.768 | 53.28 | 259 |
| XP_010482049.1 | PREDICTED: uncharacterized protein LOC104760782 [*Camelina sativa*] | 38.672 | 51.95 | 256 |
| NP_680172.2 | AT5G18065 | 63.415 | 73.98 | 123 |
| XP_010479658.1 | PREDICTED: uncharacterized protein LOC104758479 [*Camelina sativa*] | 36.822 | 52.33 | 258 |
| XP_002891651.1 | predicted protein [*Arabidopsis lyrata* subsp. *lyrata*] | 38.492 | 51.98 | 252 |
| NP_175252.1 | AT1G48180 | 35.907 | 50.19 | 259 |
| XP_006304149.1 | hypothetical protein CARUB_v10010150mg [*Capsella rubella*] | 36.863 | 51.37 | 255 |
| XP_002891717.1 | hypothetical protein ARALYDRAFT_892299 [*Arabidopsis lyrata* subsp. *lyrata*] | 37.549 | 51.78 | 253 |
| XP_010471249.1 | PREDICTED: uncharacterized protein LOC104751067 [*Camelina sativa*] | 36.957 | 50.87 | 230 |
| AAF79518.1 | F21D18.8 [*Arabidopsis thaliana*] | 35.125 | 48.39 | 279 |
| XP_006303339.1 | hypothetical protein CARUB_v10010206mg [*Capsella rubella*] | 36.8 | 51.6 | 250 |
| XP_010501962.1 | PREDICTED: uncharacterized protein LOC104779303 [*Camelina sativa*] | 34.348 | 49.57 | 230 |
| AAG50884.1 | unknown protein [*Arabidopsis thaliana*] | 36.111 | 49.6 | 252 |

TABLE 5-continued

BLASTP search results identifying plant Kanghan proteins based on sequence similarity to the protein encoded by AT4G29770.

| Seq | Gene | Identities | Positives | Length of Alignment |
|---|---|---|---|---|
| XP_010442215.1 | PREDICTED: uncharacterized protein LOC104725285 [Camelina sativa] | 38.095 | 50.6 | 168 |
| XP_010500744.1 | PREDICTED: uncharacterized protein LOC104778076 [Camelina sativa] | 30.038 | 44.49 | 263 |
| KFK24575.1 | hypothetical protein AALP_AAs45078U000200 [Arabis alpina] | 47.581 | 61.29 | 124 |
| NP_175578.2 | AT1G51670 | 36.628 | 49.42 | 172 |
| XP_013684707.1 | PREDICTED: uncharacterized protein LOC106389038 isoform X1 [Brassica napus] | 31.818 | 50 | 176 |
| CDY43538.1 | BnaA01g07060D [Brassica napus] | 31.818 | 50 | 176 |
| XP_013684772.1 | PREDICTED: uncharacterized protein LOC106389038 isoform X2 [Brassica napus] | 31.818 | 50 | 176 |
| XP_013596364.1 | PREDICTED: uncharacterized protein LOC106304487 isoform X3 [Brassica oleracea var. oleracea] | 35.537 | 53.72 | 121 |
| XP_013750812.1 | PREDICTED: uncharacterized protein LOC106453111 isoform X3 [Brassica napus] | 33.871 | 50 | 124 |
| XP_013750806.1 | PREDICTED: uncharacterized protein LOC106453111 isoform X1 [Brassica napus] | 33.871 | 50 | 124 |
| NP_001154277.1 | target of trans acting-siR480/255 [Arabidopsis thaliana] | 33.884 | 50.41 | 121 |

Example 4: Modulating Abiotic Stress Response in Wheat with Kanghan Genes

This example illustrates a genetic modification of a wild-type wheat by gene gun mediated transformation using a Kanghan gene construct, to modulate an abiotic stress response, in this case conferring heat tolerance. Transgenic constructs for overexpression of *Arabidopsis* Kanghan family genes in wheat were produced using monocot special overexpression vector PANIC5E. This vector was designed for stable transformation and overexpression of heterologous Kanghan genes in wheat. Over expression of *Arabidopsis* Kanghan 1 (At5g18040) in one wheat wild type (Fielder) was achieved in this way by gene gun mediated transformation. The construct used to perform this transformation is shown in FIG. 8.

To illustrate the heat tolerance of the wheat transgenic lines, three-week seedlings of both wild types and T1 transgenic lines were heat treated at 42/38° C. (day/night). After two weeks of heat treatment, recovery at normal growth temperature was performed, and phenotypes observed. Heat tolerance was clearly observed in T1 transformants compared to non-transgenic plants under heat treatment. Non-transgenic plants displayed wilt symptoms or died. The transformants, on the other hand, recovered after transferring to normal growth temperature conditions, and were able to grow normally and transit to reproductive growth.

To further illustrate the heat tolerance of the wheat transgenic lines, three week old seedlings of both wild-type and T1 transgenic lines were subjected to 40/38° C. (day/night) for three weeks, followed by a three week recovery period at 25° C. After this recovery period, the transgenic plants fully recovered whereas the control plants failed to recover (FIGS. 9A and 9B). After a further seven weeks at 25° C., the transgenic plants reached maturity and produced seeds (FIG. 9C).

Under standard growth conditions of 23° C. day/18° C. night, 16 h photoperiod (16 h light/8 h dark), and 200 µmol m-2s-1 light intensity wild-type and transgenic plants are visually indistinguishable, however as determined by infrared thermal imaging using FLIR T640 Infrared Camera, the canopy temperature of T1 transgenic wheat plants is significantly lower (FIG. 10).

These studies illustrate the utility of the Kanghan genes in modulating abiotic stress response in crop species such as wheat, in this case to improve heat tolerance.

Example 5: Identifying Kanghan Homologs in *Brassica napus*

A BLAST sequence search was carried out on available genome and transcript data from *Brassica napus* to identify potential homologues of at4g29770, at4g29760, at5g18040, at5g18065, at1g51670, and at1g48180. The potential candidates identified are provided in Table 6.

TABLE 6

Homologs of *Arabidopsis thaliana* Kanghan family genes in *Brassica napus*.

| Homologs of at4g29770, at4g29760, at5g18040, and at5g18065 | Homologs of at1g51670 and at1g48180 |
|---|---|
| BnaA01g06470D | BnaC01g08520D |
| BnaA07g02270D | BnaC01g08490D |
| BnaA08g12920D | BnaA01g07060D |
| BnaA08g12930D | |
| BnaA08g12940D | |

TABLE 6-continued

Homologs of *Arabidopsis thaliana* Kanghan family genes in *Brassica napus*.

| Homologs of at4g29770, at4g29760, at5g18040, and at5g18065 | Homologs of at1g51670 and at1g48180 |
|---|---|
| BnaC01g07670D | |
| BnaC03g77520D | |
| BnaC03g77540D | |
| BnaC03g77550D | |

A DNA neighbor phylogenetic tree of the *Brassica napus* Kanghan gene candidates and their *Arabidopsis thaliana* counterparts is provided in FIG. 11 and a protein neighbor phylogenetic tree is provided in FIG. 12. A DNA neighbor phylogenetic tree of the *Brassica napus* Kanghan gene candidates is shown in FIG. 13. The candidates indicated by arrows were selected for targeting by RNAi.

Example 6: Targeting *Brassica napus* Kanghan Genes by RNAi

Primer Design

Two conserved fragments from 12 putative *Brassica napus* Kanghan genes, identified based on ClustalW multiple alignment, were used to design two pairs of RNAi primers.

The reverse primers were designed to include a BamH1 restriction site and a Sal1 restriction site to facilitate cloning.

The first primer pair was designed to target BnaC03g77540D (LOC106364365):

```
RNAiF1 GP438:
                                           (SEQ ID NO: 20)
TAGATTCTGCTGAGAGAGCCGCTAC

RNAiR1 GP439:
                                           (SEQ ID NO: 21)
GGATCCGTCGACGCACCTATGGGTCCATGCTTTAAC
```

The second primer pair was designed to target BnaA08g12920D (LOC106424160):

```
RNAiF2 GP440:
                                           (SEQ ID NO: 22)
TCATCCAGATTGCCAACGAG

RNAiR2 GP441:
                                           (SEQ ID NO: 23)
GGATCCGTCGACACGCATCCTCCAGTGTCTTAG
```

Production of BnKanghan RNAi Construct and Establishment of *Brassica napus* RNAi Lines To generate a cDNA library of *Brassica napus*, total RNA was isolated from 3-week-old leaves of canola wild type 'Hero' using the Plant RNeasy Mini Kit (Qiagen). Then, RNA samples were used for library construction using the QuantiTect Reverse Transcription Kit (Qiagen). The primer pairs RNAiF1 GP438 (SEQ ID NO: 20)+RNAiR1 GP439 (SEQ ID NO: 21) and RNAiF2 (SEQ ID NO: 22)+RNAiR2 GP441 (SEQ ID NO: 23) were used separately to amplify fragments from two target BnKanghan genes from the obtained cDNA library. Each of the resulting PCR products was isolated and cloned into the pGEM®-T vector (Promega, USA). A map of the pGEM-T vector is provided in FIG. 14. Then, two copies of the Kanghan gene fragments were subcloned into the pCAMBIA 1301-35S-Int-T7 vector in opposite orientations using a Pst1, Sal1 digest and a BamH1, Sac1 digest to generate two RNAi constructs, one for each gene fragment. A map of the pCAMBIA 1301-35S-Int-T7 vector is provided in FIG. 15 and a partial map of the resulting RNAi constructs is provided in FIG. 16.

Next, a genetic modification of canola wild type 'Hero' was conducted using both of these completed RNAi constructs through *agrobacterium*-mediated transformation aimed to obtain increased drought tolerance. Positive transformants were confirmed using a pair of hygromycin specific primers (HptF TACACAGCCATCGGTCCAGA (SEQ ID NO: 24) and HptR GTAGGAGGGCGTGGATATGTC (SEQ ID NO: 25)). A cross was carried out between T1 positive transformants from the two different constructs. In the C2 generation, lines harboring both constructs together were selected for further evaluation of silencing of BnKanghan family genes and drought tolerance traits.

To assess the expression level of BnKanghan family genes in transgenic and crossing lines, a number of primer pairs were designed for qRT-PCR assays to assess the expression levels of seven candidate Kanghan genes from *Brassica napus*. The targets of these primer pairs are identified in Table 7. In total, 12 lines harboring both RNAi constructs from the C2 generation were selected to detect expression level changes of BnKanghan family genes. Each line tested showed decreases in expression of at least three BnKanghan genes. Individual lines C2-83-20 and C2-83-10 each showed decreased expression of six BnKanghan genes. These two lines were selected for further drought tolerance measurements.

TABLE 7 qRT-PCR primers targeting BnKanghan family genes.

| primer no. | SEQ ID NO: | primer sequence | product length | Kanghan gene |
|---|---|---|---|---|
| GP635 | 26 | CGCTACGAGGCACGTACTCAAT | 103 | BnaA07g02270D |
| GP636 | 27 | CTCGGTCTTCCCCGGTTTC | | |
| GP637 | 28 | GCTTAGAGACGTGATCCTGGTAGC | 128 | BnaA08g12920D |
| GP638 | 29 | CCAGTGTGGTGAACATACGGC | | |
| GP639 | 30 | GTTTTGTTGGTCTCTTCTCTTTGC | 71 | BnaC01g07670D |
| GP640 | 31 | TTCTTAAGAGGCGTTTCAGATGG | | |
| GP641 | 32 | TGATTTGGGTTTTGCCTGATAC | 69 | BnaC03g77540D |
| GP642 | 33 | GAAACAAACCATAAATGAGTTGCC | | |
| GP645 | 34 | CATTTGGGATGTGTCGATTGAG | 165 | BnaC03g77550D |
| GP646 | 35 | CCCACGTAGCTTGTTCCGTT | | |
| GP649 | 36 | AACACTGTCACGCAGATTGCC | 124 | BnaA01g06470D |
| GP650 | 37 | CTGTCCAGGTTAGCTACCATACGA | | |

TABLE 7-continued qRT-PCR primers targeting BnKanghan family genes.

| primer no. | SEQ ID NO: | primer sequence | product length | Kanghan gene |
|---|---|---|---|---|
| GP655 | 38 | CGGTATCCAACTCATTCGAAGG | 121 | BnaC01g08490D |
| GP656 | 39 | TCAAGTATATACTGGGTTGGCTGC | | |

Testing Canopy Temperature and Drought Tolerance of *Brassica napus* RNAi Lines

To predict the potential drought tolerance of the C2-83-20 and C2-83-10 lines, the canopy temperatures were measured using an infrared camera. In comparison to wild type plants, higher canopy temperatures were observed for the transgenic plants (FIG. 17) indicating a lower leaf water potential. These RNAi phenotypes are similar to loss-of-function alleles of AtKanghan genes in *Arabidopsis*, which suggests a similar role for the BnKanghan genes in canola.

To assess the drought tolerance of the transgenic plants, four weeks-old plants of both wild type and these two transgenic lines were subjected to drought treatment. The same amount of soil and water were applied to each individual plant before treatment, and then the water supply was stopped. After two weeks of drought treatment, recovery by re-watering of the plants was performed. The resulting phenotypes are shown in FIGS. 18 and 19. Increased drought tolerance was clearly observed in transgenic lines compared to wild type plants under drought conditions that lead to wilt symptoms or death of the wild type plants. The transformants, on the other hand, recovered after being transferred to normal watering conditions and were able to grow up normally and transit to reproductive growth. This demonstrates that silencing of BnKanghan family genes in crop species, such as canola, can improve drought tolerance.

While the present application has been described with reference to specific examples, it is to be understood that the application is not limited to the disclosed examples. To the contrary, the present application is intended to cover various modifications and equivalent arrangements encompassed by the scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

What is claimed is:

1. A transgenic Brassicaceae plant or plant cell comprising a recombinant nucleic acid construct encoding at least one inhibitory polynucleotide that targets an endogenous Kanghan gene in the transgenic Brassicaceae plant or plant cell to reduce or eliminate expression of a Kanghan protein encoded by the Kanghan gene, wherein:

the recombinant nucleic acid construct comprises a nucleic acid molecule encoding the at least one inhibitory polynucleotide operably linked to a heterologous promoter;

the Kanghan protein is selected from the group consisting of (i) a Kanghan protein having at least 95% sequence identity to the amino acid sequence set forth in SEQ ID NO: 17; (ii) a Kanghan protein having at least 95% amino acid identity to the amino acid sequence set forth in GenBank sequence Accession Number: CDY55620.1, which is encoded by *Brassica napus* Kanghan gene BnaCO3g77540D (LOC106364365); and (iii) a Kanghan protein having at least 95% sequence identity to the amino acid sequence set forth in GenBank sequence Accession Number: CDY23254.1, which is encoded by *Brassica napus* Kanghan gene BnaA08g12920D (LOC106424160);

expression of the at least one inhibitory polynucleotide in the transgenic Brassicaceae plant or plant cell increases drought tolerance of the transgenic Brassicaceae plant or plant cell relative to a control Brassicaceae plant or plant cell of the same species lacking the at least one inhibitory polynucleotide and grown under the same conditions; and the at least one inhibitory polynucleotide comprises an anti-sense oligonucleotide or an RNAi oligonucleotide.

2. A transgenic seed obtained from a transgenic Brassicaceae plant as defined in claim 1, wherein the transgenic seed comprises the recombinant nucleic acid construct.

3. The transgenic Brassicaceae plant or plant cell of claim 1, wherein the Brassicaceae plant or plant cell is a *Brassica napus* plant or plant cell.

4. A transgenic seed obtained from a transgenic *Brassica napus* plant as defined in claim 3, wherein the transgenic seed comprises the recombinant nucleic acid construct.

5. The transgenic Brassicaceae plant or plant cell of claim 1, wherein the at least one inhibitory polynucleotide comprises an RNAi oligonucleotide.

6. A transgenic seed obtained from a transgenic Brassicaceae plant as defined in claim 5, wherein the transgenic seed comprises the recombinant nucleic acid construct.

7. The transgenic Brassicaceae plant or plant cell of claim 5, wherein the Brassicaceae plant or plant cell is a *Brassica napus* plant or plant cell.

8. A transgenic seed obtained from a transgenic *Brassica napus* plant as defined in claim 7, wherein the transgenic seed comprises the recombinant nucleic acid construct.

9. The transgenic Brassicaceae plant or plant cell of claim 1, wherein the Kanghan protein has at least 95% amino acid identity to the amino acid sequence set forth in GenBank sequence Accession Number: CDY55620.1, which is encoded by *Brassica napus* Kanghan gene BnaCO3g77540D (LOC106364365).

10. The transgenic Brassicaceae plant or plant cell of claim 1, wherein the Kanghan protein has least 95% sequence identity to the amino acid sequence set forth in GenBank sequence Accession Number: CDY23254.1, which is encoded by *Brassica napus* Kanghan gene BnaA08g12920D (LOC106424160).

11. The transgenic Brassicaceae plant or plant cell of claim 7, wherein the Kanghan protein comprises the amino acid sequence set forth in GenBank sequence Accession Number: CDY55620.1, which is encoded by *Brassica napus* Kanghan gene BnaCO3g77540D (LOC 106364365).

12. The transgenic Brassicaceae plant or plant cell of claim 7, wherein the Kanghan protein comprises the amino acid sequence set forth in GenBank sequence Accession Number: CDY23254.1, which is encoded by *Brassica napus* Kanghan gene BnaA08g12920D (LOC 106424160).

13. A method of obtaining a transgenic plant comprising:

(i) transforming at least one Brassicaceae plant cell with a recombinant nucleic acid construct as defined in claim 1 to produce at least one transformed Brassicaceae plant cell;

(ii) obtaining at least one transgenic Brassicaceae plant from the at least one transformed Brassicaceae plant cell of step (i); and (iii) selecting a transgenic Brassicaceae plant from the at least one transgenic Brassicaceae plant of step (ii) that expresses the at least one inhibitory polynucleotide and exhibits increased drought tolerance relative to a control Brassicaceae plant or plant cell of the same species lacking the at least one inhibitory polynucleotide and grown under the same conditions.

14. The method of claim 13, further comprising obtaining one or more transgenic seeds from the selected Brassicaceae plant of step (iii).

* * * * *

SEQUENCE LISTING

```
<160> NUMBER OF SEQ ID NOS: 43

<210> SEQ ID NO 1
<211> LENGTH: 843
<212> TYPE: DNA
<213> ORGANISM: Arabidopsis thaliana

<400> SEQUENCE: 1
atggctgagc gattattaca atctatgtca agggtggctg gccgatgtca tccagattgc      60
gtaaaagcaa gtgatgagca agaagattac catgcatctc aaaatgcagc tttggtagct     120
gtgaatctga ttagctctgc aaggttaata ctgaaactcg acgctgagtt tactgagtac     180
tcagctcagt ttttgatgga caatgctgga aaggaagacg acccgggaga agtggatcaa     240
caacgcaatc aggtcacgac cgaaaactgc cttcgctact tggccgaaaa cgtttggacc     300
aagaaggaaa atgggcaggg aggaatggat caacaacgcc ctgtgctcac tgtcaaagac     360
tgcttggaac ttgcttttaa aaaagggctg ccgagaagaa aacactgggc acatttggga     420
tgtaccttca aggctccccc atttgcttgt cagatacctc gcgttcctgt gaaaggagaa     480
gtggttgagg ttaagacttt tgatgaagca ttcaagctgt tggtgcatca acccattgga     540
gcaaaactgc atttgttcag tccgcagatt gataatgttg gagagggagt ttacaaaggc     600
ctcacgacag gtaatgaaac acactatgtt ggacttagag atgtgctaat agcttcagtg     660
gaggagttcg agggagattc tgttgctatt gtgaagatct gctacaagaa gaagctttca     720
tttatcaaag tgtctttgag cgttaggttt ctctcagtag cacatgatgg tgataagtct     780
aagttcatag cgccaacagg tctgcttgtt gacttctgtg tcccgcgctt atctatcaac     840
taa                                                                    843

<210> SEQ ID NO 2
<211> LENGTH: 990
<212> TYPE: DNA
```

<213> ORGANISM: Arabidopsis thaliana

<400> SEQUENCE: 2

| | | |
|---|---|---|
| atgatggcaa tctcagaaaa aggagtcatg gcaatctcag aaaaaggagt catggcaacg | 60 |
| aaaattgaca aaacggcgt ccttcgagag ttaaggcgac atttcactga gttttctcta | 120 |
| cgcgacgtag atctgtgtct ccggagttca tcgcagatgg agtcattgtt agaatgtttt | 180 |
| gcaatcacgg atggcaaatg tcatcccgat tgcttaaaag caaacaatga gcaagaagat | 240 |
| tacgatgcat gtcaatctgc agctttggta gctgtgagtt tgattagctc tgcacgtgtt | 300 |
| atcttcaaga tcgactctaa gtatactgag tactcacctc agtatttggt ggataacgtt | 360 |
| gggaaggaag aagttgaggg agaaatggat caaccaagct gtcagtacac tgtcggaaac | 420 |
| ctccttagtt acttggtgga aaacgtttgg accaagaagg aagttaggca gagagaaatg | 480 |
| gatcaacaac gccgtgagtt cactgtcaaa gactgctttg aatttgcttt taaaaaaggg | 540 |
| cttccaagaa atggacattg gcgcatgtg ggatgtatat tcccggttcc tccatttgct | 600 |
| tgtcaaatac ctcgcgttcc catgaaagga gaagtgattg aggctgcaaa tgtgagtgaa | 660 |
| gcgttgaagc tgggtatgca acaaccagcg gcagcaaggc tgcatttgtt cagtccagag | 720 |
| tttgatcttg ttggagaggg tatttacgat ggcccgtcag gtaatgaaac acgatatgtt | 780 |
| ggacttagag atgtgctcat ggttgaggcg agaagatca agggagaaac tgttttact | 840 |
| gtgcagatat gctacaagaa gaagacttca tttgtcaaag tgtctacgag aagtatgatt | 900 |
| ctcccgctta atggtgacga cgagtctcag gtcacagagc cagcatgtct acttgttgac | 960 |
| ttctgtatcc cacgttttc tatcaactaa | 990 |

<210> SEQ ID NO 3
<211> LENGTH: 381
<212> TYPE: DNA
<213> ORGANISM: Arabidopsis thaliana

<400> SEQUENCE: 3

| | | |
|---|---|---|
| atggatatga atcagctatt catgcaatct attgcaaaca gtcgtggact ctgtcatcca | 60 |
| gattgcgaaa agcaaataa tgagcgtgaa gattatgatg cgtctcaaca tgccgctatg | 120 |
| gtagcggtga atctgattag ctctgcacgg gttatcctca gcttgatgc tgtgtatact | 180 |
| gagtactcag ctcagtattt ggtggataat gctgggaagg aagacaacca gggagaaatg | 240 |
| gatcaacaaa gctctcagct cactctccaa aacttgcttc agtatatgga tgaaaatgtc | 300 |
| tggaataaga aggaagatgt gcagggagaa agggagcaac cactcactgt caaagactgc | 360 |
| cttgaatgtg ctttcaagta a | 381 |

<210> SEQ ID NO 4
<211> LENGTH: 759
<212> TYPE: DNA
<213> ORGANISM: Arabidopsis thaliana

<400> SEQUENCE: 4

| | | |
|---|---|---|
| atgaatatga ttcagcgatt catgcaatct atggcaaaga cgcgtggcct ctgtcatcca | 60 |
| gattgcgtaa agcaagtag tgagcaagaa gattacgatg cgtctcagct cagtatttgg | 120 |
| tggataatgc tgggaaggaa gacgaccagg gagaaatgga tgaaccaagc tctcagttca | 180 |
| ctatcgaaaa cttgcatcag tatatggtgg aaaatgtctg gaataagagg taagatgtgc | 240 |
| agggagaggg agcaaccact cactgtcaaa gactgccttg aatgtgcttt caagaaaggg | 300 |
| ctaccgagaa gagaacattg gcacatgtg ggatgtacat tcaaggctcc cccatttgct | 360 |

```
tgtcacatac cccgcgtgcc catgaaagga gaagtgattg agactaagag tttggatgaa      420
gcgtttaagc tgttgattaa acaaccggtg ggtgcaagac tccatgtgtt cagtccagac      480
cttgataatg ttggagaggg agtttacgag ggcctgtcta gcctgtctcg taaggaatca      540
cgctatgttg gacttaggga tgtcatcata gttgcagtga ataagtccga gggaaaaact      600
gttgctactg tgaagatatg ttacaagaag aagacttcat ttgtcaaagt gtgtttgagc      660
cgtatgtttg tccagcttgg tggtggcgag gagtctcagg tgaaagagcc aacaggtctg      720
cttgttgact tctgtatccc acgcttatct atcaactaa                             759
```

```
<210> SEQ ID NO 5
<211> LENGTH: 537
<212> TYPE: DNA
<213> ORGANISM: Arabidopsis thaliana

<400> SEQUENCE: 5
atggcactcc ctccctatga tccgaatttc acattggctt tttcatacgg tagacgcgat       60
aatgtctttg agaatgaccc agagcacgat gaatctgctt ctgctgctat cgtagcggtt      120
gagctgataa gctctgcacg gcttgcactt aagctggata tgtccgcac tgagtactca       180 gctcagtatt tggtggacaa agctggctca cgcaaccctca ggcgcaggcg caagctcact      240
gtcaaggact gccttaactt tgcgttaaag aaaggcggca taccgagagc agaagattgg      300
ccacctttgg gatctgagtc aaagacccca tcatcgtacg aacctgctct cgtttccatg      360
aaaggagaag tgattgagcc taaggatatg gacgaagtac ctgagttgtt ggtgcatcaa      420
tcagccgtgg gagcaaaact gcatgtgttc actccacaca ttgaacttca acaagacgca      480
atttacttgc ctcgtcaggt gagtatgcgc gctacgttgg acttagagat gggatag         537
```

```
<210> SEQ ID NO 6
<211> LENGTH: 12
<212> TYPE: PRT
<213> ORGANISM: Artificial Sequence
<220> FEATURE:
<223> OTHER INFORMATION: Consensus sequence Kanghan conserved domain B
<220> FEATURE:
<221> NAME/KEY: MISC_FEATURE
<222> LOCATION: (1)..(1)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (7)..(7)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (8)..(8)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (9)..(9)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (11)..(11)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (12)..(12)
<223> OTHER INFORMATION: Xaa is Cys, Asp, Glu, His, Lys, Asn, Gln, Arg,
      Ser, or Thr
```

-continued

```
<400> SEQUENCE: 6

Xaa Thr Val Lys Asp Cys Xaa Xaa Xaa Ala Xaa Xaa
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Consensus sequence Kanghan conserved domain B
<220> FEATURE:
<221> NAME/KEY: MISC_FEATURE
<222> LOCATION: (9)..(9)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (11)..(11)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (13)..(13)
<223> OTHER INFORMATION: Xaa is Lys or is absent

<400> SEQUENCE: 7

Leu Thr Val Lys Asp Cys Leu Glu Xaa Ala Xaa Lys Xaa Gly
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Consensus sequence of Kanghan conserved domain
      B
<220> FEATURE:
<221> NAME/KEY: MISC_FEATURE
<222> LOCATION: (9)..(9)
<223> OTHER INFORMATION: Xaa is Ala, Cys, Phe, Gly, His, Ile, Lys, Leu,
      Met, Arg, Thr, Val, Trp or Tyr

<400> SEQUENCE: 8

Leu Thr Val Lys Asp Cys Leu Glu Xaa Ala Phe Lys Lys Gly
1               5                   10

<210> SEQ ID NO 9
<211> LENGTH: 37
<212> TYPE: PRT
<213> ORGANISM: Artificial Sequence
<220> FEATURE:
<223> OTHER INFORMATION: Consensus sequence Kanghan conserved domain C
<220> FEATURE:
<221> NAME/KEY: MISC_FEATURE
<222> LOCATION: (2)..(2)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (3)..(3)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: MISC_FEATURE
<222> LOCATION: (6)..(6)
<223> OTHER INFORMATION: Xaa is Cys, Asp, Glu, His, Lys, Asn, Gln, Arg,
      Ser or Thr
<220> FEATURE:
<221> NAME/KEY: MISC_FEATURE
<222> LOCATION: (8)..(8)
<223> OTHER INFORMATION: Xaa is Ile, Leu, or Val
<220> FEATURE:
<221> NAME/KEY: MISC_FEATURE
```

```
<222> LOCATION: (10)..(10)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (11)..(11)
<223> OTHER INFORMATION: Xaa is Ala, Cys, Asp, Glu, Gly, His, Lys, Asn,
      Gln, Arg, Ser or Thr
<220> FEATURE:
<221> NAME/KEY: MISC_FEATURE
<222> LOCATION: (12)..(12)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (13)..(13)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: MISC_FEATURE
<222> LOCATION: (14)..(14)
<223> OTHER INFORMATION: Xaa is Cys, Asp, Glu, His, Lys, Asn, Gln, Arg,
      Ser or Thr
<220> FEATURE:
<221> NAME/KEY: MISC_FEATURE
<222> LOCATION: (16)..(16)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (17)..(17)
<223> OTHER INFORMATION: Xaa is any naturally occurring amino acid
<220> FEATURE:
<221> NAME/KEY: MISC_FEATURE
<222> LOCATION: (18)..(18)
<223> OTHER INFORMATION: Xaa is Asp, Glu, His, Lys or Arg
<220> FEATURE:
<221> NAME/KEY: MISC_FEATURE
<222> LOCATION: (19)..(19)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: MISC_FEATURE
<222> LOCATION: (20)..(20)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: MISC_FEATURE
<222> LOCATION: (21)..(21)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: MISC_FEATURE
<222> LOCATION: (22)..(22)
<223> OTHER INFORMATION: Xaa is Cys, Asp, Glu, His, Lys, Asn, Gln, Arg,
      Ser or Thr
<220> FEATURE:
<221> NAME/KEY: MISC_FEATURE
<222> LOCATION: (24)..(24)
<223> OTHER INFORMATION: Xaa is Ala, Cys, Asp, Gly, Asn, Pro, Ser, Thr
      or Val
<220> FEATURE:
<221> NAME/KEY: MISC_FEATURE
<222> LOCATION: (25)..(25)
<223> OTHER INFORMATION: Xaa is Asp or Glu
<220> FEATURE:
<221> NAME/KEY: MISC_FEATURE
<222> LOCATION: (26)..(26)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (27)..(27)
<223> OTHER INFORMATION: Xaa is Arg, Gly, or Ser
<220> FEATURE:
<221> NAME/KEY: MISC_FEATURE
<222> LOCATION: (29)..(29)
<223> OTHER INFORMATION: Xaa is His, Lys, or Arg
<220> FEATURE:
```

-continued

```
<221> NAME/KEY: MISC_FEATURE
<222> LOCATION: (32)..(32)
<223> OTHER INFORMATION: Xaa is Ile, Leu, or Val
<220> FEATURE:
<221> NAME/KEY: MISC_FEATURE
<222> LOCATION: (34)..(34)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (36)..(36)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (37)..(37)
<223> OTHER INFORMATION: Xaa is Ala, Cys, Phe, Gly, His, Ile, Lys, Leu,
      Met, Arg, Thr, Val, Trp, or Tyr

<400> SEQUENCE: 9

Val Xaa Xaa Lys Gly Xaa Val Xaa Glu Xaa Xaa Xaa Xaa Xaa Glu Xaa
1               5                   10                  15

Xaa Xaa Xaa Xaa Xaa Xaa Gln Xaa Xaa Xaa Xaa Ala Xaa Leu His Xaa
            20                  25                  30

Phe Xaa Pro Xaa Xaa
        35

<210> SEQ ID NO 10
<211> LENGTH: 36
<212> TYPE: PRT
<213> ORGANISM: Artificial Sequence
<220> FEATURE:
<223> OTHER INFORMATION: Consensus sequence Kanghan conserved domain C
<220> FEATURE:
<221> NAME/KEY: MISC_FEATURE
<222> LOCATION: (2)..(2)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (10)..(10)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (11)..(11)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (12)..(12)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (13)..(13)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (14)..(14)
<223> OTHER INFORMATION: Xaa is Asp or Glu
<220> FEATURE:
<221> NAME/KEY: MISC_FEATURE
<222> LOCATION: (17)..(17)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (18)..(18)
<223> OTHER INFORMATION: Xaa is Asp, Glu, His, Lys, or Arg
<220> FEATURE:
<221> NAME/KEY: MISC_FEATURE
<222> LOCATION: (20)..(20)
<223> OTHER INFORMATION: Xaa is Ile, Leu, or Val
```

-continued

```
<220> FEATURE:
<221> NAME/KEY: MISC_FEATURE
<222> LOCATION: (21)..(21)
<223> OTHER INFORMATION: Xaa is Ile

-continued

```
      Ser, or Thr
<220> FEATURE:
<221> NAME/KEY: MISC_FEATURE
<222> LOCATION: (13)..(13)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (16)..(16)
<223> OTHER INFORMATION: Xaa is Ile, Leu, or Val
<220> FEATURE:
<221> NAME/KEY: MISC_FEATURE
<222> LOCATION: (17)..(17)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (24)..(24)
<223> OTHER INFORMATION: Xaa is Ile, Leu, or Val
<220> FEATURE:
<221> NAME/KEY: MISC_FEATURE
<222> LOCATION: (25)..(25)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (28)..(28)
<223> OTHER INFORMATION: Xaa is Ile, Leu, or Val
<220> FEATURE:
<221> NAME/KEY: MISC_FEATURE
<222> LOCATION: (30)..(30)
<223> OTHER INFORMATION: Xaa is Arg, Gly, or Ser
<220> FEATURE:
<221> NAME/KEY: MISC_FEATURE
<222> LOCATION: (31)..(31)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (32)..(32)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (37)..(37)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (39)..(39)
<223> OTHER INFORMATION: Xaa is Phe, His, Trp, Tyr
<220> FEATURE:
<221> NAME/KEY: MISC_FEATURE
<222> LOCATION: (41)..(41)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (43)..(43)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (44)..(44)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (45)..(45)
<223> OTHER INFORMATION: Xaa is Arg, Gly, or Ser
<220> FEATURE:
<221> NAME/KEY: MISC_FEATURE
<222> LOCATION: (46)..(46)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (47)..(47)
<223> OTHER INFORMATION: Xaa is Cys, Asp, Glu, His, Lys, Asn, Gln, Arg,
```

```
                                Ser, or Thr
<220> FEATURE:
<221> NAME/KEY: MISC_FEATURE
<222> LOCATION: (48)..(48)
<223> OTHER INFORMATION: Xaa is Cys, Asp, Glu, His, Lys, Asn, Gln, Arg,
      Ser, or Thr

<400> SEQUENCE: 11

Xaa Xaa Xaa Asp Tyr Asp Xaa Ser Xaa Xaa Ala Ala Xaa Val Ala Xaa
1               5                   10                  15

Xaa Leu Ile Ser Ser Ala Arg Xaa Xaa Leu Lys Xaa Asp Xaa Xaa Xaa
            20                  25                  30

Thr Glu Tyr Ser Xaa Gln Xaa Leu Xaa Asp Xaa Xaa Xaa Xaa Xaa Xaa
        35                  40                  45

<210> SEQ ID NO 12
<211> LENGTH: 73
<212> TYPE: PRT
<213> ORGANISM: Artificial Sequence
<220> FEATURE:
<223> OTHER INFORMATION: Consensus sequence kanghan conserved domain A
<220> FEATURE:
<221> NAME/KEY: MISC_FEATURE
<222> LOCATION: (1)..(1)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (2)..(2)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (3)..(3)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (4)..(4)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (5)..(5)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (6)..(6)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (8)..(8)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (9)..(9)
<223> OTHER INFORMATION: Xaa is Arg, Gly, or Ser
<220> FEATURE:
<221> NAME/KEY: MISC_FEATURE
<222> LOCATION: (10)..(10)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (11)..(11)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (12)..(12)
<223> OTHER INFORMATION: Xaa is Asp, Glu, His, Lys, or Arg
<220> FEATURE:
```

```
<221> NAME/KEY: MISC_FEATURE
<222> LOCATION: (14)..(14)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (20)..(20)
<223> OTHER INFORMATION: Xaa is any naturally occuring amino acid
<220> FEATURE:
<221> NAME/KEY: MISC_FEATURE
<222> LOCATION: (23)..(23)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (24)..(24)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (26)..(26)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (34)..(34)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (36)..(36)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (37)..(37)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (41)..(41)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (48)..(48)
<223> OTHER INFORMATION: Xaa is Ile, Leu, or Val
<220> FEATURE:
<221> NAME/KEY: MISC_FEATURE
<222> LOCATION: (49)..(49)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (54)..(54)
<223> OTHER INFORMATION: Xaa is Arg, Gly, or Ser
<220> FEATURE:
<221> NAME/KEY: MISC_FEATURE
<222> LOCATION: (55)..(55)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (56)..(56)
<223> OTHER INFORMATION: Xaa is Phe, His, Trp, Tyr
<220> FEATURE:
<221> NAME/KEY: MISC_FEATURE
<222> LOCATION: (70)..(70)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (71)..(71)
<223> OTHER INFORMATION: Xaa is Asp, Glu, His, Lys, or Arg
<220> FEATURE:
<221> NAME/KEY: MISC_FEATURE
<222> LOCATION: (72)..(72)
<223> OTHER INFORMATION: Xaa is Asp, Glu, His, Lys, or Arg
<220> FEATURE:
```

-continued

<221> NAME/KEY: MISC_FEATURE
<222> LOCATION: (73)..(73)
<223> OTHER INFORMATION: Xaa is Ala, Cys, Asp, Gly, Asn, Pro, Ser, Thr, or Val

<400> SEQUENCE: 12

Xaa Xaa Xaa Xaa Xaa Xaa Ser Xaa Xaa Xaa Xaa Xaa Gly Xaa Cys His
1               5                   10                  15

Pro Asp Cys Xaa Lys Ala Xaa Xaa Glu Xaa Glu Asp Tyr Asp Ala Ser
            20                  25                  30

Gln Xaa Ala Ala Xaa Val Ala Val Xaa Leu Ile Ser Ser Ala Arg Xaa
        35                  40                  45

Xaa Leu Lys Leu Asp Xaa Xaa Xaa Thr Glu Tyr Ser Ala Gln Tyr Leu
50                  55                  60

Val Asp Asn Ala Gly Xaa Xaa Xaa Xaa
65                  70

<210> SEQ ID NO 13
<211> LENGTH: 720
<212> TYPE: DNA
<213> ORGANISM: Arabidopsis thaliana

<400> SEQUENCE: 13
atggcactcc cacctatga tcccaatttc aaatttgcat tctctcttgg cacgattgcg      60
aaacaccaag attacgatga atctgcttct gctgctgttg tagcgcttga tctgataagc     120
tctgcacggt ttgcacttaa gctggatagt gtctatactg agtactctgc taagtatgtg    180
gtggacaatg ctgctggctc acacagtggg cgcaagctca ctgtcaaaga ctgtcttgag    240
tttgccttaa acaaaggcgg cataccgaaa gcagaagatt ggccacgctt gggatctgtg    300
ataacgcccc catcatcgta taaacctgat ctcgtttcga tgaaaggaca agtgattgag    360
cctcagacta ttgaggaagc atgtgacatg gtggtggatc aaccagtagg agcaaaattg    420
catgtgttca agccacacat tgaacttcaa caagacgcaa gtgctataac tggcatttac    480
tgtggcacgt caggtgagcc agccagctat gtcggactta gagatgccat catcgttgga    540
gtcgagaaga tccaagggaa gtctattgga actgtgaagg tatggtacaa gaagttcata    600
tttctgaaag tggctatgag caggtggttt cagttatact ctccggatgg cacacacacg    660
ggcataaagc gaacagatta ccttgttgat ttttgtgtcc cacgcctatc catggattaa    720

<210> SEQ ID NO 14
<211> LENGTH: 280
<212> TYPE: PRT
<213> ORGANISM: Arabidopsis thaliana

<400> SEQUENCE: 14

Met Ala Glu Arg Leu Leu Gln Ser Met Ser Arg Val Ala Gly Arg Cys
1               5                   10                  15

His Pro Asp Cys Val Lys Ala Ser Asp Glu Gln Glu Asp Tyr His Ala
            20                  25                  30

Ser Gln Asn Ala Ala Leu Val Ala Val Asn Leu Ile Ser Ser Ala Arg
        35                  40                  45

Leu Ile Leu Lys Leu Asp Ala Glu Phe Thr Glu Tyr Ser Ala Gln Phe
50                  55                  60

Leu Met Asp Asn Ala Gly Lys Glu Asp Pro Gly Glu Val Asp Gln
65                  70                  75                  80

Gln Arg Asn Gln Val Thr Thr Glu Asn Cys Leu Arg Tyr Leu Ala Glu
                85                  90                  95

```
Asn Val Trp Thr Lys Lys Glu Asn Gly Gln Gly Gly Met Asp Gln Gln
             100                 105                 110

Arg Pro Val Leu Thr Val Lys Asp Cys Leu Glu Leu Ala Phe Lys Lys
             115                 120                 125

Gly Leu Pro Arg Arg Glu His Trp Ala His Leu Gly Cys Thr Phe Lys
         130                 135                 140

Ala Pro Pro Phe Ala Cys Gln Ile Pro Arg Val Pro Val Lys Gly Glu
145                 150                 155                 160

Val Val Glu Val Lys Thr Phe Asp Glu Ala Phe Lys Leu Leu Val His
                 165                 170                 175

Gln Pro Ile Gly Ala Lys Leu His Leu Phe Ser Pro Gln Ile Asp Asn
             180                 185                 190

Val Gly Glu Gly Val Tyr Lys Gly Leu Thr Thr Gly Asn Glu Thr His
         195                 200                 205

Tyr Val Gly Leu Arg Asp Val Leu Ile Ala Ser Val Glu Glu Phe Glu
210                 215                 220

Gly Asp Ser Val Ala Ile Val Lys Ile Cys Tyr Lys Lys Lys Leu Ser
225                 230                 235                 240

Phe Ile Lys Val Ser Leu Ser Val Arg Phe Leu Ser Val Ala His Asp
                 245                 250                 255

Gly Asp Lys Ser Lys Phe Ile Ala Pro Thr Gly Leu Leu Val Asp Phe
             260                 265                 270

Cys Val Pro Arg Leu Ser Ile Asn
         275                 280

<210> SEQ ID NO 15
<211> LENGTH: 329
<212> TYPE: PRT
<213> ORGANISM: Arabidopsis thaliana

<400> SEQUENCE: 15

Met Met Ala Ile Ser Glu Lys Gly Val Met Ala Ile Ser Glu Lys Gly
1               5                   10                  15

Val Met Ala Thr Lys Ile Asp Lys Asn Gly Val Leu Arg Glu Leu Arg
             20                  25                  30

Arg His Phe Thr Glu Phe Ser Leu Arg Asp Val Asp Leu Cys Leu Arg
         35                  40                  45

Ser Ser Ser Gln Met Glu Ser Leu Leu Glu Cys Phe Ala Ile Thr Asp
     50                  55                  60

Gly Lys Cys His Pro Asp Cys Leu Lys Ala Asn Asn Glu Gln Glu Asp
65                  70                  75                  80

Tyr Asp Ala Cys Gln Ser Ala Ala Leu Val Ala Val Ser Leu Ile Ser
                 85                  90                  95

Ser Ala Arg Val Ile Phe Lys Ile Asp Ser Lys Tyr Thr Glu Tyr Ser
             100                 105                 110

Pro Gln Tyr Leu Val Asp Asn Val Gly Lys Glu Val Glu Gly Glu
         115                 120                 125

Met Asp Gln Pro Ser Cys Gln Tyr Thr Val Gly Asn Leu Leu Ser Tyr
130                 135                 140

Leu Val Glu Asn Val Trp Thr Lys Lys Glu Val Arg Gln Arg Glu Met
145                 150                 155                 160

Asp Gln Gln Arg Arg Glu Phe Thr Val Lys Asp Cys Phe Glu Phe Ala
                 165                 170                 175

Phe Lys Lys Gly Leu Pro Arg Asn Gly His Trp Ala His Val Gly Cys
```

```
                180               185                190
Ile Phe Pro Val Pro Phe Ala Cys Gln Ile Pro Arg Val Pro Met
            195                 200                 205

Lys Gly Glu Val Ile Glu Ala Ala Asn Val Ser Glu Ala Leu Lys Leu
            210                 215                 220

Gly Met Gln Gln Pro Ala Ala Arg Leu His Leu Phe Ser Pro Glu
225                 230                 235                 240

Phe Asp Leu Val Gly Glu Gly Ile Tyr Asp Gly Pro Ser Gly Asn Glu
                245                 250                 255

Thr Arg Tyr Val Gly Leu Arg Asp Val Leu Met Val Glu Ala Glu Lys
            260                 265                 270

Ile Lys Gly Glu Thr Val Phe Thr Val Gln Ile Cys Tyr Lys Lys Lys
            275                 280                 285

Thr Ser Phe Val Lys Val Ser Thr Arg Ser Met Ile Leu Pro Leu Asn
            290                 295                 300

Gly Asp Asp Glu Ser Gln Val Thr Glu Pro Ala Cys Leu Leu Val Asp
305                 310                 315                 320

Phe Cys Ile Pro Arg Phe Ser Ile Asn
                325

<210> SEQ ID NO 16
<211> LENGTH: 126
<212> TYPE: PRT
<213> ORGANISM: Arabidopsis thaliana

<400> SEQUENCE: 16

Met Asp Met Asn Gln Leu Phe Met Gln Ser Ile Ala Asn Ser Arg Gly
1               5                   10                  15

Leu Cys His Pro Asp Cys Glu Lys Ala Asn Asn Glu Arg Glu Asp Tyr
            20                  25                  30

Asp Ala Ser Gln His Ala Ala Met Val Ala Val Asn Leu Ile Ser Ser
        35                  40                  45

Ala Arg Val Ile Leu Lys Leu Asp Ala Val Tyr Thr Glu Tyr Ser Ala
    50                  55                  60

Gln Tyr Leu Val Asp Asn Ala Gly Lys Glu Asp Asn Gln Gly Glu Met
65                  70                  75                  80

Asp Gln Gln Ser Ser Gln Leu Thr Leu Gln Asn Leu Leu Gln Tyr Met
                85                  90                  95

Asp Glu Asn Val Trp Asn Lys Lys Glu Asp Val Gln Gly Glu Arg Glu
            100                 105                 110

Gln Pro Leu Thr Val Lys Asp Cys Leu Glu Cys Ala Phe Lys
        115                 120                 125

<210> SEQ ID NO 17
<211> LENGTH: 252
<212> TYPE: PRT
<213> ORGANISM: Arabidopsis thaliana

<400> SEQUENCE: 17

Met Asn Met Ile Gln Arg Phe Met Gln Ser Met Ala Lys Thr Arg Gly
1               5                   10                  15

Leu Cys His Pro Asp Cys Val Lys Ala Ser Ser Glu Gln Glu Asp Tyr
            20                  25                  30

Asp Ala Ser Gln Leu Ser Ile Trp Trp Ile Met Leu Gly Arg Lys Thr
        35                  40                  45

Thr Arg Glu Lys Trp Met Asn Gln Ala Leu Ser Ser Leu Ser Lys Thr
```

```
            50                  55                  60
Cys Ile Ser Ile Trp Trp Lys Met Ser Gly Ile Arg Gly Lys Met Cys
 65                  70                  75                  80

Arg Glu Arg Glu Gln Pro Leu Thr Val Lys Asp Cys Leu Glu Cys Ala
                 85                  90                  95

Phe Lys Lys Gly Leu Pro Arg Arg Glu His Trp Ala His Val Gly Cys
            100                 105                 110

Thr Phe Lys Ala Pro Pro Phe Ala Cys His Ile Pro Arg Val Pro Met
        115                 120                 125

Lys Gly Glu Val Ile Glu Thr Lys Ser Leu Asp Glu Ala Phe Lys Leu
    130                 135                 140

Leu Ile Lys Gln Pro Val Gly Ala Arg Leu His Val Phe Ser Pro Asp
145                 150                 155                 160

Leu Asp Asn Val Gly Glu Gly Val Tyr Glu Gly Leu Ser Ser Leu Ser
                165                 170                 175

Arg Lys Glu Ser Arg Tyr Val Gly Leu Arg Asp Val Ile Ile Val Ala
            180                 185                 190

Val Asn Lys Ser Glu Gly Lys Thr Val Ala Thr Val Lys Ile Cys Tyr
        195                 200                 205

Lys Lys Lys Thr Ser Phe Val Lys Val Cys Leu Ser Arg Met Phe Val
    210                 215                 220

Gln Leu Gly Gly Gly Glu Glu Ser Gln Val Lys Glu Pro Thr Gly Leu
225                 230                 235                 240

Leu Val Asp Phe Cys Ile Pro Arg Leu Ser Ile Asn
                245                 250

<210> SEQ ID NO 18
<211> LENGTH: 178
<212> TYPE: PRT
<213> ORGANISM: Arabidopsis thaliana

<400> SEQUENCE: 18

Met Ala Leu Pro Pro Tyr Asp Pro Asn Phe Thr Leu Ala Phe Ser Tyr
 1               5                  10                  15

Gly Arg Arg Asp Asn Val Phe Glu Asn Asp Pro Glu His Asp Glu Ser
            20                  25                  30

Ala Ser Ala Ala Ile Val Ala Val Glu Leu Ile Ser Ser Ala Arg Leu
        35                  40                  45

Ala Leu Lys Leu Asp Ser Val Arg Thr Glu Tyr Ser Ala Gln Tyr Leu
    50                  55                  60

Val Asp Lys Ala Gly Ser Arg Asn Leu Arg Arg Arg Lys Leu Thr
 65                  70                  75                  80

Val Lys Asp Cys Leu Asn Phe Ala Leu Lys Lys Gly Gly Ile Pro Arg
                 85                  90                  95

Ala Glu Asp Trp Pro Pro Leu Gly Ser Glu Ser Lys Thr Pro Ser Ser
            100                 105                 110

Tyr Glu Pro Ala Leu Val Ser Met Lys Gly Glu Val Ile Glu Pro Lys
        115                 120                 125

Asp Met Asp Glu Val Pro Glu Leu Leu Val His Gln Ser Ala Val Gly
    130                 135                 140

Ala Lys Leu His Val Phe Thr Pro His Ile Glu Leu Gln Gln Asp Ala
145                 150                 155                 160

Ile Tyr Leu Pro Arg Gln Val Ser Met Arg Ala Thr Leu Asp Leu Glu
                165                 170                 175
```

Met Gly

<210> SEQ ID NO 19
<211> LENGTH: 239
<212> TYPE: PRT
<213> ORGANISM: Arabidopsis thaliana

<400> SEQUENCE: 19

```
Met Ala Leu Pro Pro Tyr Asp Pro Asn Phe Lys Phe Ala Phe Ser Leu
1               5                   10                  15

Gly Thr Ile Ala Lys His Gln Asp Tyr Asp Glu Ser Ala Ser Ala Ala
            20                  25                  30

Val Val Ala Leu Asp Leu Ile Ser Ala Arg Phe Ala Leu Lys Leu
        35                  40                  45

Asp Ser Val Tyr Thr Glu Tyr Ser Ala Lys Tyr Val Val Asp Asn Ala
    50                  55                  60

Ala Gly Ser His Ser Gly Arg Lys Leu Thr Val Lys Asp Cys Leu Glu
65                  70                  75                  80

Phe Ala Leu Asn Lys Gly Gly Ile Pro Lys Ala Glu Asp Trp Pro Arg
                85                  90                  95

Leu Gly Ser Val Ile Thr Pro Pro Ser Ser Tyr Lys Pro Asp Leu Val
            100                 105                 110

Ser Met Lys Gly Gln Val Ile Glu Pro Gln Thr Ile Glu Glu Ala Cys
        115                 120                 125

Asp Met Val Val Asp Gln Pro Val Gly Ala Lys Leu His Val Phe Lys
130                 135                 140

Pro His Ile Glu Leu Gln Gln Asp Ala Ser Ala Ile Thr Gly Ile Tyr
145                 150                 155                 160

Cys Gly Thr Ser Gly Glu Pro Ala Ser Tyr Val Gly Leu Arg Asp Ala
                165                 170                 175

Ile Ile Val Gly Val Glu Lys Ile Gln Gly Lys Ser Ile Gly Thr Val
            180                 185                 190

Lys Val Trp Tyr Lys Lys Phe Ile Phe Leu Lys Val Ala Met Ser Arg
        195                 200                 205

Trp Phe Gln Leu Tyr Ser Pro Asp Gly Thr His Thr Gly Ile Lys Arg
    210                 215                 220

Thr Asp Tyr Leu Val Asp Phe Cys Val Pro Arg Leu Ser Met Asp
225                 230                 235
```

<210> SEQ ID NO 20
<211> LENGTH: 25
<212> TYPE: DNA
<213> ORGANISM: Brassica napus

<400> SEQUENCE: 20
tagattctgc tgagagagcc gctac                                   25

<210> SEQ ID NO 21
<211> LENGTH: 36
<212> TYPE: DNA
<213> ORGANISM: Artificial Sequence
<220> FEATURE:
<223> OTHER INFORMATION: artificial primer to target Brassica napus
      BnaC03g77540D

<400> SEQUENCE: 21
ggatccgtcg acgcacctat gggtccatgc tttaac                       36

<210> SEQ ID NO 22
<211> LENGTH: 20
<212> TYPE: DNA
<213> ORGANISM: Brassica napus

<400> SEQUENCE: 22
tcatccagat tgccaacgag                                           20

<210> SEQ ID NO 23
<211> LENGTH: 33
<212> TYPE: DNA
<213> ORGANISM: Artificial Sequence
<220> FEATURE:
<223> OTHER INFORMATION: artificial primer to target Brassica napus
      BnaA08g12920D

<400> SEQUENCE: 23
ggatccgtcg acacgcatcc tccagtgtct tag                             33

<210> SEQ ID NO 24
<211> LENGTH: 20
<212> TYPE: DNA
<213> ORGANISM: Streptomyces hygroscopicus

<400> SEQUENCE: 24
tacacagcca tcggtccaga                                           20

<210> SEQ ID NO 25
<211> LENGTH: 21
<212> TYPE: DNA
<213> ORGANISM: Streptomyces hygroscopicus

<400> SEQUENCE: 25
gtaggagggc gtggatatgt c                                         21

<210> SEQ ID NO 26
<211> LENGTH: 22
<212> TYPE: DNA
<213> ORGANISM: Brassica napus

<400> SEQUENCE: 26
cgctacgagg cacgtactca at                                        22

<210> SEQ ID NO 27
<211> LENGTH: 19
<212> TYPE: DNA
<213> ORGANISM: Brassica napus

<400> SEQUENCE: 27
ctcggtcttc cccggtttc                                            19

<210> SEQ ID NO 28
<211> LENGTH: 24
<212> TYPE: DNA
<213> ORGANISM: Brassica napus

<400> SEQUENCE: 28
gcttagagac gtgatcctgg tagc                                      24

<210> SEQ ID NO 29
<211> LENGTH: 21
<212> TYPE: DNA
<213> ORGANISM: Brassica napus

<400> SEQUENCE: 29

```
ccagtgtggt gaacatacgg c                                              21

<210> SEQ ID NO 30
<211> LENGTH: 24
<212> TYPE: DNA
<213> ORGANISM: Brassica napus

<400> SEQUENCE: 30
gttttgttgg tctcttctct ttgc                                           24

<210> SEQ ID NO 31
<211> LENGTH: 23
<212> TYPE: DNA
<213> ORGANISM: Brassica napus

<400> SEQUENCE: 31
ttcttaagag gcgtttcaga tgg                                            23

<210> SEQ ID NO 32
<211> LENGTH: 22
<212> TYPE: DNA
<213> ORGANISM: Brassica napus

<400> SEQUENCE: 32
tgatttgggt tttgcctgat ac                                             22

<210> SEQ ID NO 33
<211> LENGTH: 24
<212> TYPE: DNA
<213> ORGANISM: Brassica napus

<400> SEQUENCE: 33
gaaacaaacc ataaatgagt tgcc                                           24

<210> SEQ ID NO 34
<211> LENGTH: 22
<212> TYPE: DNA
<213> ORGANISM: Brassica napus

<400> SEQUENCE: 34
catttgggat gtgtcgattg ag                                             22

<210> SEQ ID NO 35
<211> LENGTH: 20
<212> TYPE: DNA
<213> ORGANISM: Brassica napus

<400> SEQUENCE: 35
cccacgtagc ttgttccgtt                                                20

<210> SEQ ID NO 36
<211> LENGTH: 21
<212> TYPE: DNA
<213> ORGANISM: Brassica napus

<400> SEQUENCE: 36
aacactgtca cgcagattgc c                                              21

<210> SEQ ID NO 37
<211> LENGTH: 24
<212> TYPE: DNA
<213> ORGANISM: Brassica napus
```

```
<400> SEQUENCE: 37
ctgtccaggt tagctaccat acga                                              24

<210> SEQ ID NO 38
<211> LENGTH: 22
<212> TYPE: DNA
<213> ORGANISM: Brassica napus

<400> SEQUENCE: 38
cggtatccaa ctcattcgaa gg                                                22

<210> SEQ ID NO 39
<211> LENGTH: 24
<212> TYPE: DNA
<213> ORGANISM: Brassica napus

<400> SEQUENCE: 39
tcaagtatat actgggttgg ctgc                                              24

<210> SEQ ID NO 40
<211> LENGTH: 278
<212> TYPE: PRT
<213> ORGANISM: Artificial Sequence
<220> FEATURE:
<223> OTHER INFORMATION: Translation of atg5g18065, omitting premature
      stop codon

<400> SEQUENCE: 40

Met Asp Met Asn Gln Leu Phe Met Gln Ser Ile Ala Asn Ser Arg Gly
1               5                   10                  15

Leu Cys His Pro Asp Cys Glu Lys Ala Asn Asn Glu Arg Glu Asp Tyr
            20                  25                  30

Asp Ala Ser Gln His Ala Ala Met Val Ala Val Asn Leu Ile Ser Ser
        35                  40                  45

Ala Arg Val Ile Leu Lys Leu Asp Ala Val Tyr Thr Glu Tyr Ser Ala
    50                  55                  60

Gln Tyr Leu Val Asp Asn Ala Gly Lys Glu Asp Asn Gln Gly Glu Met
65                  70                  75                  80

Asp Gln Gln Ser Ser Gln Leu Thr Leu Gln Asn Leu Leu Gln Tyr Met
                85                  90                  95

Asp Glu Asn Val Trp Asn Lys Lys Glu Asp Val Gln Gly Glu Arg Glu
            100                 105                 110

Gln Pro Leu Thr Val Lys Asp Cys Leu Glu Cys Ala Phe Lys Gly Leu
        115                 120                 125

Pro Arg Ser Glu Gln Trp Ala His Val Gly Cys Pro Phe Lys Ala Pro
    130                 135                 140

Pro Phe Ala Cys Gln Ile Pro Arg Val Pro Met Lys Gly Glu Val Ile
145                 150                 155                 160

Glu Thr Lys Ser Leu Asp Glu Ala Phe Lys Leu Leu Ile Lys Gln Pro
                165                 170                 175

Val Gly Ala Arg Leu His Val Phe Ser Pro Glu Leu Asp Asn Val Gly
            180                 185                 190

Glu Gly Phe Tyr Glu Gly Leu Ser Ser Gln Ser Ser Lys Glu Ser Arg
        195                 200                 205

Tyr Val Gly Leu Arg Asp Val Ile Ile Val Ala Val Asp Lys Ser Glu
    210                 215                 220

Gly Lys Thr Val Ala Thr Val Lys Ile Cys Tyr Lys Lys Lys Thr Ser
225                 230                 235                 240
```

-continued

```
Phe Val Lys Val Leu Val Ser Arg Met Phe Val Leu Gly Gly Gly Glu
                245                 250                 255

Glu Ser Gln Val Lys Glu Pro Ala Gly Leu Leu Val Asp Phe Cys Ile
            260                 265                 270

Pro Arg Leu Ser Val Asn
        275

<210> SEQ ID NO 41
<211> LENGTH: 341
<212> TYPE: PRT
<213> ORGANISM: Artificial Sequence
<220> FEATURE:
<223> OTHER INFORMATION: Arabidopsis thaliana Kanghan consensus sequence
      (greater than or equal to 90% consensus)
<220> FEATURE:
<221> NAME/KEY: MISC_FEATURE
<222> LOCATION: (1)..(55)
<223> OTHER INFORMATION: Xaa is an unknown amino acid
<220> FEATURE:
<221> NAME/KEY: MISC_FEATURE
<222> LOCATION: (56)..(56)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (57)..(57)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (58)..(58)
<223> OTHER INFORMATION: Xaa is an unknown amino acid
<220> FEATURE:
<221> NAME/KEY: MISC_FEATURE
<222> LOCATION: (59)..(59)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (60)..(60)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (61)..(61)
<223> OTHER INFORMATION: Xaa is Arg, Gly, or Ser
<220> FEATURE:
<221> NAME/KEY: MISC_FEATURE
<222> LOCATION: (62)..(63)
<223> OTHER INFORMATION: Each Xaa is an unknown amino acid
<220> FEATURE:
<221> NAME/KEY: MISC_FEATURE
<222> LOCATION: (64)..(64)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (65)..(79)
<223> OTHER INFORMATION: Each Xaa is an unknown amino acid
<220> FEATURE:
<221> NAME/KEY: MISC_FEATURE
<222> LOCATION: (80)..(80)
<223> OTHER INFORMATION: Xaa is Asp or Glu
<220> FEATURE:
<221> NAME/KEY: MISC_FEATURE
<222> LOCATION: (81)..(81)
<223> OTHER INFORMATION: Xaa is Phe, His, Trp, Tyr
<220> FEATURE:
<221> NAME/KEY: MISC_FEATURE
<222> LOCATION: (82)..(82)
<223> OTHER INFORMATION: Xaa is Asp, Glu, His, Lys, or Arg
<220> FEATURE:
<221> NAME/KEY: MISC_FEATURE
<222> LOCATION: (83)..(83)
<223> OTHER INFORMATION: Xaa is Ala, Cys, Asp, Glu, Gly, His, Lys, Asn,
```

```
      Gln, Arg, Ser, or Thr
<220> FEATURE:
<221> NAME/KEY: MISC_FEATURE
<222> LOCATION: (84)..(84)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (85)..(85)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (86)..(94)
<223> OTHER INFORMATION: Each Xaa is an unknown amino acid
<220> FEATURE:
<221> NAME/KEY: MISC_FEATURE
<222> LOCATION: (95)..(95)
<223> OTHER INFORMATION: Xaa is Ile, Leu, or Val
<220> FEATURE:
<221> NAME/KEY: MISC_FEATURE
<222> LOCATION: (97)..(97)
<223> OTHER INFORMATION: Xaa is an unknown amino acid
<220> FEATURE:
<221> NAME/KEY: MISC_FEATURE
<222> LOCATION: (98)..(102)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (103)..(103)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (104)..(104)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (105)..(105)
<223> OTHER INFORMATION: Xaa is Asp, Glu, His, Lys, or Arg
<220> FEATURE:
<221> NAME/KEY: MISC_FEATURE
<222> LOCATION: (106)..(106)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (107)..(107)
<223> OTHER INFORMATION: Xaa is an unknown amino acid
<220> FEATURE:
<221> NAME/KEY: MISC_FEATURE
<222> LOCATION: (108)..(108)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (109)..(109)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (110)..(110)
<223> OTHER INFORMATION: Xaa is Asp, Glu, His, Lys, or Arg
<220> FEATURE:
<221> NAME/KEY: MISC_FEATURE
<222> LOCATION: (111)..(111)
<223> OTHER INFORMATION: Xaa is Phe, His, Trp, Tyr
<220> FEATURE:
<221> NAME/KEY: MISC_FEATURE
<222> LOCATION: (112)..(112)
<223> OTHER INFORMATION: Xaa is an unknown amino acid
<220> FEATURE:
<221> NAME/KEY: MISC_FEATURE
<222> LOCATION: (113)..(113)
<223> OTHER INFORMATION: Xaa is Ala, Cys, Asp, Gly, Asn, Pro, Ser, Thr,
      or Val
<220> FEATURE:
```

```
<221> NAME/KEY: MISC_FEATURE
<222> LOCATION: (114)..(114)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (115)..(115)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (116)..(116)
<223> OTHER INFORMATION: Xaa is Ile, Leu, or Val
<220> FEATURE:
<221> NAME/KEY: MISC_FEATURE
<222> LOCATION: (117)..(167)
<223> OTHER INFORMATION: Each Xaa is an unknown amino acid
<220> FEATURE:
<221> NAME/KEY: MISC_FEATURE
<222> LOCATION: (168)..(168)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (174)..(174)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (175)..(175)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (176)..(176)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (178)..(178)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (179)..(179)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (180)..(341)
<223> OTHER INFORMATION: Each Xaa is an unknown amino acid

<400> SEQUENCE: 41

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Ser
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
```

```
                130             135                140
Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Thr Val Lys Asp Cys Xaa Xaa Xaa
                165                 170                 175

Ala Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa
                340

<210> SEQ ID NO 42
<211> LENGTH: 292
<212> TYPE: PRT
<213> ORGANISM: Artificial Sequence
<220> FEATURE:
<223> OTHER INFORMATION: Arabidopsis thaliana Kanghan 80% consensus
      sequence
<220> FEATURE:
<221> NAME/KEY: MISC_FEATURE
<222> LOCATION: (1)..(6)
<223> OTHER INFORMATION: Each Xaa is an unknown amino acid
<220> FEATURE:
<221> NAME/KEY: MISC_FEATURE
<222> LOCATION: (7)..(7)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (8)..(10)
<223> OTHER INFORMATION: Each Xaa is an unknown amino acid
<220> FEATURE:
<221> NAME/KEY: MISC_FEATURE
<222> LOCATION: (11)..(13)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (14)..(14)
<223> OTHER INFORMATION: Xaa is an unknown amino acid
<220> FEATURE:
<221> NAME/KEY: MISC_FEATURE
<222> LOCATION: (16)..(16)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (17)..(17)
```

```
<223> OTHER INFORMATION: Xaa is Arg, Gly, or Ser
<220> FEATURE:
<221> NAME/KEY: MISC_FEATURE
<222> LOCATION: (18)..(18)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (19)..(19)
<223> OTHER INFORMATION: Xaa is an unknown amino acid
<220> FEATURE:
<221> NAME/KEY: MISC_FEATURE
<222> LOCATION: (20)..(20)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (21)..(21)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (22)..(23)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (24)..(24)
<223> OTHER INFORMATION: Xaa is Asp, Glu, His, Lys, or Arg
<220> FEATURE:
<221> NAME/KEY: MISC_FEATURE
<222> LOCATION: (25)..(25)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (27)..(32)
<223> OTHER INFORMATION: Each Xaa is an unknown amino acid
<220> FEATURE:
<221> NAME/KEY: MISC_FEATURE
<222> LOCATION: (33)..(33)
<223> OTHER INFORMATION: Xaa is Asp, Glu, His, Lys, or Arg
<220> FEATURE:
<221> NAME/KEY: MISC_FEATURE
<222> LOCATION: (34)..(35)
<223> OTHER INFORMATION: Each Xaa is Cys, Asp, Glu, His, Lys, Asn, Gln,
      Arg, Ser, or Thr
<220> FEATURE:
<221> NAME/KEY: MISC_FEATURE
<222> LOCATION: (39)..(39)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (41)..(41)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (42)..(42)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (45)..(45)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (48)..(48)
<223> OTHER INFORMATION: Xaa is Ile, Leu, or Val
<220> FEATURE:
<221> NAME/KEY: MISC_FEATURE
<222> LOCATION: (49)..(49)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (56)..(56)
```

```
<223> OTHER INFORMATION: Xaa is Ile, Leu, or Val
<220> FEATURE:
<221> NAME/KEY: MISC_FEATURE
<222> LOCATION: (57)..(57)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (60)..(60)
<223> OTHER INFORMATION: Xaa is Ile, Leu, or Val
<220> FEATURE:
<221> NAME/KEY: MISC_FEATURE
<222> LOCATION: (62)..(62)
<223> OTHER INFORMATION: Xaa is Arg, Gly, or Ser
<220> FEATURE:
<221> NAME/KEY: MISC_FEATURE
<222> LOCATION: (63)..(64)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (69)..(69)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (71)..(71)
<223> OTHER INFORMATION: Xaa is Phe, His, Trp, Tyr
<220> FEATURE:
<221> NAME/KEY: MISC_FEATURE
<222> LOCATION: (73)..(73)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (75)..(75)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (76)..(76)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (77)..(77)
<223> OTHER INFORMATION: Xaa is Arg, Gly, or Ser
<220> FEATURE:
<221> NAME/KEY: MISC_FEATURE
<222> LOCATION: (78)..(78)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (79)..(80)
<223> OTHER INFORMATION: Each Xaa is Cys, Asp, Glu, His, Lys, Asn, Gln,
      Arg, Ser, or Thr
<220> FEATURE:
<221> NAME/KEY: MISC_FEATURE
<222> LOCATION: (81)..(118)
<223> OTHER INFORMATION: Each Xaa is an unknown amino acid
<220> FEATURE:
<221> NAME/KEY: MISC_FEATURE
<222> LOCATION: (119)..(119)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (121)..(121)
<223> OTHER INFORMATION: Xaa is an unknown amino acid
<220> FEATURE:
<221> NAME/KEY: MISC_FEATURE
<222> LOCATION: (122)..(122)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (123)..(123)
<223> OTHER INFORMATION: Xaa is an unknown amino acid
```

-continued

```
<220> FEATURE:
<221> NAME/KEY: MISC_FEATURE
<222> LOCATION: (132)..(132)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (134)..(134)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (136)..(136)
<223> OTHER INFORMATION: Xaa is an unknown amino acid
<220> FEATURE:
<221> NAME/KEY: MISC_FEATURE
<222> LOCATION: (138)..(138)
<223> OTHER INFORMATION: Xaa is an unknown amino acid
<220> FEATURE:
<221> NAME/KEY: MISC_FEATURE
<222> LOCATION: (139)..(139)
<223> OTHER INFORMATION: Xaa is Ile, Leu, or Val
<220> FEATURE:
<221> NAME/KEY: MISC_FEATURE
<222> LOCATION: (141)..(141)
<223> OTHER INFORMATION: Xaa is His, Lys, or Arg
<220> FEATURE:
<221> NAME/KEY: MISC_FEATURE
<222> LOCATION: (142)..(143)
<223> OTHER INFORMATION: Each Xaa is Ala, Cys, Asp, Glu, Gly, His, Lys,
      Asn, Gln, Arg, Ser, or Thr
<220> FEATURE:
<221> NAME/KEY: MISC_FEATURE
<222> LOCATION: (144)..(144)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (146)..(146)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (147)..(147)
<223> OTHER INFORMATION: Xaa is an unknown amino acid
<220> FEATURE:
<221> NAME/KEY: MISC_FEATURE
<222> LOCATION: (148)..(148)
<223> OTHER INFORMATION: Xaa is Ile, Leu, or Val
<220> FEATURE:
<221> NAME/KEY: MISC_FEATURE
<222> LOCATION: (150)..(150)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (151)..(154)
<223> OTHER INFORMATION: Each Xaa is an unknown amino acid
<220> FEATURE:
<221> NAME/KEY: MISC_FEATURE
<222> LOCATION: (155)..(155)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (157)..(157)
<223> OTHER INFORMATION: Xaa is an unknown amino acid
<220> FEATURE:
<221> NAME/KEY: MISC_FEATURE
<222> LOCATION: (158)..(158)
<223> OTHER INFORMATION: Xaa is Arg, Gly, or Ser
<220> FEATURE:
<221> NAME/KEY: MISC_FEATURE
<222> LOCATION: (159)..(159)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (160)..(160)
```

```
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (161)..(161)
<223> OTHER INFORMATION: Xaa is an unknown amino acid
<220> FEATURE:
<221> NAME/KEY: MISC_FEATURE
<222> LOCATION: (162)..(162)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (163)..(163)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (165)..(165)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (166)..(166)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (169)..(169)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (171)..(171)
<223> OTHER INFORMATION: Xaa is Ile, Leu, or Val
<220> FEATURE:
<221> NAME/KEY: MISC_FEATURE
<222> LOCATION: (173)..(173)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (174)..(174)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (175)..(175)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (176)..(176)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (177)..(177)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (179)..(179)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (180)..(180)
<223> OTHER INFORMATION: Xaa is an unknown amino acid
<220> FEATURE:
<221> NAME/KEY: MISC_FEATURE
<222> LOCATION: (181)..(181)
<223> OTHER INFORMATION: Xaa is Asp, Glu, His, Lys, or Arg
<220> FEATURE:
<221> NAME/KEY: MISC_FEATURE
<222> LOCATION: (182)..(184)
<223> OTHER INFORMATION: Each Xaa is Ala, Cys, Phe, Gly, His, Ile, Lys,
      Leu, Met, Arg, Thr, Val, Trp, or Tyr
<220> FEATURE:
```

```
<221> NAME/KEY: MISC_FEATURE
<222> LOCATION: (185)..(185)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (187)..(187)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (188)..(188)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (189)..(189)
<223> OTHER INFORMATION: Xaa is Arg, Gly, or Ser
<220> FEATURE:
<221> NAME/KEY: MISC_FEATURE
<222> LOCATION: (191)..(191)
<223> OTHER INFORMATION: Xaa is His, Lys, or Arg
<220> FEATURE:
<221> NAME/KEY: MISC_FEATURE
<222> LOCATION: (194)..(194)
<223> OTHER INFORMATION: Xaa is Ile, Leu, or Val
<220> FEATURE:
<221> NAME/KEY: MISC_FEATURE
<222> LOCATION: (196)..(196)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (198)..(198)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (199)..(199)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (200)..(200)
<223> OTHER INFORMATION: Xaa is Asp or Glu
<220> FEATURE:
<221> NAME/KEY: MISC_FEATURE
<222> LOCATION: (201)..(202)
<223> OTHER INFORMATION: Each Xaa is an unknown amino acid
<220> FEATURE:
<221> NAME/KEY: MISC_FEATURE
<222> LOCATION: (203)..(203)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (204)..(204)
<223> OTHER INFORMATION: Xaa is Asp or Glu
<220> FEATURE:
<221> NAME/KEY: MISC_FEATURE
<222> LOCATION: (205)..(205)
<223> OTHER INFORMATION: Xaa is Arg, Gly, or Ser
<220> FEATURE:
<221> NAME/KEY: MISC_FEATURE
<222> LOCATION: (206)..(206)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (208)..(208)
<223> OTHER INFORMATION: Xaa is an unknown amino acid
<220> FEATURE:
<221> NAME/KEY: MISC_FEATURE
<222> LOCATION: (209)..(209)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (210)..(218)
```

```
<223> OTHER INFORMATION: Each Xaa is an unknown amino acid
<220> FEATURE:
<221> NAME/KEY: MISC_FEATURE
<222> LOCATION: (219)..(219)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (220)..(220)
<223> OTHER INFORMATION: Xaa is an unknown amino acid
<220> FEATURE:
<221> NAME/KEY: MISC_FEATURE
<222> LOCATION: (222)..(222)
<223> OTHER INFORMATION: Xaa is Arg, Gly, or Ser
<220> FEATURE:
<221> NAME/KEY: MISC_FEATURE
<222> LOCATION: (223)..(223)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (225)..(226)
<223> OTHER INFORMATION: Each Xaa is Ala, Cys, Asp, Gly, Asn, Pro, Ser,
      Thr, or Val
<220> FEATURE:
<221> NAME/KEY: MISC_FEATURE
<222> LOCATION: (227)..(227)
<223> OTHER INFORMATION: Xaa is Ile, Leu, or Val
<220> FEATURE:
<221> NAME/KEY: MISC_FEATURE
<222> LOCATION: (228)..(228)
<223> OTHER INFORMATION: Xaa is an unknown amino acid
<220> FEATURE:
<221> NAME/KEY: MISC_FEATURE
<222> LOCATION: (229)..(229)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (230)..(230)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (231)..(231)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (232)..(232)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (233)..(292)
<223> OTHER INFORMATION: Each Xaa is an unknown amino acid

<400> SEQUENCE: 42

Xaa Xaa Xaa Xaa Xaa Xaa Xaa Xaa Xaa Xaa Xaa Xaa Xaa Xaa Ser Xaa
1               5                   10                  15

Xaa Xaa Xaa Xaa Xaa Xaa Xaa Xaa Asp Xaa Xaa Xaa Xaa Xaa
            20                  25                  30

Xaa Xaa Xaa Asp Tyr Asp Xaa Ser Xaa Xaa Ala Ala Xaa Val Ala Xaa
        35                  40                  45

Xaa Leu Ile Ser Ser Ala Arg Xaa Xaa Leu Lys Xaa Asp Xaa Xaa Xaa
    50                  55                  60

Thr Glu Tyr Ser Xaa Gln Xaa Leu Xaa Asp Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110
```

```
Xaa Xaa Xaa Xaa Xaa Xaa Xaa Arg Xaa Xaa Xaa Leu Thr Val Lys Asp
        115                 120                 125

Cys Leu Glu Xaa Ala Xaa Lys Xaa Gly Xaa Xaa Pro Xaa Xaa Xaa Xaa
130                 135                 140

Trp Xaa Xaa Xaa Gly Xaa Xaa Xaa Xaa Xaa Pro Xaa Xaa Xaa Xaa Xaa
145                 150                 155                 160

Xaa Xaa Xaa Val Xaa Xaa Lys Gly Xaa Val Xaa Glu Xaa Xaa Xaa Xaa
                165                 170                 175

Xaa Glu Xaa Xaa Xaa Xaa Xaa Xaa Gln Xaa Xaa Xaa Ala Xaa Leu
        180                 185                 190

His Xaa Phe Xaa Pro Xaa Xaa Xaa Xaa Xaa Xaa Xaa Xaa Tyr Xaa
        195                 200                 205

Xaa Xaa Xaa Xaa Xaa Xaa Xaa Xaa Xaa Xaa Xaa Val Xaa Xaa Arg
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa
        290

<210> SEQ ID NO 43
<211> LENGTH: 287
<212> TYPE: PRT
<213> ORGANISM: Artificial Sequence
<220> FEATURE:
<223> OTHER INFORMATION: Arabidopsis thaliana Kanghan 70% consensus
      sequence
<220> FEATURE:
<221> NAME/KEY: MISC_FEATURE
<222> LOCATION: (1)..(5)
<223> OTHER INFORMATION: Each Xaa is an unknown amino acid
<220> FEATURE:
<221> NAME/KEY: MISC_FEATURE
<222> LOCATION: (6)..(6)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (7)..(7)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (8)..(8)
<223> OTHER INFORMATION: Xaa is an unknown amino acid
<220> FEATURE:
<221> NAME/KEY: MISC_FEATURE
<222> LOCATION: (9)..(9)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (10)..(11)
<223> OTHER INFORMATION: Each Xaa is Cys, Asp, Glu, His, Lys, Asn, Gln,
      Arg, Ser, or Thr
<220> FEATURE:
<221> NAME/KEY: MISC_FEATURE
<222> LOCATION: (12)..(13)
<223> OTHER INFORMATION: Each Xaa is Ala, Cys, Phe, Gly, His, Ile, Lys,
      Leu, Met, Arg, Thr, Val, Trp, or Tyr
<220> FEATURE:
```

```
<221> NAME/KEY: MISC_FEATURE
<222> LOCATION: (14)..(14)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (16)..(16)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (17)..(17)
<223> OTHER INFORMATION: Xaa is Arg, Gly, or Ser
<220> FEATURE:
<221> NAME/KEY: MISC_FEATURE
<222> LOCATION: (18)..(18)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (19)..(19)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (20)..(20)
<223> OTHER INFORMATION: Xaa is Asp, Glu, His, Lys, or Arg
<220> FEATURE:
<221> NAME/KEY: MISC_FEATURE
<222> LOCATION: (22)..(22)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (28)..(28)
<223> OTHER INFORMATION: Xaa is an unknown amino acid
<220> FEATURE:
<221> NAME/KEY: MISC_FEATURE
<222> LOCATION: (31)..(32)
<223> OTHER INFORMATION: Each Xaa is Ala, Cys, Asp, Gly, Asn, Pro, Ser,
      Thr, or Val
<220> FEATURE:
<221> NAME/KEY: MISC_FEATURE
<222> LOCATION: (34)..(34)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (42)..(42)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (45)..(45)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (49)..(49)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (56)..(56)
<223> OTHER INFORMATION: Xaa is Ile, Leu, or Val
<220> FEATURE:
<221> NAME/KEY: MISC_FEATURE
<222> LOCATION: (57)..(57)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (62)..(62)
<223> OTHER INFORMATION: Xaa is Arg, Gly, or Ser
<220> FEATURE:
<221> NAME/KEY: MISC_FEATURE
<222> LOCATION: (63)..(63)
<223> OTHER INFORMATION: Xaa is Ala, Cys, Asp, Gly, Asn, Pro, Ser, Thr,
      or Val
```

```
<220> FEATURE:
<221> NAME/KEY: MISC_FEATURE
<222> LOCATION: (64)..(64)
<223> OTHER INFORMATION: Xaa is Phe, His, Trp, Tyr
<220> FEATURE:
<221> NAME/KEY: MISC_FEATURE
<222> LOCATION: (78)..(78)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (79)..(80)
<223> OTHER INFORMATION: Each Xaa is Asp, Glu, His, Lys, or Arg
<220> FEATURE:
<221> NAME/KEY: MISC_FEATURE
<222> LOCATION: (81)..(81)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (82)..(95)
<223> OTHER INFORMATION: Each Xaa is an unknown amino acid
<220> FEATURE:
<221> NAME/KEY: MISC_FEATURE
<222> LOCATION: (96)..(96)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (97)..(97)
<223> OTHER INFORMATION: Xaa is an unknown amino acid
<220> FEATURE:
<221> NAME/KEY: MISC_FEATURE
<222> LOCATION: (99)..(99)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (100)..(101)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (102)..(102)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (103)..(103)
<223> OTHER INFORMATION: Xaa is an unknown amino acid
<220> FEATURE:
<221> NAME/KEY: MISC_FEATURE
<222> LOCATION: (104)..(104)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (105)..(105)
<223> OTHER INFORMATION: Xaa is Ile, Leu, or Val
<220> FEATURE:
<221> NAME/KEY: MISC_FEATURE
<222> LOCATION: (107)..(107)
<223> OTHER INFORMATION: Xaa is an unknown amino acid
<220> FEATURE:
<221> NAME/KEY: MISC_FEATURE
<222> LOCATION: (109)..(109)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (110)..(110)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (111)..(111)
<223> OTHER INFORMATION: Xaa is Ala, Cys, Asp, Gly, Asn, Pro, Ser, Thr,
      or Val
<220> FEATURE:
```

```
<221> NAME/KEY: MISC_FEATURE
<222> LOCATION: (112)..(112)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (113)..(113)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (114)..(114)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (115)..(118)
<223> OTHER INFORMATION: Each Xaa is an unknown amino acid
<220> FEATURE:
<221> NAME/KEY: MISC_FEATURE
<222> LOCATION: (119)..(119)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (121)..(121)
<223> OTHER INFORMATION: Xaa is Asp, Glu, His, Lys, or Arg
<220> FEATURE:
<221> NAME/KEY: MISC_FEATURE
<222> LOCATION: (122)..(122)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (123)..(123)
<223> OTHER INFORMATION: Xaa is an unknown amino acid
<220> FEATURE:
<221> NAME/KEY: MISC_FEATURE
<222> LOCATION: (132)..(132)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (138)..(138)
<223> OTHER INFORMATION: Xaa is Ile, Leu, or Val
<220> FEATURE:
<221> NAME/KEY: MISC_FEATURE
<222> LOCATION: (141)..(141)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (143)..(143)
<223> OTHER INFORMATION: Xaa is Asp, Glu, His, Lys, or Arg
<220> FEATURE:
<221> NAME/KEY: MISC_FEATURE
<222> LOCATION: (145)..(145)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (146)..(146)
<223> OTHER INFORMATION: Xaa is His, Lys, or Arg
<220> FEATURE:
<221> NAME/KEY: MISC_FEATURE
<222> LOCATION: (147)..(147)
<223> OTHER INFORMATION: Xaa is Ile, Leu, or Val
<220> FEATURE:
<221> NAME/KEY: MISC_FEATURE
<222> LOCATION: (149)..(149)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (150)..(150)
<223> OTHER INFORMATION: Xaa is an unknown amino acid
<220> FEATURE:
<221> NAME/KEY: MISC_FEATURE
<222> LOCATION: (151)..(151)
```

```
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (152)..(152)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (153)..(153)
<223> OTHER INFORMATION: Xaa is an unknown amino acid
<220> FEATURE:
<221> NAME/KEY: MISC_FEATURE
<222> LOCATION: (156)..(156)
<223> OTHER INFORMATION: Xaa is an unknown amino acid
<220> FEATURE:
<221> NAME/KEY: MISC_FEATURE
<222> LOCATION: (157)..(157)
<223> OTHER INFORMATION: Xaa is Arg, Gly, or Ser
<220> FEATURE:
<221> NAME/KEY: MISC_FEATURE
<222> LOCATION: (158)..(158)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (159)..(159)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (160)..(160)
<223> OTHER INFORMATION: Xaa is an unknown amino acid
<220> FEATURE:
<221> NAME/KEY: MISC_FEATURE
<222> LOCATION: (161)..(161)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (162)..(162)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (164)..(164)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (172)..(172)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (173)..(173)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (174)..(174)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (175)..(175)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (176)..(176)
<223> OTHER INFORMATION: Xaa is Asp or Glu
<220> FEATURE:
<221> NAME/KEY: MISC_FEATURE
<222> LOCATION: (179)..(179)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
```

```
<222> LOCATION: (180)..(180)
<223> OTHER INFORMATION: Xaa is Asp, Glu, His, Lys, or Arg
<220> FEATURE:
<221> NAME/KEY: MISC_FEATURE
<222> LOCATION: (182)..(183)
<223> OTHER INFORMATION: Each Xaa is Ile, Leu, or Val
<220> FEATURE:
<221> NAME/KEY: MISC_FEATURE
<222> LOCATION: (184)..(184)
<223> OTHER INFORMATION: Xaa is Asp, Glu, His, Lys, or Arg
<220> FEATURE:
<221> NAME/KEY: MISC_FEATURE
<222> LOCATION: (187)..(187)
<223> OTHER INFORMATION: Xaa is Ile, Leu, or Val
<220> FEATURE:
<221> NAME/KEY: MISC_FEATURE
<222> LOCATION: (190)..(190)
<223> OTHER INFORMATION: Xaa is His, Lys, or Arg
<220> FEATURE:
<221> NAME/KEY: MISC_FEATURE
<222> LOCATION: (193)..(193)
<223> OTHER INFORMATION: Xaa is Ile, Leu, or Val
<220> FEATURE:
<221> NAME/KEY: MISC_FEATURE
<222> LOCATION: (195)..(195)
<223> OTHER INFORMATION: Xaa is Ser or Thr
<220> FEATURE:
<221> NAME/KEY: MISC_FEATURE
<222> LOCATION: (197)..(197)
<223> OTHER INFORMATION: Xaa is Asp, Glu, His, Lys, or Arg
<220> FEATURE:
<221> NAME/KEY: MISC_FEATURE
<222> LOCATION: (198)..(198)
<223> OTHER INFORMATION: Xaa is Ile, Leu, or Val
<220> FEATURE:
<221> NAME/KEY: MISC_FEATURE
<222> LOCATION: (199)..(199)
<223> OTHER INFORMATION: Xaa is Asp or Glu
<220> FEATURE:
<221> NAME/KEY: MISC_FEATURE
<222> LOCATION: (200)..(201)
<223> OTHER INFORMATION: Each Xaa is an unknown amino acid
<220> FEATURE:
<221> NAME/KEY: MISC_FEATURE
<222> LOCATION: (202)..(202)
<223> OTHER INFORMATION: Xaa is Ala, Cys, Asp, Glu, Gly, His, Lys, Asn,
    Gln, Arg, Ser, or Thr
<220> FEATURE:
<221> NAME/KEY: MISC_FEATURE
<222> LOCATION: (203)..(203)
<223> OTHER INFORMATION: Xaa is Asp or Glu
<220> FEATURE:
<221> NAME/KEY: MISC_FEATURE
<222> LOCATION: (205)..(205)
<223> OTHER INFORMATION: Xaa is Ile, Leu, or Val
<220> FEATURE:
<221> NAME/KEY: MISC_FEATURE
<222> LOCATION: (207)..(207)
<223> OTHER INFORMATION: Xaa is Cys, Asp, Glu, His, Lys, Asn, Gln, Arg,
    Ser, or Thr
<220> FEATURE:
<221> NAME/KEY: MISC_FEATURE
<222> LOCATION: (209)..(209)
<223> OTHER INFORMATION: Xaa is an unknown amino acid
<220> FEATURE:
<221> NAME/KEY: MISC_FEATURE
<222> LOCATION: (210)..(211)
<223> OTHER INFORMATION: Each Xaa is Ala, Cys, Asp, Gly, Asn, Pro, Ser,
    Thr, or Val
<220> FEATURE:
<221> NAME/KEY: MISC_FEATURE
<222> LOCATION: (212)..(212)
<223> OTHER INFORMATION: Xaa is an unknown amino acid
<220> FEATURE:
<221> NAME/KEY: MISC_FEATURE
<222> LOCATION: (213)..(213)
<223> OTHER INFORMATION: Xaa is Cys, Asp, Glu, His, Lys, Asn, Gln, Arg,
    Ser, or Thr
<220> FEATURE:
```

```
<221> NAME/KEY: MISC_FEATURE
<222> LOCATION: (214)..(214)
<223> OTHER INFORMATION: Xaa is an unknown amino acid
<220> FEATURE:
<221> NAME/KEY: MISC_FEATURE
<222> LOCATION: (215)..(215)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (216)..(216)
<223> OTHER INFORMATION: Xaa is His, Lys, or Arg
<220> FEATURE:
<221> NAME/KEY: MISC_FEATURE
<222> LOCATION: (223)..(223)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (224)..(224)
<223> OTHER INFORMATION: Xaa is Ile, Leu, or Val
<220> FEATURE:
<221> NAME/KEY: MISC_FEATURE
<222> LOCATION: (225)..(225)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (226)..(226)
<223> OTHER INFORMATION: Xaa is Ile, Leu, or Val
<220> FEATURE:
<221> NAME/KEY: MISC_FEATURE
<222> LOCATION: (227)..(227)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (228)..(228)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (229)..(229)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (230)..(230)
<223> OTHER INFORMATION: Xaa is Asp, Glu, His, Lys, or Arg
<220> FEATURE:
<221> NAME/KEY: MISC_FEATURE
<222> LOCATION: (231)..(231)
<223> OTHER INFORMATION: Xaa is an unknown amino acid
<220> FEATURE:
<221> NAME/KEY: MISC_FEATURE
<222> LOCATION: (232)..(232)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (234)..(234)
<223> OTHER INFORMATION: Xaa is Asp, Glu, His, Lys, or Arg
<220> FEATURE:
<221> NAME/KEY: MISC_FEATURE
<222> LOCATION: (235)..(235)
<223> OTHER INFORMATION: Xaa is Ser or Thr
<220> FEATURE:
<221> NAME/KEY: MISC_FEATURE
<222> LOCATION: (236)..(236)
<223> OTHER INFORMATION: Xaa is Ile, Leu, or Val
<220> FEATURE:
<221> NAME/KEY: MISC_FEATURE
<222> LOCATION: (237)..(238)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (240)..(240)
<223> OTHER INFORMATION: Xaa is Cys, Asp, Glu, His, Lys, Asn, Gln, Arg,
```

```
              Ser, or Thr
<220> FEATURE:
<221> NAME/KEY: MISC_FEATURE
<222> LOCATION: (241)..(241)
<223> OTHER INFORMATION: Xaa is Ile, Leu, or Val
<220> FEATURE:
<221> NAME/KEY: MISC_FEATURE
<222> LOCATION: (242)..(242)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (246)..(247)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (248)..(248)
<223> OTHER INFORMATION: Xaa is an unknown amino acid
<220> FEATURE:
<221> NAME/KEY: MISC_FEATURE
<222> LOCATION: (250)..(250)
<223> OTHER INFORMATION: Xaa is Ile, Leu, or Val
<220> FEATURE:
<221> NAME/KEY: MISC_FEATURE
<222> LOCATION: (253)..(253)
<223> OTHER INFORMATION: Xaa is an unknown amino acid
<220> FEATURE:
<221> NAME/KEY: MISC_FEATURE
<222> LOCATION: (254)..(254)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (255)..(255)
<223> OTHER INFORMATION: Xaa is Cys, Asp, Glu, His, Lys, Asn, Gln, Arg,
      Ser, or Thr
<220> FEATURE:
<221> NAME/KEY: MISC_FEATURE
<222> LOCATION: (256)..(256)
<223> OTHER INFORMATION: Xaa is an unknown amino acid
<220> FEATURE:
<221> NAME/KEY: MISC_FEATURE
<222> LOCATION: (257)..(258)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (259)..(260)
<223> OTHER INFORMATION: Each Xaa is an unknown amino acid
<220> FEATURE:
<221> NAME/KEY: MISC_FEATURE
<222> LOCATION: (261)..(261)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (262)..(262)
<223> OTHER INFORMATION: Xaa is Ala, Cys, Asp, Gly, Asn, Pro, Ser, Thr,
      or Val
<220> FEATURE:
<221> NAME/KEY: MISC_FEATURE
<222> LOCATION: (263)..(263)
<223> OTHER INFORMATION: Xaa is an unknown amino acid
<220> FEATURE:
<221> NAME/KEY: MISC_FEATURE
<222> LOCATION: (264)..(264)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (265)..(265)
<223> OTHER INFORMATION: Xaa is an unknown amino acid
<220> FEATURE:
<221> NAME/KEY: MISC_FEATURE
<222> LOCATION: (266)..(266)
<223> OTHER INFORMATION: Xaa is Asp, Glu, His, Lys, or Arg
<220> FEATURE:
<221> NAME/KEY: MISC_FEATURE
```

```
<222> LOCATION: (267)..(267)
<223> OTHER INFORMATION: Xaa is Ser or Thr
<220> FEATURE:
<221> NAME/KEY: MISC_FEATURE
<222> LOCATION: (268)..(268)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (269)..(270)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: MISC_FEATURE
<222> LOCATION: (271)..(271)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: MISC_FEATURE
<222> LOCATION: (272)..(272)
<223> OTHER INFORMATION: Xaa is an unknown amino acid
<220> FEATURE:
<221> NAME/KEY: MISC_FEATURE
<222> LOCATION: (273)..(274)
<223> OTHER INFORMATION: Each Xaa is Ala, Cys, Asp, Gly, Asn, Pro, Ser,
      Thr, or Val
<220> FEATURE:
<221> NAME/KEY: MISC_FEATURE
<222> LOCATION: (275)..(275)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (281)..(281)
<223> OTHER INFORMATION: Xaa is Ile, Leu, or Val
<220> FEATURE:
<221> NAME/KEY: MISC_FEATURE
<222> LOCATION: (284)..(284)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (286)..(286)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: MISC_FEATURE
<222> LOCATION: (287)..(287)
<223> OTHER INFORMATION: Xaa is Ala, Cys, Asp, Gly, Asn, Pro, Ser, Thr,
      or Val

<400> SEQUENCE: 43

Xaa Xaa Xaa Xaa Xaa Xaa Xaa Xaa Xaa Xaa Xaa Xaa Xaa Ser Xaa
1               5                   10                  15

Xaa Xaa Xaa Xaa Gly Xaa Cys His Pro Asp Cys Xaa Lys Ala Xaa Xaa
                20                  25                  30

Glu Xaa Glu Asp Tyr Asp Ala Ser Gln Xaa Ala Ala Xaa Val Ala Val
        35                  40                  45

Xaa Leu Ile Ser Ser Ala Arg Xaa Xaa Leu Lys Leu Asp Xaa Xaa Xaa
50                  55                  60

Thr Glu Tyr Ser Ala Gln Tyr Leu Val Asp Asn Ala Gly Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Leu Xaa Xaa Xaa Xaa Xaa Xaa Trp Xaa Lys Xaa Xaa Xaa Xaa
            100                 105                 110

Xaa Xaa Xaa Xaa Xaa Xaa Xaa Arg Xaa Xaa Xaa Leu Thr Val Lys Asp
        115                 120                 125

Cys Leu Glu Xaa Ala Phe Lys Lys Gly Xaa Pro Arg Xaa Glu Xaa Trp
130                 135                 140
```

```
Xaa Xaa Xaa Gly Xaa Xaa Xaa Xaa Xaa Pro Pro Xaa Xaa Xaa Xaa Xaa
145                 150                 155                 160

Xaa Xaa Val Xaa Met Lys Gly Glu Val Ile Glu Xaa Xaa Xaa Xaa Xaa
                165                 170                 175

Glu Ala Xaa Xaa Leu Xaa Xaa Xaa Gln Pro Xaa Gly Ala Xaa Leu His
            180                 185                 190

Xaa Phe Xaa Pro Xaa Xaa Xaa Xaa Xaa Xaa Xaa Gly Xaa Tyr Xaa Gly
        195                 200                 205

Xaa Xaa Xaa Xaa Xaa Xaa Xaa Xaa Tyr Val Gly Leu Arg Asp Xaa Xaa
        210                 215                 220

Xaa Xaa Xaa Xaa Xaa Xaa Xaa Xaa Gly Xaa Xaa Xaa Xaa Xaa Val Xaa
225                 230                 235                 240

Xaa Xaa Tyr Lys Lys Xaa Xaa Xaa Phe Xaa Lys Val Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Leu Val Asp Phe Cys Xaa Pro Arg Xaa Ser Xaa Xaa
            275                 280                 285
```